US010759868B2

(12) United States Patent
Schiffer-Mannioui

(10) Patent No.: US 10,759,868 B2
(45) Date of Patent: Sep. 1, 2020

(54) TROPHOBLAST GLYCOPROTEIN (5T4, TPBG) SPECIFIC CHIMERIC ANTIGEN RECEPTORS FOR CANCER IMMUNOTHERAPY

(71) Applicant: CELLECTIS, Paris (FR)

(72) Inventor: Cècile Schiffer-Mannioui, Villiers-sur-Marne (FR)

(73) Assignee: CELLECTIS, Paris (FR)

( * ) Notice: Subject to any disclaimer, the term of this patent is extended or adjusted under 35 U.S.C. 154(b) by 143 days.

(21) Appl. No.: 15/506,643

(22) PCT Filed: Sep. 3, 2015

(86) PCT No.: PCT/EP2015/070128
§ 371 (c)(1),
(2) Date: Feb. 24, 2017

(87) PCT Pub. No.: WO2016/034666
PCT Pub. Date: Mar. 10, 2016

(65) Prior Publication Data
US 2017/0275374 A1 Sep. 28, 2017

(30) Foreign Application Priority Data

Sep. 4, 2014 (DK) .................. 2014 70543

(51) Int. Cl.
C07K 16/30 (2006.01)
C07K 14/735 (2006.01)
C07K 14/705 (2006.01)
C07K 14/725 (2006.01)
C07K 19/00 (2006.01)
C12N 5/078 (2010.01)
C12N 5/0783 (2010.01)

(52) U.S. Cl.
CPC ............ C07K 16/30 (2013.01); C07K 14/705 (2013.01); C07K 14/7051 (2013.01); C07K 14/70517 (2013.01); C07K 14/70535 (2013.01); C07K 14/70578 (2013.01); C07K 19/00 (2013.01); C12N 5/0634 (2013.01); C12N 5/0636 (2013.01); C07K 2317/622 (2013.01); C07K 2319/02 (2013.01); C07K 2319/03 (2013.01); C07K 2319/33 (2013.01); C07K 2319/70 (2013.01); C07K 2319/74 (2013.01); C12N 2510/00 (2013.01)

(58) Field of Classification Search
None
See application file for complete search history.

(56) References Cited

U.S. PATENT DOCUMENTS

| 4,683,195 | A | 7/1987 | Mullis et al. |
| 5,037,743 | A | 8/1991 | Welch et al. |
| 5,143,830 | A | 9/1992 | Holland et al. |
| 5,225,539 | A | 7/1993 | Winter |
| 5,530,101 | A | 6/1996 | Queen et al. |
| 5,585,089 | A | 12/1996 | Queen et al. |
| 5,766,886 | A | 6/1998 | Studnicka et al. |
| 5,858,358 | A | 1/1999 | June et al. |
| 5,883,223 | A | 3/1999 | Gray |
| 6,010,613 | A | 1/2000 | Walters et al. |
| 6,352,694 | B1 | 3/2002 | June et al. |
| 6,407,213 | B1 | 6/2002 | Carter et al. |
| 6,534,055 | B1 | 3/2003 | June et al. |
| 6,692,964 | B1 | 2/2004 | June et al. |
| 6,797,514 | B2 | 9/2004 | Berenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 7,067,318 | B2 | 6/2006 | June et al. |
| 7,144,575 | B2 | 12/2006 | June et al. |
| 7,172,869 | B2 | 2/2007 | June et al. |
| 7,175,843 | B2 | 2/2007 | June et al. |
| 7,232,566 | B2 | 6/2007 | June et al. |
| 2002/0132983 | A1 | 9/2002 | Junghans |
| 2003/0105000 | A1 | 6/2003 | Pero et al. |
| 2005/0042664 | A1 | 2/2005 | Wu et al. |
| 2005/0048617 | A1 | 3/2005 | Wu et al. |

(Continued)

FOREIGN PATENT DOCUMENTS

EP 0239400 8/1994
EP 0592106 11/2004
(Continued)

OTHER PUBLICATIONS

Mariuzza et al. (Annu. Rev. Biophys. Biophys. Chem., 16: 139-159, 1987).*
Arimondo et al., "Exploring the cellular activity of camptothecin-triple-helix-fonning oligonucleotide conjugates," Mol. Cell Biol., 26(1):324-33, Jan. 2006.
Atkins et al.,"A case for "StopGo": reprogramming translation to augment codon meaning of GGN by promoting unconventional termination (Stop) after addition of glycine and then allowing continued translation (Go)," Rna., 13(6):803-10, Jun. 2007.

(Continued)

Primary Examiner — Brad Duffy
(74) Attorney, Agent, or Firm — Fish & Richardson P.C.

(57) ABSTRACT

The present invention relates to Chimeric Antigen Receptors (CAR) that are recombinant chimeric proteins able to redirect immune cell specificity and reactivity toward selected membrane antigens, and more particularly in which extracellular ligand binding is a scFV derived from a 5T4 monoclonal antibody, conferring specific immunity against 5T4 positive cells. The engineered immune cells endowed with such CARs are particularly suited for treating lymphomas and leukemia, and for solid tumors such as colon, stomach, and ovarian tumors.

8 Claims, 8 Drawing Sheets
Specification includes a Sequence Listing.

(56) References Cited

U.S. PATENT DOCUMENTS

| | | |
|---|---|---|
| 2006/0121005 A1 | 6/2006 | Berenson et al. |
| 2007/0231333 A1* | 10/2007 | Boghaert ............ A61K 47/6849 424/155.1 |
| 2013/0280221 A1 | 10/2013 | Schonfeld et al. |
| 2013/0287748 A1 | 10/2013 | June et al. |
| 2014/0234348 A1* | 8/2014 | Scholler ............... C07K 14/465 424/184.1 |
| 2015/0038684 A1 | 2/2015 | Jensen |
| 2017/0283497 A1 | 10/2017 | Schiffer-Mannioui |

FOREIGN PATENT DOCUMENTS

| | | | |
|---|---|---|---|
| EP | 519596 | 2/2005 | |
| JP | 2014/510108 | 4/2014 | |
| WO | WO 91/09967 | 7/1991 | |
| WO | WO 93/17105 | 9/1993 | |
| WO | WO 2004/083379 | 9/2004 | |
| WO | WO 2012/012695 | 1/2012 | |
| WO | WO 2012/097313 | 7/2012 | |
| WO | WO 2012/138927 | 10/2012 | |
| WO | WO-2013033626 A2 * | 3/2013 | ....... C07K 14/70503 |
| WO | WO 2013/063419 | 5/2013 | |
| WO | WO 2013/123061 | 8/2013 | |
| WO | WO 2013/176915 | 11/2013 | |
| WO | WO 2014/031174 | 2/2014 | |
| WO | WO 2014/031687 | 2/2014 | |
| WO | WO 2014/039523 | 3/2014 | |

OTHER PUBLICATIONS

Baskar et al., "Unique cell surface expression of receptor tyrosine kinase ROR1 in human B-cell chronic lymphocytic leukemia," Clin. Cancer Res. Off. J. Am. Assoc. Cancer Res., 14(2):396-404, Jan. 2008.

Bicocca et al., "Crosstalk between ROR1 and the Pre-B cell receptor promotes survival oft (1; 19) acute lymphoblastic leukemia," Cancer Cell, 22(5):656-667, Nov. 2012.

Bierer et al., "Cyclosporin A and FK506: molecular mechanisms of immunosuppression and probes for transplantation biology," Curr. Opin. Immunol., 5(5):763-73, Oct. 1993.

Birkle et al., "Role of tumor-associated gangliosides in cancer progression," Biochimie., 85(3-4):455-463, Mar.-Apr. 2003.

Boch et al., "Breaking the code of DNA binding specificity of TAL-type III effectors," Science, 326(5959):1509-12, Dec. 2009.

Carsberg et al., "Metastasis-associated 5T4 oncofoetal antigen is concentrated at microvillus projections of the plasma membrane," J. Cell Sci., 108(8):2905-16, Aug. 1995.

Castro et al., "5T4 oncofetal antigen is expressed in high risk of relapse childhood pre-B acute lymphoblastic leukemia and is associated with a more invasive and chemotactic phenotype," Leukemia., 26(7):1487-98, Jul. 2012.

Choudhury et al., "Silencing of ROR1 and FMOD with siRNA results in apoptosis of CLL cells," Br. J. Haematol., 151(4):327-335, Nov. 2010.

Choulika et al., "Induction of homologous recombination in mammalian chromosomes by using the I-Seel system of *Saccharomyces cerevisiae*," Mol. Cell. Biol., 15(4):1968-73, Apr. 1995.

Christian et al., "Targeting DNA double-strand breaks with TAL effector nucleases," Genetics, 186(2):757-61, Oct. 2010.

Cong et al., "Multiplex genome engineering using CRISPR/Cas systems," Science, 339(6121):819-23, Feb. 2013.

Cooper, "L. Innovative T Cell-Targeted Therapy for Ovarian Cancer," Annual Report 2012 prepared for US Army medical research and Medical Command.

Cros et al., "Problems related to resistance to cytarabine in acute myeloid leukemia," Leukemia & Lymphoma, 45(6):1123-1132, Jun. 2004.

Daneshmanesh et al., "Ror1, a cell surface receptor tyrosine kinase is expressed in chronic lymphocytic leukemia and may serve as a putative target for therapy," Int. J. Cancer, 123(5):1190-5, Sep. 2008.

Daniotti et al., "Cloning, characterization and developmental expression of alpha2,8 sialyltransferase (GD3 synthase, ST8Sia I) gene in chick brain and retina," Int. J. Dev. Neurosci., 15(6):767-776, Oct. 1997.

Dave et al., "Restricted cell surface expression of receptor tyrosine kinase ROR1 in pediatric B-lineage acute lymphoblastic leukemia suggests targetability with therapeutic monoclonal antibodies," PLoS One., 7(12):e52655, Dec. 2012.

Deltcheva et al., "CRISPR RNA maturation by trans-encoded small RNA and host factor RNase III," Nature, 471(7340):602-7, Mar. 2011.

Donelly et al., "The cleavage activities of aphthovirus and cardiovirus 2A proteins," J. Gen. Virol., 78:13-21, Jan. 1997.

Donnelly and Elliott, "Nuclear localization and shuttling of herpes simplex virus tegument protein VP13/14," J. Virol., 75(6):2566-74, Mar. 2001.

Donnelly et al., "Analysis of the aphthovirus 2A/2B polyprotein 'cleavage' mechanism indicates not a proteolytic reaction, but a novel translational effect: a putative ribosomal 'skip'," J. Gen. Virol., 82:1013-1025, May 2001.

Doronina et al., "Site-specific release of nascent chains from ribosomes at a sense codon," Mol. Cell Biol., 28(13):4227-39, Jul. 2008.

Dotti et al., "Redirecting T-cell specificity by introducing a tumor-specific chimeric antigen receptor," Blood., 116(7):1035-1044, Aug. 2010.

Eisenschmidt et al., "Developing a programmed restriction endonuclease for highly specific DNA cleavage." Nucleic. Acids. Res., 33(22):7039-47, Jan. 2005.

Fukuda et al., "Antisera induced by infusions of autologous Ad-CD154-leukemia B cells identify ROR1 as an oncofetal antigen and receptor for Wnt5a," Proc. Natl. Acad. Sci. U.S.A., 105(8):3047-3052, Feb. 2008.

Gardin et al., "Postremission treatment of elderly patients with acute myeloid leukemia in first complete remission after intensive induction chemotherapy: results of the multicenter randomized Acute Leukemia French Association (ALFA) 9803 trial," Blood., 109(12):5129-5135, Jun. 2007.

Garneau et al., "The CRISPR/Cas bacterial immune system cleaves bacteriophage and plasmid DNA," Nature, 468(7320):67-71, Nov. 2010.

Gasiunas et al., "Cas9-crRNA ribonucleoprotein complex mediates specific DNA cleavage for adaptive immunity in bacteria," Proc. Natl. Acad. Sci. U.S.A., 109(39):E2579-86, Sep. 2012.

GenBank Association No. AAA53133.1, "4-1BB [*Homo sapiens*]," Nov. 27, 1994, 2 pages.

GenBank Association No. NP001139345.1, "T-cell surface glycoprotein CD8 alpha chain isoform 1 precursor [*Homo sapiens*]," Mar. 15, 2015, 3 pages.

GenBank Association No. NP001992.1, "high affinity immunoglobulin epsilon receptor subunit alpha precursor [*Homo sapiens*]," Jan. 15, 2016, 3 pages.

GenBank Association No. NP006130.1, "T-cell-specific surface glycoprotein CD28 isoform 1 precursor [*Homo sapiens*]," Mar. 15, 2015, 3 pages.

Gentile et al., "Ror1 is a pseudokinase that is crucial for Met-driven tumorigenesis," Cancer Res., 71(8):3132-3141, Apr. 2011.

Gravotta et al., "In vivo and in vitro expression of gangliosides in chick retina Müeller cells," J. Neurochem., 52(3):768-776, Mar. 1989.

Guest et al., "The role of extracellular spacer regions in the optimal design of chimeric immune receptors: evaluation of four different scFvs and antigens," J. Immunother., 28(3):203-211, May 2005.

Haraguchi et al., "Isolation of GD3 synthase gene by expression cloning of GM3 alpha-2,8-sialyltransferase cDNA using anti-GD2 monoclonal antibody," Proc. Natl. Acad. Sco. U.S.A., 91(22):10455-10459, Oct. 1994.

Haynes et al., "Redirecting mouse CTL against colon carcinoma: superior signaling efficacy of single-chain variable domain chimeras containing TCR-zeta vs Fc epsilon RI-gamma," J. of Immunol., 166(1):182-187, Jan. 2001.

(56) References Cited

OTHER PUBLICATIONS

Henderson et al., "Comparison of the effects of FK-506, cyclosporin A and rapamycin on IL-2 production," Immunology, 73(3):316-21, Jul. 1991.
Hole and Stern., "A 72 kD trophoblast glycoprotein defined by a monoclonal antibody," Br. J. Cancer, 57(3):239-246, Mar. 1988.
Hudecek et al., "Receptor affinity and extracellular domain modifications affect tumor recognition by ROR1-specific chimeric antigen receptor T cells," Clin Canc Res., 19(12):3153-3164, Apr. 25, 2013.
International Search Report and Written Opinion issued in PCT/EP2015/067444, dated Oct. 19, 2015.
Jena et al., "Redirecting T-cell specificity by introducing a tumor-specific chimeric antigen receptor," Blood, 116(7):1035-44, Aug. 2010.
Jinek et al., "A programmable dual-RNA-guided DNA endonuclease in adaptive bacterial immunity," Science, 337(6096):816-21, Jun. 2012.
June et al., "T cells with chimeric antigen receptors have potent antitumor effects and can establish memory in patients with advanced leukemia," Sci. Transl. Med., 3(95):95ra73, Aug. 2011.
Kalish and Glazer, "Targeted genome modification via triple helix formation," Ann. N.Y. Acad. Sci., 1058(1):151-61, Nov. 2005.
Klein et al., "Gene expression profiling of B cell chronic lymphocytic leukemia reveals a homogeneous phenotype related to memory B cells," J. Exp. Med., 194:1625-1638, Dec. 2001.
Li et al., "TAL nucleases (TALNs): hybrid proteins composed of TAL effectors and FokI DNA-cleavage domain," Nucleic. Acids. Res., 39(1):359-72, Jan. 2011.
Liu et al., "Calcineurin is a common target of cyclophilin-cyclosporin A and FKBP-FK506 complexes," Cell, 66(4):807-815, Aug. 1991.
Liu et al., "Inhibition of T cell signaling by immunophilin-ligand complexes correlates with loss of calcineurin phosphatase activity," Biochemistry., 31(16):3896-901, Apr. 1992.
Lo et al., "Anti-GD3 chimeric sFv-CD28/T-cell receptor zeta designer T cells for treatment of metastatic melanoma and other neuroectodermal tumors," Clin. Cancer Res., 16(10):2769-2780, May 2010.
Mali et al., "RNA-guided human genome engineering via Cas9," Science, 339(6121):823-6, Feb. 2013.
Mannioui et al., "Treatment of B cells malignancies with anti-CD19 CAR+, TCR-, CD52-allogeneic T cells," J ImmunoTherapy Canc., BioMed Central Ltd, London UK, 1(Suppl 1):p. 34, Nov. 7, 2013.
Matsuda et al., "Expression of the receptor tyrosine kinase genes, Ror1 and Ror2, during mouse development," Mech. Dev., 105(1-2):153-156, Jul. 2001.
Moscou and Bogdanove, "A simple cipher governs DNA recognition by TAL effectors," Science, 326(5959):1501, Dec. 2009.
Nakayama et al., "Expression cloning of a human GT3 synthase. GD3 and GT3 are synthesized by a single enzyme," J. Biol. Chem., 271(7):3684-91, Feb. 1996.
Padlan, "A possible procedure for reducing the immunogenicity of antibody variable domains while preserving their ligand-binding properties," Mol. Immunol., 28(4-5):489-498, Apr.-May 1991.
Paques and Duchateau, "Meganucleases and DNA double-strand break-induced recombination: perspectives for gene therapy," Curr. Gene Ther., 7(1):49-66, Feb. 2007.
Park et al., "Treating cancer with genetically engineered T cells," Trends Biotechnol., 29(11):550-7, Nov. 2011.
Peipp et al., "Efficient eukaryotic expression of fluorescent scFv fusion proteins directed against CD antigens for FACS applications," J. Immunol. Methods, 285(2):265-80, Feb. 2004.
Perrin et al., "Asymmetrical recognition and activity of the I-SceI endonuclease on its site and on intron-exon junctions," Embo. J., 12(7):2939-47, Jul. 1993.
Pingoud and Silva, "Precision genome surgery," Nat. Biotechnol., 25(7):743-4, Jul. 2007.
Poirot et al., "521 multiplex genome editing of TCR a/CD52 Genes as a platform for "Off the Shelf" Adoptive T-cell immunotherapies," 17th Annual Meeting of the American-Sciety-of-Gene-and-Cell-Therapy (ASGCT), 22(Suppl. 1):S201-S202, May 1, 2014, Washington DC., USA.
Poirot et al., "T-Cell engineering for "off-the-shelf" Adoptive Immunotherapy," Blood., 122(21):1661, Nov. 15, 2013.
Porter et al., "Chimeric antigen receptor-modified T cells in chronic lymphoid leukemia," N. Engl. J. Med., 365(8):725-733, Aug. 2011.
Porteus and Carroll, "Gene targeting using zinc finger nucleases," Nat. Biotechnol., 23(8):967-73, Aug. 2005.
Reaman et al., "Anti-GD3 monoclonal antibody analysis of childhood T-cell acute lymphoblastic leukemia: detection of a target antigen for antibody-mediated cytolysis," Cancer Res., 50(1):202-205, Jan. 1990.
Reddy et al., "Localization of the human Ror1 gene (NTRKR1) to chromosome 1p31-p32 by fluorescence in situ hybridization and somatic cell hybrid analysis," Genomics, 41(2):238-5, Apr. 1997.
Rosenwald et al., "Relation of gene expression phenotype to immunoglobulin mutation genotype in B cell chronic lymphocytic leukemia," J. Exp. Med., 194(11):1639-1647, Dec. 2001.
Rouet et al., "Introduction of double-strand breaks into the genome of mouse cells by expression of a rare-cutting endonuclease," Mol. Cell Biol., 14(12):8096-106, Dec. 1994.
Sorek et al., "CRISPR-mediated adaptive immune systems in bacteria and archaea," Annu. Rev. Biochem., Jun. 2013.
Starzynska et al., "5T4 oncofetal antigen in gastric carcinoma and its clinical significance," Eur. J. Gatrerol Heptol., 10(6):479-84, Jun. 1998.
Stoddard, "Homing endonuclease structure and function," Q. Rev. Biophys., 38(1):49-95, Feb. 2005.
Studincka et al., "Human-engineered monoclonal antibodies retain full specific binding activity by preserving non-CDR complementarity-modulating residues," Protein Eng., 7(6):805-814, Jun. 1994.
Yamaguchi et al., "NKX2-1/TITF1/TTF-1-Induced ROR1 is required to sustain EGFR survival signaling in lung adenocarcinoma," Cancer Cell, 21(3):348-361, Mar. 2012.
Yun et al., "Targeting of T lymphocytes to melanoma cells through chimeric anti-GD3 immunoglobulin T-cell receptors," Neoplasia., 2(5):449-459, Sep.-Oct. 2000.
Zhang et al., "ROR1 is expressed in human breast cancer and associated with enhanced tumor-cell growth," PLoS One, 7(3):e31127, Mar. 2012.
Zhang et al., "The onco-embryonic antigen ROR1 is expressed by a variety of human cancers," Am. J. Pathol., 181(6):1903-1910, Dec. 2012.
Almagro and Fransson, "Humanization of antibodiesHumanization of antibodies," Frontiers in Bioscience, 13: 1619-33, Jan. 2008.
Banihashenni et al., "Development of specific nanobodies (VHH) for CD19 immuno-targeting of human B-lymphocytes," Iran. J. Basic. Med. Sci., 21(5):455-464, May 2018.
Burgess et al., "Possible dissociation of the heparin-binding and mitogenic activities of heparin-binding (acidic fibroblast) growth factor-1 from its receptor-binding activities by site-directed mutagenesis of a single lysine residue" J. of Cell. Biol., 111(5 Pt 1):2129-2138, Nov. 1990.
Coleman et al., "Effects of amino acid sequence changes on antibody-antigen interactions," Res. Immunol., 145(1):33-36, Jan. 1994.
Lbraginnova and Wade, "Stability of the beta-sheet of the WW domain: A molecular dynamics simulation study," Biophys. J., 77(4):2191-2198, Oct. 1999.
Rudikoff et al., "Single amino acid substitution altering antigen-binding specificity," Proc. Natl. Acad. Sci. U.S.A., 79(6):1979-1983, Mar. 1982.
Edwards et al., "The remarkable flexibility of the human antibody repertoire; isolation of over one thousand different antibodies to a single protein, BLyS," J. Mol. Biol., 334(1):103-118, Nov. 2003.
Lloyd et al., "Modelling the human immune response: performance of a 1011 human antibody repertoire against a broad panel of therapeutically relevant antigens," Protein Eng. Des. Sel., 22(3):159-168, Mar. 2009.

* cited by examiner

| Construct | Leader | VH | Linker | VL | Hinge | TM | Costim | Signal |
|---|---|---|---|---|---|---|---|---|
| A1-v3 | CD8α leader | A1 VH | (G4S)3 linker | A1 VL | CD8α hinge | CD8α TM | 41BB | CD3ζ |
| A1-v5 | CD8α leader | A1 VH | (G4S)3 linker | A1 VL | IgG1 hinge | CD8α TM | 41BB | CD3ζ |
| A1-v1 | CD8α leader | A1 VH | (G4S)3 linker | A1 VL | FcγRIIIα hinge | CD8α TM | 41BB | CD3ζ |
| A1-v4 | CD8α leader | A1 VH | (G4S)3 linker | A1 VL | CD8α hinge | 41BB TM | 41BB | CD3ζ |
| A1-v6 | CD8α leader | A1 VH | (G4S)3 linker | A1 VL | IgG1 hinge | 41BB TM | 41BB | CD3ζ |
| A1-v2 | CD8α leader | A1 VH | (G4S)3 linker | A1 VL | FcγRIIIα hinge | 41BB TM | 41BB | CD3ζ |

Figure 3

| | | | | | | | |
|---|---|---|---|---|---|---|---|
| A2-v3 | CD8α leader | A2 VH | (G4S)3 linker | A2 VL | CD8α hinge | CD8α TM | 41BB | CD3ζ |
| A2-v5 | CD8α leader | A2 VH | (G4S)3 linker | A2 VL | IgG1 hinge | CD8α TM | 41BB | CD3ζ |
| A2-v1 | CD8α leader | A2 VH | (G4S)3 linker | A2 VL | FcγRIIIα hinge | CD8α TM | 41BB | CD3ζ |
| A2-v4 | CD8α leader | A2 VH | (G4S)3 linker | A2 VL | CD8α hinge | 41BB TM | 41BB | CD3ζ |
| A2-v6 | CD8α leader | A2 VH | (G4S)3 linker | A2 VL | IgG1 hinge | 41BB TM | 41BB | CD3ζ |
| A2-v2 | CD8α leader | A2 VH | (G4S)3 linker | A2 VL | FcγRIIIα hinge | 41BB TM | 41BB | CD3ζ |

Figure 4

| Construct | Components |
|---|---|
| A3-v3 | CD8α leader \| A3 VH \| (G4S)3 linker \| A3 VL \| CD8α hinge \| CD8α TM \| 41BB \| CD3ζ |
| A3-v5 | CD8α leader \| A3 VH \| (G4S)3 linker \| A3 VL \| IgG1 hinge \| CD8α TM \| 41BB \| CD3ζ |
| A3-v1 | CD8α leader \| A3 VH \| (G4S)3 linker \| A3 VL \| FcγRIIIα hinge \| CD8α TM \| 41BB \| CD3ζ |
| A3-v4 | CD8α leader \| A3 VH \| (G4S)3 linker \| A3 VL \| CD8α hinge \| 41BB TM \| 41BB \| CD3ζ |
| A3-v6 | CD8α leader \| A3 VH \| (G4S)3 linker \| A3 VL \| IgG1 hinge \| 41BB TM \| 41BB \| CD3ζ |
| A3-v2 | CD8α leader \| A3 VH \| (G4S)3 linker \| A3 VL \| FcγRIIIα hinge \| 41BB TM \| 41BB \| CD3ζ |

Figure 5

| | | | | | | |
|---|---|---|---|---|---|---|
| H8-v3 | CD8α leader | H8 VH | (G4S)3 linker | H8 VL | CD8α hinge | CD8α TM | 41BB | CD3ζ |
| H8-v5 | CD8α leader | H8 VH | (G4S)3 linker | H8 VL | IgG1 hinge | CD8α TM | 41BB | CD3ζ |
| H8-v1 | CD8α leader | H8 VH | (G4S)3 linker | H8 VL | FcγRIIIα hinge | CD8α TM | 41BB | CD3ζ |
| H8-v4 | CD8α leader | H8 VH | (G4S)3 linker | H8 VL | CD8α hinge | 41BB TM | 41BB | CD3ζ |
| H8-v6 | CD8α leader | H8 VH | (G4S)3 linker | H8 VL | IgG1 hinge | 41BB TM | 41BB | CD3ζ |
| H8-v2 | CD8α leader | H8 VH | (G4S)3 linker | H8 VL | FcγRIIIα hinge | 41BB TM | 41BB | CD3ζ |

Figure 6

TROPHOBLAST GLYCOPROTEIN (5T4, TPBG) SPECIFIC CHIMERIC ANTIGEN RECEPTORS FOR CANCER IMMUNOTHERAPY

CROSS-REFERENCE TO RELATED APPLICATIONS

This application is a National Stage entry of International Application No.: PCT/EP2015/070128, filed Sep. 3, 2015, which claims priority to Danish Patent Application No. PA201470543, filed Sep. 4, 2014. The disclosure of the priority applications are hereby incorporated in their entirety by reference.

FIELD OF THE INVENTION

The present invention relates to Chimeric Antigen Receptors (CAR) that are recombinant chimeric proteins able to redirect immune cell specificity and reactivity toward 5T4, a cell surface glycoprotein found on most myeloid cells and used to diagnose solid tumors such as stomach, colon and ovarian tumors, and pre-B acute lymphocytic leukemia (ALL) in patients. The CARs according to the invention are particularly useful to treat malignant cells bearing 5T4 antigen, when expressed in T-cells or NK cells. The resulting engineered immune cells display high level of specificity toward malignant cells, conferring safety and efficiency for immunotherapy.

BACKGROUND OF THE INVENTION

Adoptive immunotherapy, which involves the transfer of autologous antigen-specific T cells generated ex vivo, is a promising strategy to treat viral infections and cancer. The T cells used for adoptive immunotherapy can be generated either by expansion of antigen-specific T cells or redirection of T cells through genetic engineering (Park, Rosenberg et al. 2011). Transfer of viral antigen specific T cells is a well-established procedure used for the treatment of transplant associated viral infections and rare viral-related malignancies. Similarly, isolation and transfer of tumor specific T cells has been shown to be successful in treating melanoma.

Novel specificities in T cells have been successfully generated through the genetic transfer of transgenic T cell receptors or chimeric antigen receptors (CARS) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T-cell cytotoxicity. However, they failed to provide prolonged expansion and anti-tumor activity in vivo. Signaling domains from co-stimulatory molecules, as well as transmembrane and hinge domains have been added to form CARs of second and third generations, leading to some successful therapeutic trials in humans, where T-cells could be redirected against malignant cells expressing CD19 (June et al., 2011). However, the particular combination of signaling domains, transmembrane and co-stimulatory domains used with respect to CD19 ScFv, was rather antigen-specific and cannot be expanded to any antigen markers.

According to the data from the Centers for Disease Control and Prevention. [http://www.cdc.gov/cancer/colorectal/statistics/race.htm], incidence of colorectal cancer in the US population over the year 2011 was about 50 per 100 000 people for women and up to 60 for males in the black people population, leading to 50% mortality. This incidence has only decreased by 10% over the last decade.

One candidate antigen of immunotherapies for solid tumors, including the colorectal, ovarian and gastric and also for non-solid tumors such as childhood acute lymphoblastic leukemia (ALL) is the trophoblast glycoprotein, also known as TPBG or 5T4 (UniProt: 013641). 5T4 is often referred to as an oncofetal antigen due to its expression in foetal trophoblast (where it was first discovered) or trophoblast glycoprotein (TPBG). 5T4 protein is an N-glycosylated transmembrane 72 kDa glycoprotein containing seven leucine-rich repeat regions (Hole et al, 1988). The 5T4 antigen was found to be expressed in number of carcinoma including gastric (Starzynska et al. 1995), ovarian and carcinoma (Wrigley et al. 1995). Also, 5T4 oncofetal antigen is expressed in high risk of relapse childhood pre-B acute lymphoblastic leukemia (Castro et al. 2012). It has very limited expression in normal tissue but is widespread in malignant tumors throughout their development (Cars berg et al. 1995).

The present inventors have thus considered that 5T4 could be a valuable target antigen for treating solid tumors such as colorectal, ovarian and gastric tumors, by using CAR-expressing T cells.

As an alternative to the previous strategies, the present invention provides with 5T4 specific CARs, which can be expressed in immune cells to target 5T4 malignant cells with significant clinical advantage.

There is still the need for the improvement of CAR functionality by designing CAR architecture and using suitable components since these parameters play a role important and a fine tuning may be necessary.

The inventors have found that, by combining CAR architecture to the choice of suitable components, they could obtain specific 5T4 single chain CARs with high cytotoxicity towards cancerous target cells.

SUMMARY OF THE INVENTION

The inventors have generated 5T4 specific CAR having different structure and comprising different scFV derived from different 5T4 specific antibodies.

In the framework of the present invention, they have designed and implemented at 5T4 specific CAR having one of the polypeptide structure selected from V1 to V6 as illustrated in FIG. 2, said structure comprising an extra cellular ligand binding-domain comprising VH and VL from a monoclonal anti-5T4 antibody, a hinge, a transmembrane domain and a cytoplasmic domain including a CD3 zeta signaling domain and a co-stimulatory domain from 4-1BB. Preferred CAR polypeptides of the invention comprise an amino acid sequence selected from SEQ ID NO.19 to 42. Following non-specific activation in vitro (e.g. with anti CD3/CD28 coated beads and recombinant IL2), T-cells from donors have been transformed with polynucleotides expressing these CARs using viral transduction. More preferred CAR polypeptides having a polypeptide structure selected from V3, V5, V1 (i.e. having the CD8a transmembrane domain) have shown the best and unexpected results.

In particular, the 5T4 specific CARs containing the scFvs from A1, A2, A3 and H8 antibodies represent suitable candidates for immunotherapy as shown by their activity and specificity tested against selected tumor cell lines expressing the 5T4 antigen.

In certain instances, the T-cells were further engineered to create non-alloreactive T-cells, more especially by disruption of a component of TCR (αβ-T-Cell receptors) to prevent Graft versus host reaction.

The resulting engineered T-cells displayed reactivity in-vitro against 5T4 positive cells to various extend, showing that the CARs of the present invention contribute to antigen dependent activation, and also proliferation, of the T-cells, making them useful for immunotherapy.

The polypeptides and polynucleotide sequences encoding the CARs of the present invention are detailed in the present specification.

The engineered immune cells of the present invention are particularly useful for therapeutic applications, such as for treating chronic lymphocytic leukemia or on solid tumors such as breast, colon, lung, and kidney tumors.

BRIEF DESCRIPTION OF THE FIGURES

FIGS. 3 to 6: schematic representation of the v1 to v6 T cell CARs accordingly to FIG. 2 with the VH and VL chains from A1, A2, A3 and H8 antibodies.

TABLE 1

Sequence of the different CAR components

Figure 1:
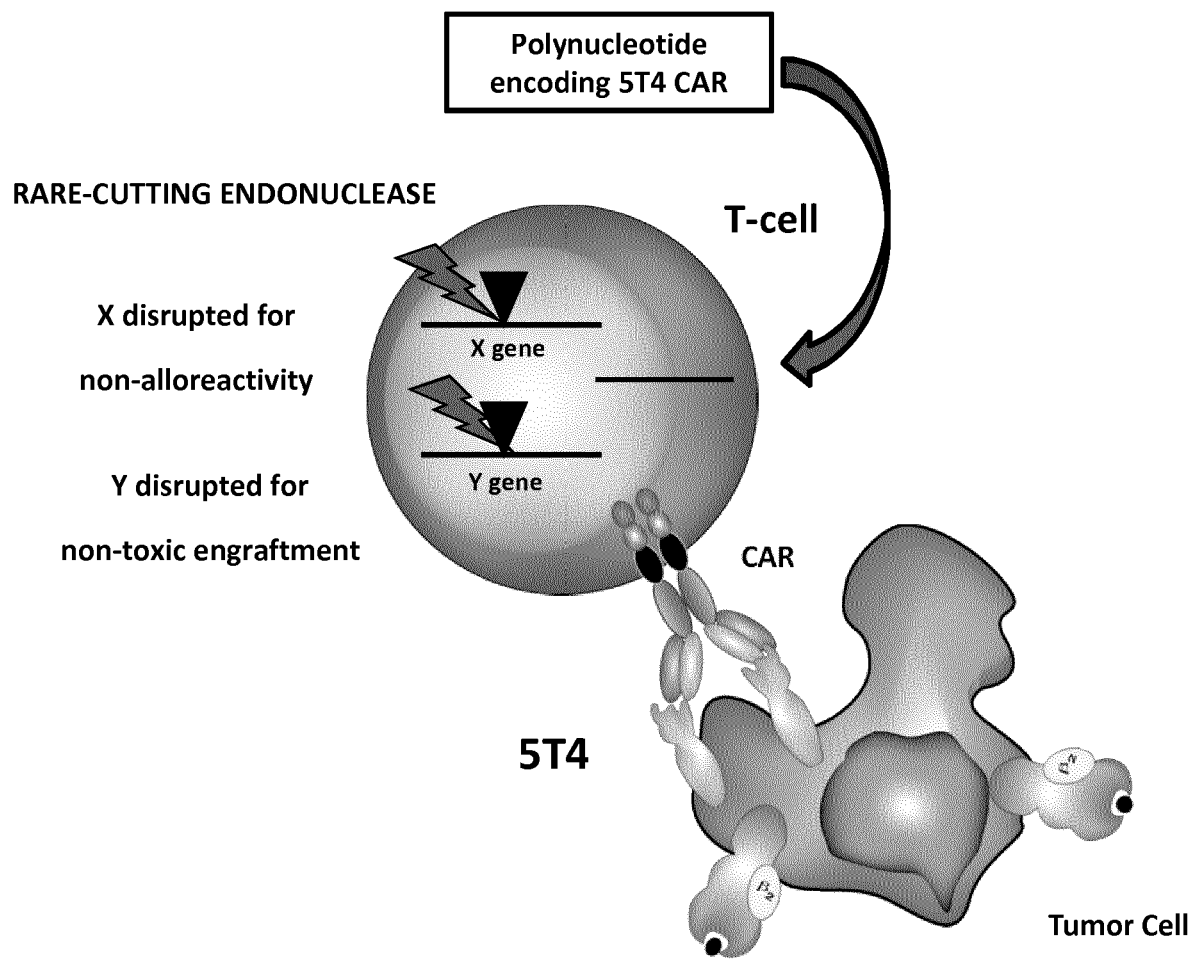
FIG. 1: Schematic representation of an engineered immune cell according to the invention. The engineered immune cell presented in this figure is a T-cell transduced with a retroviral polypeptide encoding CAR. This T-cell is further engineered to allow a better and safer engraftment into the patient, which is optional within the frame of the present invention. X gene may be for instance a gene expressing a component of TCR (TCRalpha or TCRbeta), Y may be a gene involved into the sensitivity of T-cells to immune-suppressive drugs like CD52 (with respect to Campath) or HPRT (with respect to 6-Thioguanine).

| Functional domains | SEQ ID # | Raw amino acid sequence |
|---|---|---|
| CD8α signal peptide | SEQ ID NO. 1 | MALPVTALLLPLALLLHAARP |
| Alternative signal peptide | SEQ ID NO. 2 | METDTLLLWVLLLWVPGSTG |
| FcεRIIIγ hinge | SEQ ID NO. 3 | GLAVSTISSFFPPGYQ |
| CD8α hinge | SEQ ID NO. 4 | TTTPAPRPPTPAPTIASQPLSLRPEACRPAAGGAVHTRGLDFACD |
| IgG1 hinge | SEQ ID NO. 5 | EPKSPDKTHTCPPCPAPPVAGPSVFLFPPKPKDTLMIARTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| CD8α transmembrane domain | SEQ ID NO. 6 | IYIWAPLAGTCGVLLLSLVITLYC |
| 41BB transmembrane domain | SEQ ID NO. 7 | IISFFLALTSTALLFLLFFLTLRFSVV |
| 41BB intracellular domain | SEQ ID NO. 8 | KRGRKKLLYIFKQPFMRPVQTTQEEDGCSCRFPEEEEGGCEL |
| CD3ζ intracellular domain | SEQ ID NO. 9 | RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| G4Sx3 linker | SEQ ID NO. 10 | GGGGSGGGGSGGGGS |

TABLE 2

Sequence of the VH and VL chaines of different scFvs and their respective CDRs

| ScFv sequences | SEQ ID # | Raw amino acid sequence |
|---|---|---|
| H8 heavy chain variable region | SEQ ID NO. 11 | EVQLQQSGPDLVKPGASVKISCKASGYSFTGYYMHWVKQSHGKSLEWIGRINP NNGVTLYNQKFKDKAILTVDKSSTTAYMELRSLTSEDSAVYYCARSTMITNYVM DYWGQVTSVTVSS |
| | SEQ ID NO. 48 | CDR1 GYSFTGYY |
| | SEQ ID NO. 49 | CDR2 INPNNGVT |
| | SEQ ID NO. 50 | CDR3 ARSTMITNYVMDY |
| H8 light chain variable region | SEQ ID NO. 12 | SIVMTQTPTFLLVSAGDRVTITCKASQSVSNDVAWYQQKPGQSPTLLISYTSSRY AGVPDRFIGSGYGTDFTFTISTLQAEDLAVYFCQQDYNSPPTFGGGTKLEIKR |
| | SEQ ID NO. 51 | CDR1 QSVSND |
| | SEQ ID NO. 52 | CDR2 YTS |
| | SEQ ID NO. 53 | CDR3 QQDYNSPPT |
| A1 heavy chain variable region | SEQ ID NO. 13 | QIQLVQSGPELKKPGETVKISCKASGYTFTNFGMNWVKQGPGEGLKWMGWIN TNTGEPRYAEEFKGRFAFSLETTASTAYLQINNLKNEDTATYFCARDWDGAYFFD YWGQGTTLTVSS |
| | SEQ ID NO. 54 | CDR1 GYTFTNFG |
| | SEQ ID NO. 55 | CDR2 INTNTGEP |
| | SEQ ID NO. 56 | CDR3 ARDWDGAYFFDY |
| A1 light chain variable region | SEQ ID NO. 14 | SIVMTQTPKFLLVSAGDRVTITCKASQSVSNDVAWYQQKPGQSPKLLINFATNR YTGVPNRFTGSGYGTDFTFTISTVQAEDLALYFCQQDYSSPWTFGGGTKLEIK |
| | SEQ ID NO. 57 | CDR1 QSVSND |
| | SEQ ID NO. 58 | CDR2 FAT |
| | SEQ ID NO. 59 | CDR3 QQDYSSPWT |
| A2 heavy chain variable region | SEQ ID NO. 15 | QVQLQQSRPELVKPGASVKMSCKASGYTFTDYVISWVKQRTGQGLEWIGEIYP GSNSIYYNEKFKGRATLTADKSSSTAYMQLSSLTSEDSAVYFCAMGGNYGFDYW GQGTTLTVSS |
| | SEQ ID NO. 60 | CDR1 GYTFTDYV |
| | SEQ ID NO. 61 | CDR2 IYPGSNSI |
| | SEQ ID NO. 62 | CDR3 AMGGNYGFDY |
| A2 light chain variable region | SEQ ID NO. 16 | QIVLTQSPAIMSASLGERVILTCTASSSVNSNYLHWYQQKPGSSPKLWIYSTSNL ASGVPARFSGSGSGTSYSLTISSMEAEDAATYYCHQYHRSPLTFGAGTKLELK |
| | SEQ ID NO. 63 | CDR1 SSVNSNY |
| | SEQ ID NO. 64 | CDR2 STS |
| | SEQ ID NO. 65 | CDR3 HQYHRSPLT |
| A3 heavy chain variable region | SEQ ID NO. 17 | EVQLVESGGGLVQPKGSLKLSCAASGFTFNTYAMNWVRQAPGKGLEWVARIR SKSNNYATYYADSVKDRFTISRDDSQSMLYLQMNNLKTEDTAMYYCVRQWDY DVRAMNYWGQGTSVTVSS |
| | SEQ ID NO. 66 | CDR1 GFTFNTYA |
| | SEQ ID NO. 67 | CDR2 IRSKSNNYAT |
| | SEQ ID NO. 68 | CDR3 VRQWDYDVRAMNY |
| A3 light chain variable region | SEQ ID NO. 18 | DIVMTQSHIFMSTSVGDRVSITCKASQDVDTAVAWYQQKPGQSPKLLIYWAST RLTGVPDRFTGSGSGTDFTLTISNVQSEDLADYFCQQYSSYPYTFGGGTKLEIK |
| | SEQ ID NO. 69 | CDR1 QDVDTA |
| | SEQ ID NO. 70 | CDR2 WAS |

TABLE 2-continued

Sequence of the VH and VL chaines of different scFvs and their respective CDRs

| ScFv sequences | SEQ ID # | Raw amino acid sequence |
|---|---|---|
| | SEQ ID NO. 71 | CDR3 QQYSSYPYT |

TABLE 3

CAR of structure V-1

| CAR Designation V-1 | signal peptide (optional) | VH | VL | FcεRIIIγ hinge | CD8α TM | 41BB-IC | CD3ζζ CD |
|---|---|---|---|---|---|---|---|
| H8 scCAR-v1 (SEQ ID NO. 19) | SEQ ID NO. 1 | SEQ ID NO. 11 | SEQ ID NO. 12 | SEQ ID NO. 3 | SEQ ID NO. 6 | SEQ ID NO. 8 | SEQ ID NO. 9 |
| A1 scCAR-v1 (SEQ ID NO. 25) | SEQ ID NO. 1 | SEQ ID NO. 13 | SEQ ID NO. 14 | SEQ ID NO. 3 | SEQ ID NO. 6 | SEQ ID NO. 8 | SEQ ID NO. 9 |
| A2 scCAR-v1 (SEQ ID NO. 31) | SEQ ID NO. 1 | SEQ ID NO. 15 | SEQ ID NO. 16 | SEQ ID NO. 3 | SEQ ID NO. 6 | SEQ ID NO. 8 | SEQ ID NO. 9 |
| A3 scCAR-v1 (SEQ ID NO. 37) | SEQ ID NO. 1 | SEQ ID NO. 17 | SEQ ID NO. 18 | SEQ ID NO. 3 | SEQ ID NO. 6 | SEQ ID NO. 8 | SEQ ID NO. 9 |

TABLE 4

CAR of structure V-2

| CAR Designation V-2 | signal peptide (optional) | VH | VL | FcεRIIIγ hinge | 41BB-TM | 41BB-IC | CD3ζζ CD |
|---|---|---|---|---|---|---|---|
| H8 scCAR-v2 (SEQ ID NO. 20) | SEQ ID NO. 1 | SEQ ID NO. 11 | SEQ ID NO. 12 | SEQ ID NO. 3 | SEQ ID NO. 7 | SEQ ID NO. 8 | SEQ ID NO. 9 |
| A1-scCAR-v2 (SEQ ID NO. 26) | SEQ ID NO. 1 | SEQ ID NO. 13 | SEQ ID NO. 14 | SEQ ID NO. 3 | SEQ ID NO. 7 | SEQ ID NO. 8 | SEQ ID NO. 9 |
| A2 scCAR-v2 (SEQ ID NO. 32) | SEQ ID NO. 1 | SEQ ID NO. 15 | SEQ ID NO. 16 | SEQ ID NO. 3 | SEQ ID NO. 7 | SEQ ID NO. 8 | SEQ ID NO. 9 |
| A3 scCAR-v2 (SEQ ID NO. 38) | SEQ ID NO. 1 | SEQ ID NO. 17 | SEQ ID NO. 18 | SEQ ID NO. 3 | SEQ ID NO. 7 | SEQ ID NO. 8 | SEQ ID NO. 9 |

TABLE 5

CAR of structure V-3

| CAR Designation V-3 | signal peptide (optional) | VH | VL | CD8α hinge | CD8α TM | 41BB-IC | CD3ζζ CD |
|---|---|---|---|---|---|---|---|
| H8 scCAR-v3 (SEQ ID NO. 21) | SEQ ID NO. 1 | SEQ ID NO. 11 | SEQ ID NO. 12 | SEQ ID NO. 4 | SEQ ID NO. 6 | SEQ ID NO. 8 | SEQ ID NO. 9 |
| A1-scCAR-v3 (SEQ ID NO. 27) | SEQ ID NO. 1 | SEQ ID NO. 13 | SEQ ID NO. 14 | SEQ ID NO. 4 | SEQ ID NO. 6 | SEQ ID NO. 8 | SEQ ID NO. 9 |
| A2 scCAR-v3 (SEQ ID NO. 33) | SEQ ID NO. 1 | SEQ ID NO. 15 | SEQ ID NO. 16 | SEQ ID NO. 4 | SEQ ID NO. 6 | SEQ ID NO. 8 | SEQ ID NO. 9 |
| A3 scCAR-v3 (SEQ ID NO. 39) | SEQ ID NO. 1 | SEQ ID NO. 17 | SEQ ID NO. 18 | SEQ ID NO. 4 | SEQ ID NO. 6 | SEQ ID NO. 8 | SEQ ID NO. 9 |

TABLE 6

CAR of structure V-4

| CAR Designation V-4 | signal peptide (optional) | CAR Structure ||||| |
|---|---|---|---|---|---|---|---|
| | | VH | VL | CD8α hinge | 41BB-TM | 41BB-IC | CD3ζ ζ CD |
| H8 scCAR-v4 (SEQ ID NO. 22) | SEQ ID NO. 1 | SEQ ID NO. 11 | SEQ ID NO. 12 | SEQ ID NO. 4 | SEQ ID NO. 7 | SEQ ID NO. 8 | SEQ ID NO. 9 |
| A1 scCAR-v4 (SEQ ID NO. 28) | SEQ ID NO. 1 | SEQ ID NO. 13 | SEQ ID NO. 14 | SEQ ID NO. 4 | SEQ ID NO. 7 | SEQ ID NO. 8 | SEQ ID NO. 9 |
| A2 scCAR-v4 (SEQ ID NO. 34) | SEQ ID NO. 1 | SEQ ID NO. 15 | SEQ ID NO. 16 | SEQ ID NO. 4 | SEQ ID NO. 7 | SEQ ID NO. 8 | SEQ ID NO. 9 |
| A3 scCAR-v4 (SEQ ID NO. 40) | SEQ ID NO. 1 | SEQ ID NO. 17 | SEQ ID NO. 18 | SEQ ID NO. 4 | SEQ ID NO. 7 | SEQ ID NO. 8 | SEQ ID NO. 9 |

TABLE 7

CAR of structure V-5

| CAR Designation V-5 | signal peptide (optional) | CAR Structure ||||| |
|---|---|---|---|---|---|---|---|
| | | VH | VL | IgG1 hinge | CD8α TM | 41BB-IC | CD3ζ ζ CD |
| H8 scCAR-v5 (SEQ ID NO. 23) | SEQ ID NO. 1 | SEQ ID NO. 11 | SEQ ID NO. 12 | SEQ ID NO. 5 | SEQ ID NO. 6 | SEQ ID NO. 8 | SEQ ID NO. 9 |
| A1 scCAR-v5 (SEQ ID NO. 29) | SEQ ID NO. 1 | SEQ ID NO. 13 | SEQ ID NO. 14 | SEQ ID NO. 5 | SEQ ID NO. 6 | SEQ ID NO. 8 | SEQ ID NO. 9 |
| A2 scCAR-v5 (SEQ ID NO. 35) | SEQ ID NO. 1 | SEQ ID NO. 15 | SEQ ID NO. 16 | SEQ ID NO. 5 | SEQ ID NO. 6 | SEQ ID NO. 8 | SEQ ID NO. 9 |
| A3 scCAR-v5 (SEQ ID NO. 41) | SEQ ID NO. 1 | SEQ ID NO. 17 | SEQ ID NO. 18 | SEQ ID NO. 5 | SEQ ID NO. 6 | SEQ ID NO. 8 | SEQ ID NO. 9 |

TABLE 8

CAR of structure V-6

| CAR Designation V-6 | signal peptide (optional) | CAR Structure ||||| |
|---|---|---|---|---|---|---|---|
| | | VH | VL | IgG1 hinge | 41BB-TM | 41BB-IC | CD3ζ ζ CD |
| H8 scCAR-v6 (SEQ ID NO. 24) | SEQ ID NO. 1 | SEQ ID NO. 11 | SEQ ID NO. 12 | SEQ ID NO. 5 | SEQ ID NO. 7 | SEQ ID NO. 8 | SEQ ID NO. 9 |
| A1 scCAR-v6 (SEQ ID NO. 30) | SEQ ID NO. 1 | SEQ ID NO. 13 | SEQ ID NO. 14 | SEQ ID NO. 5 | SEQ ID NO. 7 | SEQ ID NO. 8 | SEQ ID NO. 9 |
| A2 scCAR-v6 (SEQ ID NO. 36) | SEQ ID NO. 1 | SEQ ID NO. 15 | SEQ ID NO. 16 | SEQ ID NO. 5 | SEQ ID NO. 7 | SEQ ID NO. 8 | SEQ ID NO. 9 |
| A3 scCAR-v6 (SEQ ID NO. 42) | SEQ ID NO. 1 | SEQ ID NO. 17 | SEQ ID NO. 18 | SEQ ID NO. 5 | SEQ ID NO. 7 | SEQ ID NO. 8 | SEQ ID NO. 9 |

DETAILED DESCRIPTION OF THE INVENTION

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

5T4 Specific Chimeric Antigen Receptors

The present invention relates to new designs of anti-5T4 chimeric antigen receptor (CAR) comprising an extracellular ligand-binding domain, a transmembrane domain and a signaling transducing domain.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. In a preferred embodiment, said extracellular ligand-binding domain comprises a single chain antibody fragment (scFv) comprising the light ($V_L$) and the heavy ($V_H$) variable fragment of a target antigen specific monoclonal anti 5T4 antibody joined by a flexible linker.

The antigen binding domain of the 5T4 CARs of the invention can be any domain that binds to the off-tissue antigen including but not limited to a monoclonal antibody, a recombinant antibody, a human antibody, a humanized antibody, and a functional fragment thereof.

By the term "recombinant antibody" as used herein, is meant an antibody or antibody fragment which is generated using recombinant DNA technology, such as, for example, an antibody or antibody fragment expressed by a bacteriophage, a yeast expression system or a mammalian cell expression system, and more especially by a T cell transduced with a viral vector comprising a nucleic acid sequence encoding CDR regions of an antibody. The term should also be construed to mean an antibody or antibody fragment which has been generated by the synthesis of a DNA molecule encoding the antibody or antibody fragment and which DNA molecule expresses an antibody or antibody fragment protein, or an amino acid sequence specifying the antibody or antibody fragment, wherein the DNA or amino acid sequence has been obtained using recombinant or synthetic DNA or amino acid sequence technology which is available and well known in the art.

By the term "monoclonal antibody" as used herein, is meant antibody produced by a laboratory-grown cell clone, either of a hybridoma or a virus-transformed lymphocyte, that is more abundant and uniform than natural antibody and is able to bind specifically to a single site on ROR1 antigen. They are monospecific antibodies that are made by identical immune cells that are all clones of a unique parent cell, in contrast to polyclonal antibodies which are made from several different immune cells. Monoclonal antibodies have monovalent affinity, in that they bind to the same epitope.

In a preferred embodiment, said extracellular ligand-binding domain comprises a single chain antibody fragment (scFv) comprising the light ($V_L$) and the heavy ($V_H$) variable fragment of a target antigen specific monoclonal 514 antibody joined by a flexible linker. Said $V_L$ and $V_H$ are preferably selected from the antibodies referred to as H8, A1, A2 and A3 as indicated in Table 2. They are preferably linked together by a flexible linker comprising for instance the sequence SEQ ID NO.10. In other words, said CARs preferentially comprise an extracellular ligand-binding domain comprising a polypeptide sequence displaying at least 90%, 95% 97% or 99% identity with an amino acid sequence selected from the group consisting of SEQ ID NO: 11 to SEQ ID NO: 18.

According to a preferred embodiment, the 5T4 specific CAR according to the present invention contains an extracellular ligand-binding domain, wherein said VH and VL have at least 80%, preferably at least 90%, more preferably at least 95%, and even more preferably at least 99% sequence identity respectively with SEQ ID NO:13 (A1-VH) and SEQ ID NO:14 (A1-VL).

According to another preferred embodiment, the 5T4 specific CAR according to the present invention contains an extracellular ligand-binding domain, wherein said VH and VL have at least 80%, preferably at least 90%, more preferably at least 95%, and even more preferably at least 99% sequence identity respectively with SEQ ID NO:15 (A2-VH) and SEQ ID NO:16 (A2-VL).

According to another preferred embodiment, the 5T4 specific CAR according to the present invention contains an extracellular ligand-binding domain, wherein said VH and VL have at least 80%, preferably at least 90%, more preferably at least 95%, and even more preferably at least 99% sequence identity respectively with SEQ ID NO:17 (A3-VH) and SEQ ID NO:18 (A3-VL).

According to another preferred embodiment, the 5T4 specific CAR according to the present invention contains an extracellular ligand-binding domain, wherein said VH and VL have at least 80%, preferably at least 90%, more preferably at least 95%, and even more preferably at least 99% sequence identity respectively with SEQ ID NO:11 (H18-VH) and SEQ ID NO:12 (H18-VL).

The present invention discloses a 5T4 specific chimeric antigen receptor (5T4 CAR) as above, wherein said extra cellular ligand binding-domain comprises VH and VL chains which are humanized.

By the term "humanized antibody" as used herein, is meant the polypeptides include a humanized heavy chain variable region and a humanized light chain variable region. For example, the polypeptides may include the framework (FR) regions of the light and heavy chain variable regions of a human antibody, while retaining substantially the antigen-binding specificity of a parental monoclonal antibody. The humanized heavy chain variable region and/or the humanized light chain variable region are at least about 87% humanized, at least about 90% humanized, at least about 95% humanized, at least about 98% humanized, or at least about 100% humanized, excluding the complementary-determining regions (CDRs). The antigen-binding polypeptides molecules may be derived from monoclonal antibody donors (e.g., mouse monoclonal antibody donors) and may include CDRs from the monoclonal antibodies (e.g., mouse monoclonal CDRs).

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, each of which is incorporated herein in its entirety by reference. Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and which is incorporated herein by reference in their entireties).

According to a preferred embodiment, the A 5T4 specific CAR of the present invention comprises VH and VL chains which have at least 80%, preferably 90%, more preferably wherein said extra cellular ligand binding-domain comprising:
- a VH chain comprising the CDRs from the mouse monoclonal antibody H8 of SEQ ID NO. 48 (CDR1), SEQ ID NO.49 (CDR2) and SEQ ID NO.50 (CDR3), and a VL chain comprising the CDRs from the mouse monoclonal antibody H18 of NO. 51 (CDR1), SEQ ID NO.52 (CDR2) and SEQ ID NO:53 (CDR3), or;
- a VH chain comprising the CDRs from the mouse monoclonal antibody A1 of SEQ ID NO. 54 (CDR1), SEQ ID NO.55 (CDR2) and SEQ ID NO.56 (CDR3), and a VL chain comprising the CDRs from the mouse monoclonal antibody A1 of NO. 57 (CDR1), SEQ ID NO.58 (CDR2) and SEQ ID NO:59 (CDR3), or;
- a VH chain comprising the CDRs from the mouse monoclonal antibody A2 of SEQ ID NO. 61 (CDR1), SEQ ID NO.61 (CDR2) and SEQ ID NO.63 (CDR3), and a VL chain comprising the CDRs from the mouse monoclonal antibody A2 of NO. 64 (CD1), SEQ ID NO.65 (CD2) and SEQ ID NO:65 (CDR3), or;
- a VH chain comprising the CDRs from the mouse monoclonal antibody A3 of SEQ ID NO. 66 (CDR1), SEQ ID NO.67 (CDR2) and SEQ ID NO.68 (CDR3), and a VL chain comprising the CDRs from the mouse monoclonal antibody A3 of NO. 69 (CDR1), SEQ ID NO.70 (CDR2) and SEQ ID NO:71 (CDR3).

Table 2 shows the sequences VH and VL chains corresponding to the H8, A1, A2 and A3 anti-5T4 antibodies and of their respective CDRs.

The signal transducing domain or intracellular signaling domain of a CAR according to the present invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the CAR is expressed. For example, the effector function of a T cell can be a cytolytic activity or helper activity including the secretion of cytokines. Thus, the term "signal transducing domain" refers to the portion of a protein which transduces the effector signal function signal and directs the cell to perform a specialized function.

Preferred examples of signal transducing domain for use in a CAR can be the cytoplasmic sequences of the T cell receptor and co-receptors that act in concert to initiate signal transduction following antigen receptor engagement, as well as any derivate or variant of these sequences and any synthetic sequence that has the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non-limiting examples those derived from TCRzeta, FcRgamma, FcRbeta, FcRepsilon, CD3gamma, CD3delta, CD3epsilon, CD5, CD22, CD79a, CD79b and CD66d. In a preferred embodiment, the signaling transducing domain of the CAR can comprise the CD3zeta signaling domain which has amino acid sequence with at least 70%, preferably at least 80%, more preferably at least 90%, 95% 97% or 99% sequence identity with amino acid sequence selected from the group consisting of (SEQ ID NO: 9).

In particular embodiment the signal transduction domain of the CAR of the present invention comprises a co-stimulatory signal molecule. A co-stimulatory molecule is a cell surface molecule other than an antigen receptor or their ligands that is required for an efficient immune response. "Co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83.

A "co-stimulatory molecule" refers to the cognate binding partner on a T-cell that specifically binds with a co-stimulatory ligand, thereby mediating a co-stimulatory response by the cell, such as, but not limited to proliferation. Co-stimulatory molecules include, but are not limited to, an MHC class I molecule, BILA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

In a preferred embodiment, the signal transduction domain of the CAR of the present invention comprises a part of co-stimulatory signal molecule selected from the group consisting of fragment of 4-1BB (GenBank: AAA53133.) and CD28 (NP_006130.1). In particular the signal transduction domain of the CAR of the present invention comprises amino acid sequence which comprises at least 70%, preferably at least 80%, more preferably at least 90%, 95% 97% or 99% sequence identity with amino acid sequence selected from the group consisting of SEQ ID NO: 8.

A CAR according to the present invention is expressed on the surface membrane of the cell. Thus, such CAR further comprises a transmembrane domain. The distinguishing features of appropriate transmembrane domains comprise the ability to be expressed at the surface of a cell, preferably in the present invention an immune cell, in particular lymphocyte cells or Natural killer (NK) cells, and to interact together for directing cellular response of immune cell against a predefined target cell. The transmembrane domain can be derived either from a natural or from a synthetic source. The transmembrane domain can be derived from any membrane-bound or transmembrane protein. As non-limiting examples, the transmembrane polypeptide can be a subunit of the T-cell receptor such as α, β, γ or ζ polypeptide constituting CD3 complex, IL2 receptor p55 (α chain), p75 (β chain) or γ chain, subunit chain of Fc receptors, in particular Fcγ receptor III or CD proteins. Alternatively the transmembrane domain can be synthetic and can comprise predominantly hydrophobic residues such as leucine and valine. In a preferred embodiment said transmembrane domain is derived from the human CD8 alpha chain (e.g. NP_001139345.1) The transmembrane domain can further comprise a hinge region between said extracellular ligand-binding domain and said transmembrane domain. The term "hinge region" used herein generally means any oligo- or polypeptide that functions to link the transmembrane domain to the extracellular ligand-binding domain. In particular, hinge region are used to provide more flexibility and accessibility for the extracellular ligand-binding domain. A hinge region may comprise up to 300 amino acids, preferably 10 to 100 amino acids and most preferably 25 to 50 amino acids. Hinge region may be derived from all or part of naturally occurring molecules, such as from all or part of the extracellular region of CD8, CD4 or CD28, or from all or part of an antibody constant region. Alternatively the hinge region may be a synthetic sequence that corresponds to a naturally occurring hinge sequence, or may be an entirely synthetic hinge sequence. In a preferred embodiment said hinge domain comprises a part of human CD8 alpha chain, FcγRIIIα receptor or IgG1 respectively referred to in this specification as SEQ ID NO. 3, SEQ ID NO. 4 and SEQ ID NO.5, or hinge polypeptides which display preferably at least 80%, more preferably at least 90%, 95% 97% or 99% sequence identity with these polypeptides.

A car according to the invention generally further comprises a transmembrane domain (TM) more particularly selected from CD8a and 4-1BB, showing identity with the polypeptides of SEQ ID NO. 6 or 7.

Downregulation or mutation of target antigens is commonly observed in cancer cells, creating antigen-loss escape variants. Thus, to offset tumor escape and render immune cell more specific to target, the 5T4 specific CAR according to the invention can comprise another extracellular ligand-binding domains, to simultaneously bind different elements in target thereby augmenting immune cell activation and function. In one embodiment, the extracellular ligand-binding domains can be placed in tandem on the same transmembrane polypeptide, and optionally can be separated by a linker. In another embodiment, said different extracellular ligand-binding domains can be placed on different transmembrane polypeptides composing the CAR. In another embodiment, the present invention relates to a population of CARs comprising each one different extracellular ligand binding domains. In a particular, the present invention relates to a method of engineering immune cells comprising providing an immune cell and expressing at the surface of said cell a population of CAR each one comprising different extracellular ligand binding domains. In another particular embodiment, the present invention relates to a method of engineering an immune cell comprising providing an immune cell and introducing into said cell polynucleotides encoding polypeptides composing a population of CAR each one comprising different extracellular ligand binding domains. By population of CARs, it is meant at least two, three, four, five, six or more CARs each one comprising different extracellular ligand binding domains. The different extracellular ligand binding domains according to the present invention can preferably simultaneously bind different elements in target thereby augmenting immune cell activation and function. The present invention also relates to an isolated immune cell which comprises a population of CARs each one comprising different extracellular ligand binding domains.

Figure 2:
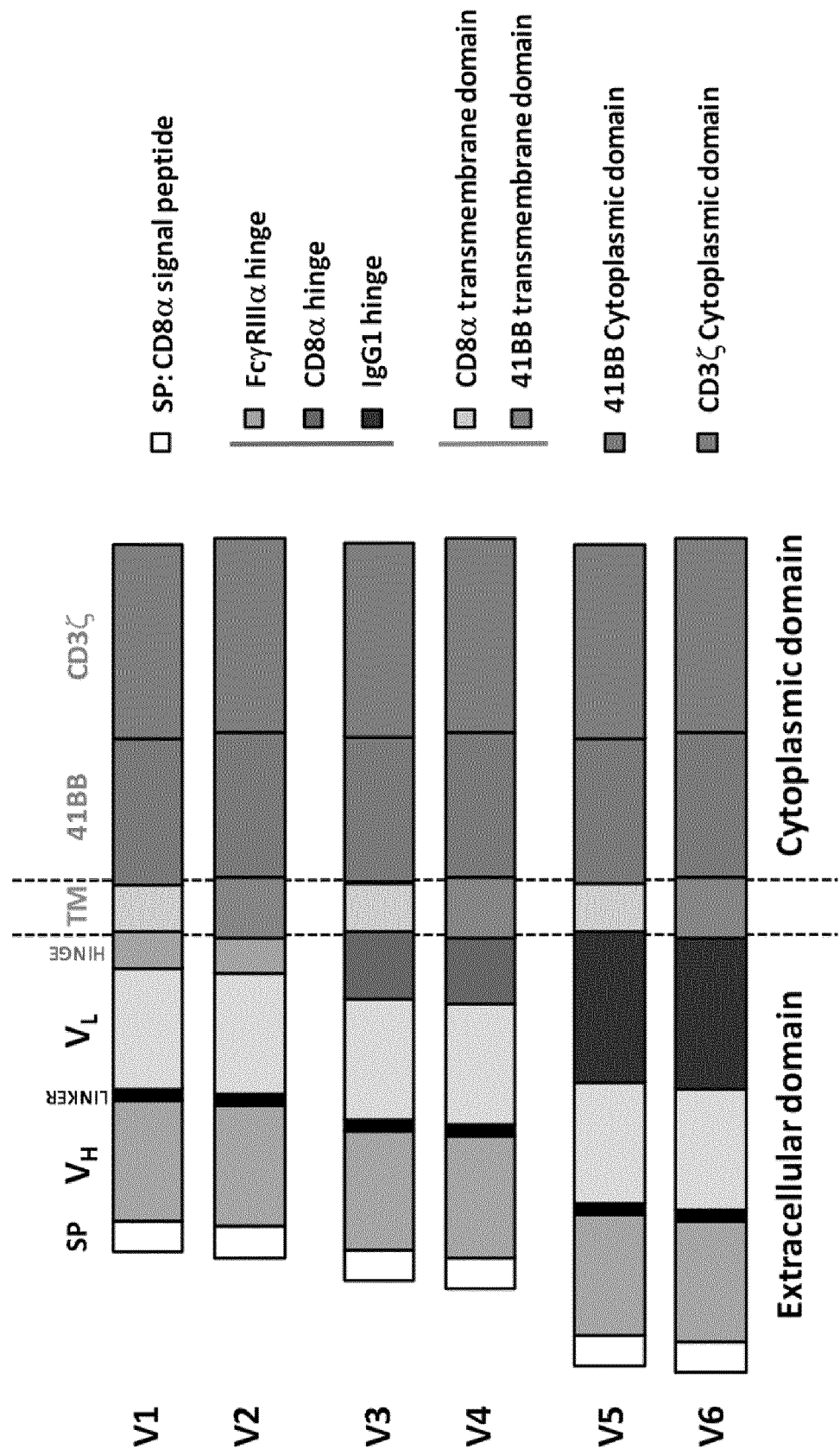
FIG. 2: schematic representation of the different CAR Architecture (V1 to V6).

According to a preferred embodiment, the 5T4 specific CAR according to the invention has a structure V3 as displayed in FIG. 2, thus comprising a CD8a hinge and a CD8a transmembrane domain.

According to another preferred embodiment, the 5T4 specific CAR according to the invention has a structure V5 as displayed in FIG. 2, thus comprising an IgG1 hinge and a CD8a transmembrane domain.

According to another preferred embodiment, the 5T4 specific CAR according to the invention has a structure V1 as displayed in FIG. 2, thus comprising a FcγRIIIα hinge and CD8a transmembrane domain.

Polynucleotides, Vectors:

The present invention also relates to polynucleotides, vectors encoding the above described CAR according to the invention.

The polynucleotide may consist in an expression cassette or expression vector (e.g. a plasmid for introduction into a bacterial host cell, or a viral vector such as a baculovirus vector for transfection of an insect host cell, or a plasmid or viral vector such as a lentivirus for transfection of a mammalian host cell).

In a particular embodiment, the different nucleic acid sequences can be included in one polynucleotide or vector which comprises a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see (Donnelly and Elliott 2001; Atkins, Wills et al. 2007; Doronina, Wu et al. 2008)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA.

To direct transmembrane polypeptide into the secretory pathway of a host cell, a secretory signal sequence (also known as a leader sequence, prepro sequence or pre sequence) is provided in polynucleotide sequence or vector sequence. The secretory signal sequence is operably linked to the transmembrane nucleic acid sequence, i.e., the two sequences are joined in the correct reading frame and positioned to direct the newly synthesized polypeptide into the secretory pathway of the host cell. Secretory signal sequences are commonly positioned 5' to the nucleic acid sequence encoding the polypeptide of interest, although certain secretory signal sequences may be positioned elsewhere in the nucleic acid sequence of interest (see, e.g., Welch et al., U.S. Pat. No. 5,037,743; Holland et al., U.S. Pat. No. 5,143,830). In a preferred embodiment the signal peptide comprises the amino acid sequence SEQ ID NO: 1 and 2.

Those skilled in the art will recognize that, in view of the degeneracy of the genetic code, considerable sequence variation is possible among these polynucleotide molecules. Preferably, the nucleic acid sequences of the present invention are codon-optimized for expression in mammalian cells, preferably for expression in human cells. Codon-optimization refers to the exchange in a sequence of interest of codons that are generally rare in highly expressed genes of a given species by codons that are generally frequent in highly expressed genes of such species, such codons encoding the amino acids as the codons that are being exchanged.

Methods of Engineering Immune Cells Endowed with CARs:

The present invention encompasses the method of preparing immune cells for immunotherapy comprising introducing ex-vivo into said immune cells the polynucleotides or vectors encoding one of the 5T4 CAR as previously described.

In a preferred embodiment, said polynucleotides are included in lentiviral vectors in view of being stably expressed in the immune cells.

According to further embodiments, said method further comprises the step of genetically modifying said cell to make them more suitable for allogeneic transplantation.

According to a first aspect, the immune cell can be made allogeneic, for instance, by inactivating at least one gene expressing one or more component of T-cell receptor (TCR) as described in WO 2013/176915, which can be combined with the inactivation of a gene encoding or regulating HLA or β2m protein expression. Accordingly the risk of graft versus host syndrome and graft rejection is significantly reduced.

According to another aspect, the immune cells can be further genetically engineered to improve their resistance to immunosuppressive drugs or chemotherapy treatments, which are used as standard care for treating 514 positive malignant cells. For instance, CD52 and glucocorticoid receptors (GR), which are drug targets of Campath (alemtuzumab) and glucocorticoids treatments, can be inactivated to make the cells resistant to these treatments and give them a competitive advantage over patient's own T-cells not endowed with specific 5T4 CARs. Expression of CD3 gene can also be suppressed or reduced to confer resistance to Teplizumab, which is another immune suppressive drug. Expression of HPRT can also be suppressed or reduced according to the invention to confer resistance to 6-thioguanine, a cytostatic agent commonly used in chemotherapy especially for the treatment of acute lymphoblasic leukemia.

According to further aspect of the invention, the immune cells can be further manipulated to make them more active or limit exhaustion, by inactivating genes encoding proteins that act as "immune checkpoints" that act as regulators of T-cells activation, such as PDCD1 or CTLA-4. Examples of genes, which expression could be reduced or suppressed are indicated in Table 9.

TABLE 9

List of genes encoding immune checkpoint proteins.

| | Pathway | Genes that can be inactivated In the pathway |
|---|---|---|
| Co-inhibitory receptors | CTLA4 (CD152) | CTLA4, PPP2CA, PPP2CB, PTPN6, PTPN22 |
| | PDCD1 (PD-1, CD279) | PDCD1 |
| | CD223 (lag3) | LAG3 |
| | HAVCR2 (tim3) | HAVCR2 |
| | BTLA(cd272) | BTLA |
| | CD160(by55) | CD160 |
| | IgSF family | TIGIT |
| | | CD96 |
| | | CRTAM |
| | LAIR1(cd305) | LAIR1 |
| | SIGLECs | SIGLEC7 |
| | | SIGLEC9 |
| | CD244(2b4) | CD244 |
| Death receptors | TRAIL | TNFRSF10B, TNFRSF10A, CASP8, CASP10, CASP3, CASP6, CASP7 |
| | FAS | FADD, FAS |
| Cytokine signalling | TGF-beta signaling | TGFBRII, TGFBRI, SMAD2, SMAD3, SMAD4, SMAD10, SKI, SKIL, TGIF1 |
| | IL10 signalling | IL10RA, IL10RB, HMOX2 |
| | IL6 signalling | IL6R, IL6ST |
| Prevention of TCR signalling | | CSK, PAG1 |
| | | SIT1 |
| Induced Treg | induced Treg | FOXP3 |
| Transcription | transcription factors | PRDM1 (=blimp1, heterozygotes mice |

TABLE 9-continued

List of genes encoding immune checkpoint proteins.

| Pathway | | Genes that can be inactivated In the pathway |
|---|---|---|
| factors controlling exhaustion | controlling exhaustion | control chronic viral infection better than wt or conditional KO) BATF |
| Hypoxia mediated tolerance | iNOS induced guanylated cyclase | GUCY1A2, GUCY1A3, GUCY1B2, GUCY1B3 |

In a preferred embodiment said method of further engineering the immune cells involves introducing into said T cells polynucleotides, in particular mRNAs, encoding specific rare-cutting endonuclease to selectively inactivate the genes, as those mentioned above, by DNA cleavage. In a more preferred embodiment said rare-cutting endonucleases are TALE-nucleases or Cas9 endonuclease. TAL-nucleases have so far proven higher specificity and cleavage efficiency over the other types of rare-cutting endonucleases, making them the endonucleases of choice for producing of the engineered immune cells on a large scale with a constant turn-over.

Delivery Methods

The different methods described above involve introducing CAR into a cell. As non-limiting example, said CAR can be introduced as transgenes encoded by one plasmid vector. Said plasmid vector can also contain a selection marker which provides for identification and/or selection of cells which received said vector.

Polypeptides may be synthesized in situ in the cell as a result of the introduction of polynucleotides encoding said polypeptides into the cell. Alternatively, said polypeptides could be produced outside the cell and then introduced thereto. Methods for introducing a polynucleotide construct into cells are known in the art and including as non-limiting examples stable transformation methods wherein the polynucleotide construct is integrated into the genome of the cell, transient transformation methods wherein the polynucleotide construct is not integrated into the genome of the cell and virus mediated methods. Said polynucleotides may be introduced into a cell by for example, recombinant viral vectors (e.g. retroviruses, adenoviruses), liposome and the like. For example, transient transformation methods include for example microinjection, electroporation or particle bombardment. Said polynucleotides may be included in vectors, more particularly plasmids or virus, in view of being expressed in cells.

Engineered Immune Cells

The present invention also relates to isolated cells or cell lines susceptible to be obtained by said method to engineer cells. In particular said isolated cell comprises at least one CAR as described above. In another embodiment, said isolated cell comprises a population of CARs each one comprising different extracellular ligand binding domains. In particular, said isolated cell comprises exogenous polynucleotide sequence encoding CAR. Genetically modified immune cells of the present invention are activated and proliferate independently of antigen binding mechanisms.

In the scope of the present invention is also encompassed an isolated immune cell, preferably a T-cell obtained according to any one of the methods previously described. Said immune cell refers to a cell of hematopoietic origin functionally involved in the initiation and/or execution of innate and/or adaptative immune response. Said immune cell according to the present invention can be derived from a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. Said isolated cell can also be a dendritic cell, killer dendritic cell, a mast cell, a NK-cell, a B-cell or a T-cell selected from the group consisting of inflammatory T-lymphocytes, cytotoxic T-lymphocytes, regulatory T-lymphocytes or helper T-lymphocytes. In another embodiment, said cell can be derived from the group consisting of CD4+T-lymphocytes and CD8+T-lymphocytes. Prior to expansion and genetic modification of the cells of the invention, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available and known to those skilled in the art, may be used. In another embodiment, said cell can be derived from a healthy donor, from a patient diagnosed with cancer or from a patient diagnosed with an infection. In another embodiment, said cell is part of a mixed population of cells which present different phenotypic characteristics. In the scope of the present invention is also encompassed a cell line obtained from a transformed T-cell according to the method previously described. Modified cells resistant to an immunosuppressive treatment and susceptible to be obtained by the previous method are encompassed in the scope of the present invention.

As a preferred embodiment, the present invention provides T-cells or a population of T-cells endowed with a 5T4 CAR as described above, that do not express functional TCR and that a reactive towards 5T4 positive cells, for their allogeneic transplantation into patients.

Activation and Expansion of T Cells

Whether prior to or after genetic modification of the T cells, even if the genetically modified immune cells of the present invention are activated and proliferate independently of antigen binding mechanisms, the immune cells, particularly T-cells of the present invention can be further activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo.

Generally, the T cells of the invention are expanded by contact with an agent that stimulates a CD3 TCR complex and a co-stimulatory molecule on the surface of the T cells to create an activation signal for the T-cell. For example, chemicals such as calcium ionophore A23187, phorbol 12-myristate 13-acetate (PMA), or mitogenic lectins like phytohemagglutinin (PHA) can be used to create an activation signal for the T-cell.

As non-limiting examples, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, 1L-4, 1L-7, GM-CSF, -10, -2, 1L-15, TGFp, and TNF- or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% C02). T cells that have been exposed to varied stimulation times may exhibit different characteristics In another particular embodiment, said cells can be expanded by co-culturing with tissue or cells. Said cells can also be expanded in vivo, for example in the subject's blood after administrating said cell into the subject.

Therapeutic Applications

In another embodiment, isolated cell obtained by the different methods or cell line derived from said isolated cell as previously described can be used as a medicament. In another embodiment, said medicament can be used for treating cancer, particularly for the treatment of carcinoma and leukemia in a patient in need thereof. In another embodiment, said isolated cell according to the invention or cell line derived from said isolated cell can be used in the manufacture of a medicament for treatment of a cancer in a patient in need thereof.

In another aspect, the present invention relies on methods for treating patients in need thereof, said method comprising at least one of the following steps:

(a) providing an immune-cell obtainable by any one of the methods previously described;

(b) Administrating said transformed immune cells to said patient,

On one embodiment, said T cells of the invention can undergo robust in vivo T cell expansion and can persist for an extended amount of time.

Said treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

Cells that can be used with the disclosed methods are described in the previous section. Said treatment can be used to treat patients diagnosed wherein a pre-malignant or malignant cancer condition characterized by 5T4-expressing cells, especially by an overabundance of 5T4-expressing cells. Such conditions are found in solid cancers or in hematologic cancers, such as childhood pre-B acute lymphoblastic leukemia.

Solid tumors can be gastric tumors, colorectal tumors, prostate tumors, breast tumors, lung tumors, renal tumors or ovarian tumors.

More specifically, such treatment may be useful for progressive hormone refractory prostate cancer in combination or not of drug(s) such as docetaxel or granulocyte macrophage-colony stimulating factor (GM-CSF).

Also, the engineered T cell of the invention may be used for treating advanced solid tumors such as non-small cell lung cancer, renal clear cell carcinoma or pancreatic cancer, in conjunction with other drug(s) such as interleukin-2 (IL-2), docetaxel or pemetrexed/cisplatin.

Moreover, the engineered T cell of the invention may be used for treating prostate cancer with or without cyclophosphamide.

Lymphoproliferative disorder can be leukemia, in particular childhood pre-B acute lymphoblastic leukemia.

Cancers that may be treated may comprise nonsolid tumors (such as hematological tumors, including but not limited to pre-B ALL (pedriatic indication), adult ALL, mantle cell lymphoma, diffuse large B-cell lymphoma and the like. Types of cancers to be treated with the CARs of the invention include, but are not limited leukemia or lymphoid malignancies. Adult tumors/cancers and pediatric tumors/cancers are also included.

Also, solid tumors such as stomach, colon, and ovarian tumors can be treated by the CARs of the invention The treatment with the engineered immune cells according to the invention may be in combination with one or more therapies against cancer selected from the group of antibodies therapy, chemotherapy, cytokines therapy, dendritic cell therapy, gene therapy, hormone therapy, laser light therapy and radiation therapy.

According to a preferred embodiment of the invention, said treatment can be administrated into patients undergoing an immunosuppressive treatment. Indeed, the present invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the T-cells according to the invention within the patient.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administered will be dependent upon the age, health and weight of the recipient, kind of concurrent treatment, if any, frequency of treatment and the nature of the effect desired.

In another embodiment, said effective amount of cells or composition comprising those cells are administered parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Henderson, Naya et al. 1991; Liu, Albers et al. 1992; Bierer, Hollander et al. 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

Other Definitions

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

"As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

By chimeric antigen receptor (CAR) is intended molecules that combine a binding domain against a component present on the target cell, for example an antibody-based specificity for a desired antigen (e.g., tumor antigen) with a T cell receptor-activating intracellular domain to generate a chimeric protein that exhibits a specific anti-target cellular immune activity. Generally, CAR consists of an extracellular single chain antibody (scFvFc), fused to the intracellular signaling domain of the T cell antigen receptor complex zeta chain (scFvFc:ζ) and have the ability, when expressed in T cells, to redirect antigen recognition based on the monoclonal antibody's specificity. CAR may sometimes comprise multiple transmembrane polypeptides (multi-chain CARs) as described in WO2014039523. One example of CAR used in the present invention is a CAR directing against 5T4 antigen and can comprise as non-limiting example the amino acid sequences: SEQ ID NO: 19 to 42.

The term "endonuclease" refers to any wild-type or variant enzyme capable of catalyzing the hydrolysis (cleavage) of bonds between nucleic acids within a DNA or RNA molecule, preferably a DNA molecule. Endonucleases do not cleave the DNA or RNA molecule irrespective of its sequence, but recognize and cleave the DNA or RNA molecule at specific polynucleotide sequences, further referred to as "target sequences" or "target sites". Endonucleases can be classified as rare-cutting endonucleases when having typically a polynucleotide recognition site greater than 12 base pairs (bp) in length, more preferably of 14-55 bp. Rare-cutting endonucleases significantly increase HR by inducing DNA double-strand breaks (DSBs) at a defined locus (Perrin, Buckle et al. 1993; Rouet, Smih et al. 1994; Choulika, Perrin et al. 1995; Pingoud and Silva 2007). Rare-cutting endonucleases can for example be a homing endonuclease (Paques and Duchateau 2007), a chimeric Zinc-Finger nuclease (ZFN) resulting from the fusion of engineered zinc-finger domains with the catalytic domain of a restriction enzyme such as FokI (Porteus and Carroll 2005), a Cas9 endonuclease from CRISPR system (Gasiunas, Barrangou et al. 2012; Jinek, Chylinski et al. 2012; Cong, Ran et al. 2013; Mali, Yang et al. 2013) or a chemical endonuclease (Eisenschmidt, Lanio et al. 2005; Arimondo, Thomas et al. 2006). In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of orthophenanthroline, a DNA cleaving molecule, and triplex-forming oligonucleotides (TFOs), known to bind specific DNA sequences (Kalish and Glazer 2005). Such chemical endonucleases are comprised in the term "endonuclease" according to the present invention.

By a "TALE-nuclease" (TALEN) is intended a fusion protein consisting of a nucleic acid-binding domain typically derived from a Transcription Activator Like Effector (TALE) and one nuclease catalytic domain to cleave a nucleic acid target sequence. The catalytic domain is preferably a nuclease domain and more preferably a domain having endonuclease activity, like for instance I-TevI, ColE7, NucA and Fok-I. In a particular embodiment, the TALE domain can be fused to a meganuclease like for instance 1-CreI and 1-OnuI or functional variant thereof. In a more preferred embodiment, said nuclease is a monomeric TALE-Nuclease. A monomeric TALE-Nuclease is a TALE-Nuclease that does not require dimerization for specific recognition and cleavage, such as the fusions of engineered TAL repeats with the catalytic domain of I-TevI described in WO2012138927. Transcription Activator like Effector (TALE) are proteins from the bacterial species *Xanthomonas* comprise a plurality of repeated sequences, each repeat comprising di-residues in position 12 and 13 (RVD) that are specific to each nucleotide base of the nucleic acid targeted sequence. Binding domains with similar modular base-per-base nucleic acid binding properties (MBBBD) can also be derived from new modular proteins recently discovered by the applicant in a different bacterial species. The new modular proteins have the advantage of displaying more sequence variability than TAL repeats. Preferably, RVDs associated with recognition of the different nucleotides are HD for recognizing C, NG for recognizing T, NI for recognizing A, NN for recognizing G or A, NS for recognizing A, C, G or T, HG for recognizing T, IG for recognizing T, NK for recognizing G, HA for recognizing C, ND for recognizing C, HI for recognizing C, HN for recognizing G, NA for recognizing G, SN for recognizing G or A and YG for recognizing T, TL for recognizing A, VT for recognizing A or G and SW for recognizing A. In another embodiment, critical amino acids 12 and 13 can be mutated towards other amino acid residues in order to modulate their specificity towards nucleotides A, T, C and G and in particular to enhance this specificity. TALE-nuclease have been already described and used to stimulate gene targeting and gene modifications (Boch, Scholze et al. 2009; Moscou and Bogdanove 2009; Christian, Cermak et al. 2010; Li, Huang et al. 2011). Custom-made TAL-nucleases are commercially available under the trade name TALEN™ (Cellectis, 8 rue de la Croix Jarry, 75013 Paris, France).

The rare-cutting endonuclease according to the present invention can also be a Cas9 endonuclease. Recently, a new genome engineering tool has been developed based on the RNA-guided Cas9 nuclease (Gasiunas, Barrangou et al. 2012; Jinek, Chylinski et al. 2012; Cong, Ran et al. 2013; Mali, Yang et al. 2013) from the type II prokaryotic CRISPR (Clustered Regularly Interspaced Short palindromic Repeats) adaptive immune system (see for review (Sorek, Lawrence et al. 2013)). The CRISPR Associated (Cas) system was first discovered in bacteria and functions as a defense against foreign DNA, either viral or plasmid. CRISPR-mediated genome engineering first proceeds by the selection of target sequence often flanked by a short sequence motif, referred as the protospacer adjacent motif (PAM). Following target sequence selection, a specific crRNA, complementary to this target sequence is engineered. Trans-activating crRNA (tracrRNA) required in the CRISPR type II systems paired to the crRNA and bound to the provided Cas9 protein. Cas9 acts as a molecular anchor facilitating the base pairing of tracRNA with cRNA (Deltcheva, Chylinski et al. 2011). In this ternary complex, the dual tracrRNA:crRNA structure acts as guide RNA that directs the endonuclease Cas9 to the cognate target sequence. Target recognition by the Cas9-tracrRNA:crRNA complex is initiated by scanning the target sequence for homology between the target sequence and the crRNA. In addition to the target sequence-crRNA complementarity, DNA targeting requires the presence of a short motif adjacent to the protospacer (protospacer adjacent motif—PAM). Following pairing between the dual-RNA and the target sequence, Cas9 subsequently introduces a blunt double strand break 3 bases upstream of the PAM motif (Garneau, Dupuis et al. 2010).

Rare-cutting endonuclease can be a homing endonuclease, also known under the name of meganuclease. Such homing endonucleases are well-known to the art (Stoddard 2005). Homing endonucleases recognize a DNA target sequence and generate a single- or double-strand break. Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG endonuclease, to a HNH endonuclease, or to a GIY-YIG endonuclease. Preferred homing endonuclease according to the present invention can be an I-CreI variant.

By "delivery vector" or "delivery vectors" is intended any delivery vector which can be used in the present invention to put into cell contact (i.e "contacting") or deliver inside cells or subcellular compartments (i.e "introducing") agents/chemicals and molecules (proteins or nucleic acids) needed in the present invention.

It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By "delivery vector" or "delivery vectors" is also intended delivery methods to perform transfection.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non-chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e. g. adenoassociated viruses), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomega-lovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as nonlimiting example, that are able to integrate the genome of a target cell. At the opposite by "non-integrative lentiviral vectors (or NILV)" is meant efficient gene delivery vectors that do not integrate the genome of a target cell through the action of the virus integrase.

Delivery vectors and vectors can be associated or combined with any cellular permeabilization techniques such as sonoporation or electroporation or derivatives of these techniques.

By cell or cells is intended any eukaryotic living cells, primary cells and cell lines derived from these organisms for in vitro cultures.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

As non-limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells.

All these cell lines can be modified by the method of the present invention to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

by "mutation" is intended the substitution, deletion, insertion of up to one, two, three, four, five, six, seven, eight, nine, ten, eleven, twelve, thirteen, fourteen, fifteen, twenty, twenty five, thirty, fourty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

by "variant(s)", it is intended a repeat variant, a variant, a DNA binding variant, a TALE-nuclease variant, a polypeptide variant obtained by mutation or replacement of at least one residue in the amino acid sequence of the parent molecule.

by "functional variant" is intended a catalytically active mutant of a protein or a protein domain; such mutant may have the same activity compared to its parent protein or protein domain or additional properties, or higher or lower activity.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

"signal-transducing domain" or "co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory igand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a Tcell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor.

A "co-stimulatory signal" as used herein refers to a signal, which in combination with primary signal, such as TCR/CD3 ligation, leads to T cell proliferation and/or upregulation or downregulation of key molecules.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. Thus examples of cell surface markers that may act as ligands include those associated with viral, bacterial and parasitic infections, autoimmune disease and cancer cells.

The term "subject" or "patient" as used herein includes all members of the animal kingdom including non-human primates and humans.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Materials and Methods
Primary Cells
Peripheral blood mononuclear cells were isolated by density gradient centrifugation from buffy coats from healthy volunteer donors (Etablissement Francais du Sang). T lymphocytes were then purified using the EasySep human T cell enrichment kit (Stemcell Technologies), and activated with Dynabeads Human T-Activator CD3/CD28 (Life Technologies) in X-vivo 15 medium (Lonza) supplemented with 20 ng/ml IL-2 (Miltenyi) and 5% human AB serum (Seralab).

Cell Lines
The HCT116, MCF-7, SK-MEL-28 and Daudi cell lines were obtained from the American Type Culture Collection. HCT116 cells were cultured in McCoy supplemented with 10% heat-inactivated FCS, 2 mmol/L L-glutamine and 100 units/ml penicillin, and 100 µg/mL streptomycin. MCF-7 cells were cultured in DMEM supplemented with 10% heat-inactivated FCS, 2 mmol/L L-glutamine and 100 units/ml penicillin, and 100 µg/mL streptomycin and 0.01 mg/ml human insulin. SK-MEL-28 cells were cultured in MEM supplemented with 10% heat-inactivated FCS, 2 mmol/L L-glutamine and 100 units/ml penicillin, and 100 µg/mL streptomycin. Daudi cells were cultured in RPMI 1640 supplemented with 10% heat-inactivated FCS, 2 mmol/L L-glutamine and 100 units/ml penicillin, and 100 µg/mL streptomycin.

Synthesis and Cloning of scCARs Coding Sequences
The DNA sequences encoding the scCARs were synthesized by GenScript and cloned in a plasmid containing the T7 promoter for the in vitro synthesis of CAR mRNA.

In Vitro Synthesis of CAR mRNA
mRNA encoding the scCARs were synthesized using as templates linearized plasmids in which the sequence encoding the CARs is under the control of the T7 promoter. In vitro transcription and polyadenylation were done using the mMessage mMachine T7 Ultra kit (Life technologies) according to the manufacturer's instructions. RNAs were purified with RNeasy columns (Qiagen), eluted in cytoporation medium T (Harvard Apparatus), and quantified by measuring absorbance at 260 nm using a Nanodrop ND-1000 spectrophotometer. Quality of the RNA was verified on a denaturing formaldehyde/MOPS agarose gel.

RNA Electroporation of T Cells

After a period of 11-12 days of activation, T lymphocytes were transfected by electrotransfer of messenger RNA using an AgilePulse MAX system (Harvard Apparatus). Following removal of activation beads, cells were pelleted, resuspended in cytoporation medium T at $25 \times 10^6$ cells/ml. $5 \times 10^6$ cells were mixed with 15 µg of the mRNA encoding the scCAR into a 0.4 cm cuvette. The electroporation consisted of two 0.1 ms pulses at 1200 V followed by four 0.2 ms pulses at 130V. Following electroporation, cells were diluted into culture medium and incubated at 37° C./5% $CO_2$.

Degranulation Assay

A batch of $5 \times 10^4$ T cells were co-cultured with $5 \times 10^4$ 5 T4-positive (MCF7 or HCT116) or -negative cells (Daudi) in 0.1 ml per well in a 96-well plate. APC-labeled anti-CD107a (BD Biosciences) was added at the beginning of the co-culture in addition to 1 µg/ml of anti-CD49d (BD Biosciences), 1 µg/ml of anti-CD28 (Miltenyi), and 1× Monensin solution (eBioscience). After a 6 h incubation, the cells were stained with a fixable viability dye (eBioscience) and vioblue-labeled anti-CD8 (Miltenyi) and analyzed using the MACSQuant flow cytometer (Miltenyi). Degranulating cytotoxic T cells correspond to CD8+CD107a+ cells.

Cytotoxicity Assay

5T4-positive and -negative cells were respectively labeled with CellTrace CFSE and CellTrace Violet. Un batch of $2 \times 10^4$ 5 T4-positive cells (MCF7 or HCT116) were co-cultured with $2 \times 10^4$ 5 T4-negative cells (SKMEL28) with $4 \times 10^5$ T cells in 0.1 ml per well in a 96-well plate. After a 4 hours incubation, the cells were harvested and stained with a fixable viability dye (eBioscience) and analyzed using the MACSQuant flow cytometer (Miltenyi).

The percentage of specific lysis was calculated using the following formula:

$$\% \text{ cell lysis} = 100\% - \frac{\frac{\% \text{ viable target cells upon coculture with } CAR \text{ modified } T \text{ cells}}{\% \text{ viable control cells upon coculture with } CAR \text{ modified } T \text{ cells}}}{\frac{\% \text{ viable target cells upon coculture with non modified } T \text{ cells}}{\% \text{ viable control cells upon coculture with non modified } T \text{ cells}}}$$

Example 1: Proliferation of TCRalpha Inactivated Cells Expressing a 5T4-CAR

Heterodimeric TALE-nuclease targeting two 17-bp long sequences (called half targets) separated by an 15-bp spacer within T-cell receptor alpha constant chain region (TRAC) gene were designed and produced. Each half target is recognized by repeats of the half TALE-nucleases listed in Table 10

TABLE 10

TAL-nucleases targeting TCRalpha gene

| Target | Target sequence | Polynucleotid encode TALEN | Half TALE-nuclease |
|---|---|---|---|
| TRAC_T01 | TTGTCCCACAGATATCC Agaaccctgaccctg CCGTGTACCAGCTGAGA (SEQ ID NO: 43) | T01-L (SEQ ID NO: 44) T01-R (SEQ ID NO: 45) | TRAC_T01-L TALEN (SEQ ID NO: 46) TRAC_T01-R TALEN (SEQ ID NO: 47) |

Each TALE-nuclease construct was subcloned using restriction enzyme digestion in a mammalian expression vector under the control of the T7 promoter. mRNA encoding TALE-nuclease cleaving TRAC genomic sequence were synthesized from plasmid carrying the coding sequence downstream from the T7 promoter.

Purified T cells preactivated during 72 hours with anti-CD3/CD28 coated beads were transfected with each of the 2 mRNAs encoding both half TRAC_T01 TALE-nucleases. 48 hours post-transfection, different groups of T cells from the same donor were respectively transduced with a lentiviral vector encoding one of the 5T4 CAR previously described (SEQ ID NO: 19 to 42). 2 days post-transduction, $CD3_{NEG}$ cells were purified using anti-CD3 magnetic beads and 5 days post-transduction cells were reactivated with soluble anti-CD28 (5 µg/ml).

Cell proliferation was followed for up to 30 days after reactivation by counting cell 2 times per week. Increased proliferation in TCR alpha inactivated cells expressing the 5T4 CARs, especially when reactivated with anti-CD28, was observed compared to non-transduced cells.

To investigate whether the human T cells expressing the 5T4 CAR display activated state, the expression of the activation marker CD25 are analyzed by FACS 7 days post transduction. The purified cells transduced with the lentiviral vector encoding 5T4 CAR assayed for CD25 expression at their surface in order to assess their activation in comparison with the non-transduced cells. Increased CD25 expression is expected both in CD28 reactivation or no reactivation conditions.

Example 2: Selection of 5T4-Positive and -Negative Cell Line

Eight human cell lines were screened for 5T4 expression by western blot and flow cytometry (see Table 11 below).

TABLE 11

Expression of 5T4 antigen in 8 human cell lines

| Cell line | Description | Cell type |
|---|---|---|
| MCF7 | adherent | adenocarcinoma |
| HCT116 | adherent | colorectal carcinoma |
| MKN45 | adherent | gastric carcinoma |
| LS174T | adherent | colorectal adecarcinoma |
| SK-MEL-28 | adherent | malignant melanoma |
| SupT1 | suspension | T-cell lymphoblastic lymphoma |
| Daudi | suspension | Burkitt's lymphoma |

5T4 was not detected in extracts from Daudi (ATCC CCL-213), SupT1 (ATT CRL-1942) and SK-MEL-28 (ATCC HTB-72) cells but was detected in extracts from MCF7 (ATCC HTB-22), HCT116 (ATCC CCL-247), MKN45 (JCRB0254) and LS174T (ATCC CL-188) cells.

Among the cells that were positive for 5T4 antigen following western blot analysis, only two were found to express 5T4 at the cell surface: MCF7 and HCT116 cells, MCF7 expressing highest levels of 5T4 antigen than HCT116 cells.

Example 3: Generation of Anti-5T4 scCARs

Second generation singlechain CARs specific for 5T4 (shown schematically in FIGS. 3 to 6 and and in Table 3 to Table 6) were created by combining the sequences of 4 different scFv with the sequences of 3 different spacers, 2 different transmembrane domains, 1 costimulatory domain and 1 stimulatory domain as represented in FIG. 2.

The sequences used in the CARs (presented in Table 1 and Table 2) derive from:
- the H8, A1, A2 or A3 antibodies for the scFv;
- the IgG1, FcεRIIIγ or CD8α molecules for the spacer domain;
- the CD8α or 4-1BB molecules for the transmembrane domain;
- the 4-1BB molecule for the costimulatory domain;
- the CD3ζ molecule for the stimulatory domain.

Example 4: In Vitro Testing of Anti-5T4 scCARs

To evaluate the activity of 5T4-specific singlechain CARs, human T cells from healthy volunteers were activated with CD3/CD28 beads and, eleven days post activation, were electroporated with mRNA encoding the CARs. CAR's activity and specificity were analysed 1-2 days post transfection by measuring T cells degranulation and T cell cytotoxicity against 5T4-positive and -negative target cells.

The results are presented below for the testing on one case (N=1), however experiments were performed on two other cases showing similar results (not shown).

Figure 7:
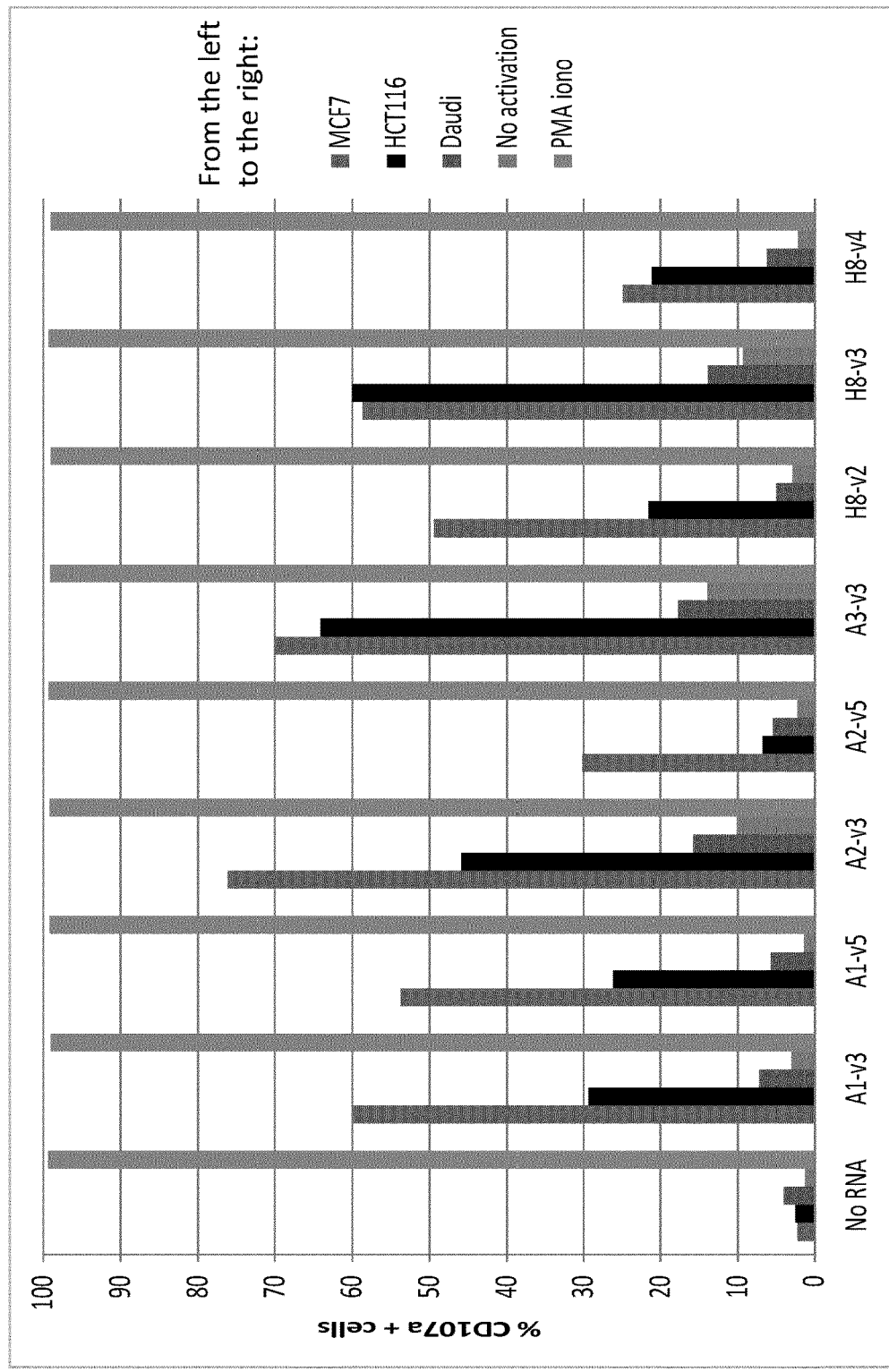
FIG. 7: T cell degranulation test for eight 5T4-CAR-engineered T cells lines according to the invention to assess their activity.

FIG. 7 shows that all the CARs tested induced significant level (20%) of T cells degranulation upon coculture with MCF7 but not upon coculture with Daudi cells. Among the eight CARs tested seven were also able to mediate T cells degranulation following coculture with HCT116 cells, a cell line expressing lower level of 5T4 than MCF7.

Figure 8:
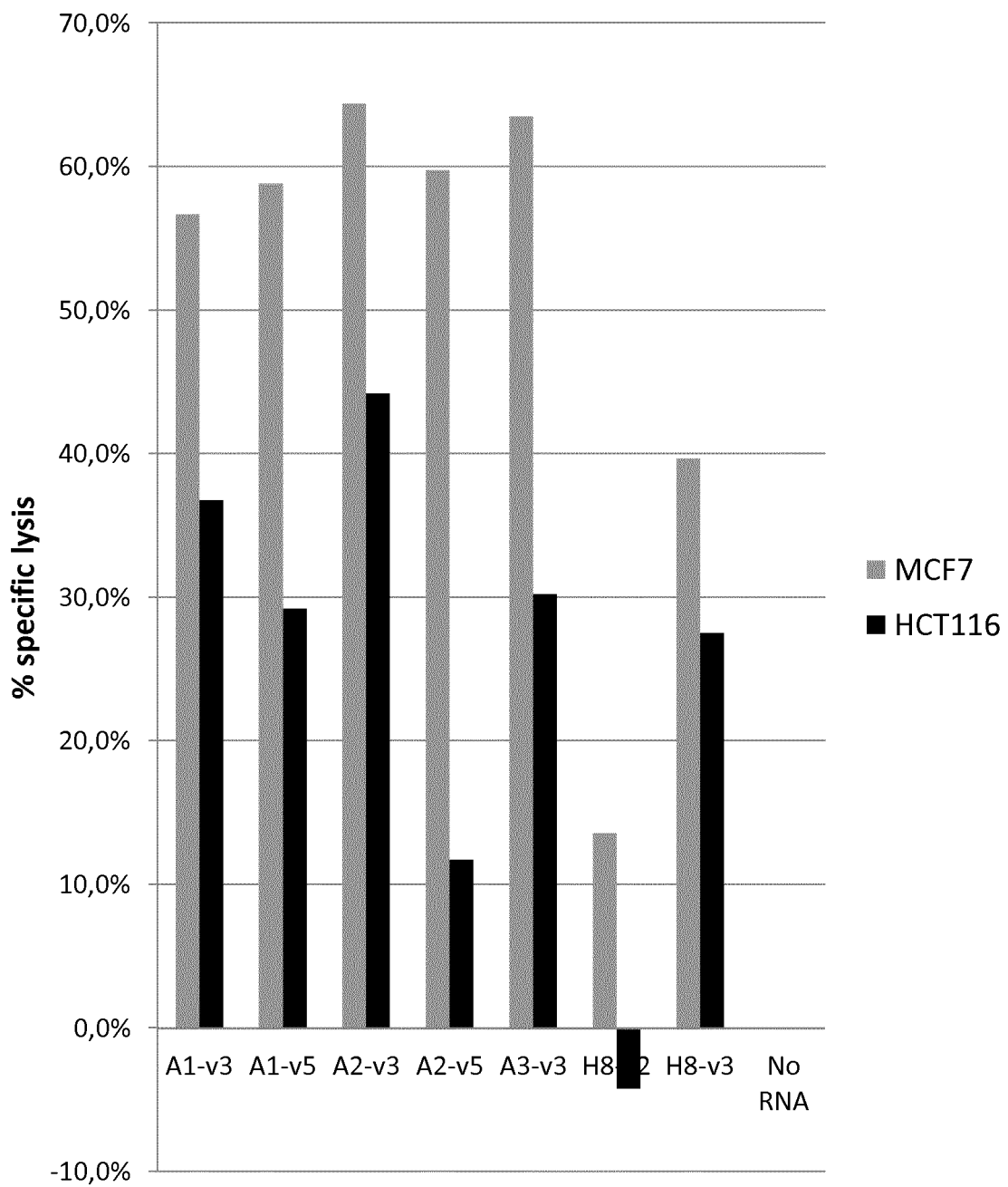
FIG. 8: T cell specific lysis for seven 5T4-CAR-enginereed T cells lines according to the invention to assess their specificity.

FIG. 8 shows that all the T cells modified with the A1-v3, A1-v5, A2-v3, A2-v5, A3-v3, H8-v2 and H8-v3 CARs lysed significantly and specifically MCF7 cells. T cells modified with the A1-v3, A1-v5, A2-v3, A2-v5, A3-v3 and H8-v3 CARs were also able to lyse HCT116 cells, a cell line expressing lower level of 5T4 than MCF7 cells.

Examples of CAR Polypeptide Sequences

Framed sequences correspond to preferred VH and VL sequences. VH and VL may be swapped to improve CAR efficiency.

```
H8 v1
MALPVTALLLPLALLLHAARP EVQLQQSGPDLVKPGASVKISCKASGYSFTGYYMHWVKQSHGKSLEWIGRINPNN

GVTLYNQKFKDKAILTVDKSSTTAYMELRSLTSEDSAVYYCARSTMITNYVMDYWGQVTSVTVSS GGGGSGGGGS

GGGGS SIVMTQTPTFLLVSAGDRVTITCKASQSVSNDVAWYQQKPGQSPTLLISYTSSRYAGVPDRFIGSGYGTDFT

FTISTLQAEDLAVYFCQQDYNSPPTFGGGTKLEIKR GLAVSTISSFFPPGYQIYIWAPLAGTCGVLLLSLVITLYCKRGR

KKLLYIFKQPFMRPVQTTQEEDGCSCRFPEEEEGGCELRVKSRSADAPAYQQSQNQLYNELNLGRREEYDVLDKR

RGRDPEMGGKPRRKNPQEGLYNELQKDKMAEAYSEIGMKGERRRGKGHDGLYQGLSTATKDTYDALHMQALPP

R

H8 v2
MALPVTALLLPLALLLHAARP EVQLQQSGPDLVKPGASVKISCKASGYSFTGYYMHWVKQSHGKSLEWIGRINPNN

GVTLYNQKFKDKAILTVDKSSTTAYMELRSLTSEDSAVYYCARSTMITNYVMDYWGQVTSVTVSS GGGGSGGGGS

GGGGS SIVMTQTPTFLLVSAGDRVTITCKASQSVSNDVAWYQQKPGQSPTLLISYTSSRYAGVPDRFIGSGYGTDFT

FTISTLQAEDLAVYFCQQDYNSPPTFGGGTKLEIKR GLAVSTISSFFPPGYQIISFFLALTSTALLFLLFFLTLRFSVVKRG

RKKLLYIFKQPFMRPVQTTQEEDGCSCRFPEEEEGGCELRVKFSRSADAPAYQQGQNQLYNELNLGRREEYDVLDK

RRGRDPEMGGKPRRKNPQEGLYNELKDKMAEAYSEIGMKGERRRGKGHDGLYQGLSTATKDTYDALHMQALP

PR

H8 v3
MALPVTALLLPLALLLHAARP EVQLQQSGPDLVKPGASVKISCKASGYSFTGYYMHWVKQSHGKSLEWIGRINPNN

GVTLYNQKFKDKAILTVDKSSTTAYMELRSLTSEDSAVYYCARSTMITNYVMDYWGQVTSVTVSS GGGGSGGGGS

GGGGS SIVMTQTPTFLLVSAGDRVTITCKASQSVSNDVAWYQQKPGQSPTLLISYTSSRYAGVPDRFIGSGYGTDFT

FTISTLQAEDLAVYFCQQDYNSPPTFGGGTKLEIKR TTTPAPRPPTPAPTIASQPLSLRPEACRPAAGGAVHTRGLDF

ACDIYIWAPLAGTCGVLLLSLVITLYCKRGRKKLLYIFKQPFMRPVQTTQEEDGCSCRFPEEEEGGCELRVKFSRSADA
```

PAYQQGQNQLYNELNLGRREEYDVLDKRRGRDPEMGGKPRRKNPQEGLYNELQKDMAEAYSEIGMKGERRRG

KGHDGLYQGLSTATKDTYDALHMQALPPR

H8 v4
MALPVTALLLPLALLLHAARP[EVQLQQSGPDLVKPGASVKISCKASGYSFTGYYMHWVKQSHGKSLEWIGRINPNN

GVTLYNQKFKDKAILTVDKSSTTAYMELRSLTSEDSAVYYCARSTMITNYVMDYWGQVTSVTVSS]GGGGSGGGGS

GGGGS[SIVMTQTPTFLLVSAGDRVTITCKASQSVSNDVAWYQQKPGQSPTLLISYTSSRYAGVPDRFIGSGYGTDFT

FTISTLQAEDLAVYFCQQDYNSPPTFGGGTKLEIKR]TTTPAPRPPTPAPTIASQPLSLRPEACRPAAGGAVHTRGLDF

ACDIISFFLALTSTALLFLLFFLTLRFSVVKRGRKKLLYIFKQPFMRPVQTTQEEDGCSCRFPEEEEGGCELRVKFSRSAD

APAYQQGQNQLYNELNLGREEYDVLDKRRGRDPEMGGKPRRKNPQEGLYNELQKDKMAEAYSEIGMKGERRR

GKGHDGLYQGLSTATKDTYDALHMQALPPR

H8 v5
MALPVTALLLPLALLLHAARP[EVQLQQSGPDLVKPGASVKISCKASGYSFTGYYMHWVKQSHGKSLEWIGRINPNN

GVTLYNQKFKDKAILTVDKSSTTAYMELRSLTSEDSAVYYCARSTMITNYVMDYWGQVTSVTVSS]GGGGSGGGGS

GGGGS[SIVMTQTPTFLLVSAGDRVTITCKASQSVSNDVAWYQQKPGQSPTLLISYTSSRYAGVPDRFIGSGYGTDFT

FTISTLQAEDLAVYFCQQDYNSPPTFGGGTKLEIKR]EPKSPDKTHTCPPCPAPPVAGPSVFLFPPKPKDTLMIARTPE

VTCVVVDVSHEDPEVKFNWYVDGVEVHNAKTKPREEQYNSTYRVVSVLTVLHQDWLNGEYKCKVSNKALPAPIE

KTISKAKGQPREPQVYTLPPSRDELTKNQVSLTCLVKGFYPSDIAVEWESNGQPENNYKTTPPVLDSDGSFFLYSKLT

VDKSRWQQGNVSCSVMHEALHNHYTQKSLSLSPGKIYIWAPLAGTCGVLLLSLVTTLYCKRGRKKLLYIFKQPFMR

PVQTTQEEDGCSCRFPEEEEGGCELRVKSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDTYDALHMQALPPR

H8 v6
MALPVTALLLPLALLLHAARP[EVQLQQSGPDLVKPGASVKISCKASGYSFTGYYMHWVKQSHGKSLEWIGRINPNN

GVTLYNQKFKDKAILTVDKSSTTAYMELRSLTSEDSAVYYCARSTMITNYVMDYWGQVTSVTVSS]GGGGSGGGGS

GGGGS[SIVMTQTPTFLLVSAGDRVTITCKASQSVSNDVAWYQQKPGQSPTLLISYTSSRYAGVPDRFIGSGYGTDFT

FTISTLQAEDLAVYFCQQDYNSPPTFGGGTKLEIKR]EPKSPDKTHTCPPCPAPPVAGPSVFLFPPKPKDTLMIARTPE

VTCVVVDVSHEDPEVKFNWYVDGVEVHNAKTKPREEQYNSTYRVVSVLTVLHQDWLNGEYKCKVSNKALPAPIE

KTISKAKGQPREPQVYTLPPSRDELTKNQVSLTCLVKGFYSDIAVEWESNGQPENNYKTTPPVLDSDGSFFLYSKLT

VDKSRWQQGNVFSCSVMHEALHNHYTQKSLSLSPGKIISFFLALTSTALLFLLFFLTLRFSVVKRGRKKLLYIFKQPFM

RPVQTTQEEDGCSCRFPEEEEGGCELRVKSRSADAPAYQQGQNQLYNELNLGRREEYDVLDKRRGRDPEMGGKP

RRKNPQEGLYNELQKDMAEAYSEIGMKGERRRGKGHDGLYQGLSTATKDTYDALHMQALPPR

A1 v1
MALPVTALLLPLALLLHAARP[QIQLVQSGPELKKPGETVKISCKASGYTFTNFGMNWVKQGPGEGLKWMGWINT

NTGEPRYAEEFKGRFAFSLETTASTAYLQINNLKNEDTATYFCARDWDGAYFFDYWGQGTTLTVSS]GGGSGGGGS

GGGGS[SIVMTQTPKFLLVSAGDRVTITCKASQSVSNDVAWYQQKPGQSPLLINFATNRYTGVPNRFTGSGYGTD

FTFTISTVQAEDLAYLYFCQQDYSSPWTFGGGTKLEIK]GLAVSTISSFFPPGYQIYIWAPLAGTCGVLLLSLVITLYCKRG

RKKLLYIFQPFMRPVQTTQEEDGCSCRFPEEEEGGCELVFSRSADAPAYQQGQNQLYNELNLGRREEYDVLDK

RRGRDPEMGGKPRRKNPQEGLYNELQKDMAEAYSEIGMKGERRRGKGHDGLYQGLSTATKDTYDALHMQALP

PR

A1 v2
MALPVTALLLPLALLLHAARP QIQLVQSGPELKKPGETVKISCKASGYTFTNFGMNWVKQGPGEGLKWMGWINT

NTGEPRYAEEFKGRFAFSLETTASTAYLQINNLKNEDTATYFCARDWDGAYFFDYWGQGTTLTVSS GGGSGGGGS

GGGGSS IVMTQTPKFLLVSAGDRVTITCKASQSVSNDVAWYQQKPGQSPKLLINFATNRYTGVPNRFTGSGYGTD

FTFTISTVQAEDLALYFCQQDYSSPWTFGGGTKLEI KGLAVSTISSFFPPGYQIISFFLALTSTALLFLLFFLTLRFSVVKR

GRKKLLYIFKQPFMRPVQTTQEEDGCSCRFPEEEEGGCELRVKFSRSADAPAYQQGQNQLYNELNLGRREEYDVLD

KRRGRDPEMGGPRRKNPQEGLYNELQKDMAEAYSEIGMKGERRRGKGHDGLYQGLSTATKDTYDALHMQAL

PPR

A1 v3
MALPVTALLLPLALLLHAARP QIQLVQSGPELKKPGETVKISCKASGYTFTNFGMNWVKQGPGEGLKWMGWINT

NTGEPRYAEEFKGRFAFSLETTASTAYLQINNLKNEDTATYFCARDWDGAYFFDYWGQGTTLTVSS GGGSGGGGS

GGGGS SIVMTQTPKFLLVSAGDRVTITCKASQSVSNDVAWYQQKPGQSPKLLINFATNRYTGVPNRFTGSGYGTD

FTFTISTVQAEDLALYFCQQDYSSPWTFGGGTKLEIK TTTPAPRPPTPAPTIASQPLSLRPEACRPAAGGAVHTRGLD

FACDIYIWAPLAGTCGVLLLSLVITLYCKRGRKKLLYIFKQPFMRPVQTTQEEDGCSCRFPEEEEGGCELRVKFSRSAD

APAYQQGQNQLYNELNLGRREEYDVLDKRRGRDPEMGGKPRRKNPQEGLYNELQKDMAEAYSEIGMKGERRR

GKGHDGLYQGLSTATKDTYDALHMQALPPR

A1 v4
MALPVTALLLPLALLLHAARP QIQLVQSGPELKKPGETVKISCKASGYTFTNFGMNWVKQGPGEGLKWMGWINT

NTGEPRYAEEFKGRFAFSLETTASTAYLQINNLKNEDTATYFCARDWDGAYFFDYWGQGTTLTVSS GGGSGGGGS

GGGGS SIVMTQTPKFLLVSAGDRVTITCKASQSVSNDVAWYQQKPGQSPKLLINFATNRYTGVPNRFTGSGYGTD

FTFTISTVQAEDLALYFCQQDYSSPWTFGGGTKLEIK TTTPAPRPPTPAPTIASQPLSLRPEACRPAAGGAVHTRGLD

FACDIISFFLALTSTALLFLLFFLTLRFSVVKRGRKKLLYIFKQPFMRPVQTTQEEDGCSCRFPEEEEGGCELRVKFSRSA

DAPAYQQGQNQLYNELNLGRREEYDVLDKRRGRDPEMGGKPRRKNPQEGLYNELQKDMAEAYSEIGMKGERR

GKGHDGLYQGLSTATKDTYDALHMQALPPR

A1 v5
MALPVTALLLPLALLLHAARP QIQLVQSGPELKKPGETVKISCKASGYTFTNFGMNWVKQGPGEGLKWMGWINT

NTGEPRYAEEFKGRFAFSLETTASTAYLQINNLKNEDTATYFCARDWDGAYFFDYWGQGTTLTVSS GGGSGGGGS

GGGGS SIVMTQTPKFLLVSAGDRVTITCKASQSVSNDVAWYQQKPGQSPKLLINFATNRYTGVPNRFTGSGYGTD

FTFTISTVQAEDLALYFCQQDYSSPWTFGGGTKLEIK EPKSPDKTHTCPPCPAPPVAGPSVFLFPPKPKDTLMIARTP

EVTCVVVDVSHEDPEVKFNWYVDGVEVHNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVEWESNGQPENNYKTTPPVLDSDGSFFLYSKL

TVDKSRWQQGNVSCSVMHEALHNHYTQKSLSLSPGKIYIWAPLAGTCGVLLLSLVITLYCKRGRKKLLYIFKQPFM

RPVQTTQEEDGCSCRFPEEEEGGCELRVKFSRSADAPAYQQGQNQLYNELNLGRREEYDVLDKRRGRDPEMGGKP

RRKNPQEGLYNELQKDMAEAYSEIGMKGERRRGKGHDGLYQGLSTATKDTYDALHMQALPPR

A1 v6
MALPVTALLLPLALLLHAARP QIQLVQSGPELKKPGETVKISCKASGYTFTNFGMNWVKQGPGEGLKWMGWINT

NTGEPRYAEEFKGRFAFSLETTASTAYLQINNLKNEDTATYFCARDWDGAYFFDYWGQGTTLTVSS GGGSGGGGS

GGGGS SIVMTQTPKFLLVSAGDRVTITCKASQSVSNDVAWYQQKPGQSPKLLINFATNRYTGVPNRFTGSGVGTD

FTFTISTVQAEDLALYFCQQDYSSPWTFGGGTKLEIKEPKSPDKTHTCPPCPAPPVAGPSVFLFPPKPKDTLMIARTP
EVTCVVVDVSHEDPEVKFNWYDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTPPVLDSDGSFFLYSKL
TVDKSRWQQGNVFSCSVMHEALHNHYTQKSLSLSPGKIIFFLALTSTALLFLLFFLTLRFSVVKRGRKKLLYIFKQPF
MRPVQTTQEEDGCSCRFPEEEEGGCELRVKFSRSADAPAYQQGQNQLYNELNLGRREEYDVLDKRRGRDPEMGS
KPRRKNPQEGLYNELQKDMAEAYSEIGMKGERRRGKGHDGLYQGLSTATKDTYDALHMQALPPR

A2 v1
MALPVTALLLPLALLLHAARPQVQLQQSRPELVKPGASVKMSCKASGYTFTDYVISWVKQRTGQGLEWIGEIYPGS
NSIYYNEKFKGRATLTADKSSSTAYMQLSSLTSEDSAVYFCAMGGNYGFDYWGQGTTLTVSSGGGGSGGGGSGG
GGSQIVLTQSPAIMSASLGERVTLTCTASSSVNSNYLHWYQQKPGSSPKLWIYSTSNLASGVPARFSGSGSGTSYSL
TISSMEAEDAATYYCHQYHRSPLTFGAGTKLELKGLAVSTISSFFPPGYQIYIWAPLAGTCGVLLLSLVIITLYCKRGRKK
LLYIFKQPFMRPVQTTQEEDGCSCRFPEEEEGGCELRVKFSRSADAPAYQQGQNQLYNELNLGRREEYDVLDKRRG
RDPEMGGKPRRKNPQEGLYNELQKDKMAEAYSEIGMKGERRRGKGHDGLYQGLSTATKDTYDALHMQALPPR

A2 v2
MALPVTALLLPLALLLHAARPQVQLQQSRPELVKPGASVKMSCKASGYTFTDYVISWVKQRTGQGLEWIGEIYPGS
NSIYYNEKFKGRATLTADKSSSTAYMQLSSLTSEDSAVYFCAMGGNYGFDYWGQGTTLTVSSGGGGSGGGGSGG
GGSQIVLTQSPAIMSASLGERVTLTCTASSSVNSNYLHWYQQKPGSSPKLWIYSTSNLASGVPARFSGSGSGTSVSL
TISSMEAEDAATYYCHQYHRSPLTFGAGTKLELKGLAVSTISSFFPPGYQIISFFLALTSTALLFLLFFLTLRFSVVKRGRK
KLLYIFKQPFMRPVQTTQEEDGCSCRFPEEEEGGCELRVKFSRSADAPAYQQGQNQLYNELNLGRREEYDVLDKRR
GRDPEMGGKPRRKNPQEGLYNELQKDKMAEAYSEIGMKGERRRGKGHDGLYQGLTATKDTYDALHMQALPPR

A2 v3
MALPVTALLLPLALLLHAARPQVQLQQSRPELVKPGASVKMSCKASGYTFTDYVISWVKQRTGQGLEWIGEIYPGS
NSIYYNEKFKGRATLTADKSSSTAYMQLSSLTSEDSAVYFCAMGGNYGFDYWGQGTTLTVSSGGGGSGGGGSGG
GGSQIVLTQSPAIMSASLGERVTLTCTASSSVNSNYLHWYQQKPGSSPKLWIYSTSNLASGVPARFSGSGSGTSYSL
TISSMEAEDAATYYCHQYHRSPLTFGAGTKLELKTTTPAPRPPTPAPTIASQPLSLRPEACRPAAGGAVHTRGLDFAC
DIYIWAPLAGTCGVLLLSLVITLYCKRGRKKLLYIFKQPFMRPVQTTQEEDGCSCRFPEEEEGGCELRVKFSRSADAPA
YQQGQNQLYNELNLGRREEYDVLDKRRGRDPEMGGKPRRKNPQEGLYNELQKDKMAEAYSEIGMKGERRRGKG
HDGLYQGLSTATKDTDALHMQALPPR

A2 v4
MALPVTALLLPLALLLHAARPQVQLQQSRPELVKPGASVKMSCKASGYTFTDYVISWVKQRTGQGLEWIGEIYPGS
NSIYYNEKFKGRATLTADKSSSTAYMQLSSLTSEDSAVYFCAMGGNYGFDYWGQGTTLTVSSGGGGSGGGGSGG
GGSQIVLTQSPAIMSASLGERVTLTCTASSSVNSNYLHWYQQKPGSSPKLWIYSTSNLASGVPARFSGSGSGTSVSL
TISSMEAEDAATYYCHQYHRSPLTFGAGTKLELKTTTPAPRPPTPAPTIASQPLSLRPEACRPAAGGAVHTRGLDFAC
DIISFFLALTSTALLFLLFFLTLRFSVVKRGRKKLLYIFKQPFMRPVQTTQEEDGCSCRFPEEEEGGCELRVKFRSADAP
AYQQGQNQLYNELNLGRREEYDVLDKRRGRDPEMGGKPRRKNPQEGLYNELQKDKMAEAYSEIGMKGERRRGK
GHDGLYQGLSTATKDTYDALHMQALPPR

A2 v5
MALPVTALLLPLALLLHAARPQVQLQQSRPELVKPGASVKMSCKASGYTFTDYVISWVKQRTGQGLEWIGEIYPGS
NSIYYNEKFKGRATLTADKSSSTAYMQLSSLTSEDSAVYFCAMGGNYGFDYWGQGTTLTVSSGGGGSGGGGSGG

```
GGSQIVLTQSPAIMSASLGERVTLTCTASSSVNSNYLHWYQQKPGSSPKLWIYSTSNLASGVPARFSGSGSGTSYSL

TISSMEAEDAATYYCHQYHRSPLTFGAGTKLELKEPKSPDKTHTCPPCPAPPVAGPSVFLFPPKPKDTLMIARTPEVT

CVVVDVSHEDPEVKFNWYVDGVEVHNAKTKPREEQYNSTYRVVSVLTVLHQDWLNGKEYKCKVSNKALPAPIEKT

ISKAKGQPREPQVYTLPPSRDELTKNQVSLTCLVKGFYPSIAVEWESNGQPENNYKTTPPVLDSDGSFFLYSKLTVC

KSRWQQGNVFSCSVMHEALHNHYTQKSLSLSPGKIYIWAPLAGTCGVLLLSLVITLYCKRGRKKLLYIFQPFMRPV

QTTQEEDGCSCRFPEEEEGGCELRVKFSRSADAPAYQQGQNQLYNELNLGRREEYDVLDKRRGRDPEMGGKPRRK

NPQEGLYNELQKDKMAEAYSEIGMKGERRRGKGHDGLYQGLSTATKDTYDALHMQALPPR

A2 v6
MALPVTALLLPLALLLHAARPQVQLQQSRPELVKPGASVKMSCKASGYTFTDYVISWVKQRTGQGLEWIGEIYPGS

NSIYYNEKFKGRATLTADKSSSTAYMQLSSLTSEDSAVYFCAMGGNYGFDYWGQGTTLTVSSGGGGSGGGGSGG

GGSQIVLTQSPAIMSASLGERVTLTCTASSSVNSNYLHWYQQKPGSSPKLWIYSTSNLASGVPARFSGSGSGTSYSL

TISSMEAEDAATYYCHQYHRSPLTFGAGTKLELKEPKSPDKTHTCPPCPAPPVAGPSVFLFPPKPKDTLMIARTPEVT

CVVVDVSHEDPEVKFNWYVDGVEVHNAKTKPREEQYNSTYRVVSVLTVLHQDWLNGEYKCKVSNKALPAPIEKT

ISKAKGQPREPQVYTLPPSRDELTKNQVSLTCLVKGFYPSDIAVEWESNGQPENNYKTTPPVLDSGSFFLYSKLTVD

KSRWQQGNFSCSVMHEALHNHYTQKSLSLSPGKIISFFLATSTALLFLLFFLTRFSVVKRGRKKLLYIFKQPFMRP

VQTTQEEDGCSCRFPEEEEGGCELRVKFSRSADAPAYQQGQNQLYNELNLGRREEYDVLDKRRGRDPEMGGKPR

RKNPQEGLYNELQKDMAEAYSEIGMKGERRRGKGHDGLYQGLSTATKDTYALHMQALPPR

A3 v1
MALPVTALLLPLALLLHAARPEVQLVESGGGLVQPKGSLKLSCAASGFTFNTYAMNWVRQAPGKGLEWVARIRSK

SNNYATYYADSVKDRFTISRDDSQSMLYLQMNNLKTEDTAMYYCVRQWDYDVRAMNYWGQGTSVTVSSGGG

GSGGGGSGGGGSDIVMTQSHIFMSTSVGDRVSITCKASQDVDTAVAWYQQKPGQSPKLLIYWASTRLTGVPDRF

TSGSGTDFTLTISNVQSEDLADYFCQQYSSYPYTFGGGTKLEIKGLAVSTISSFFPPGYQIYIWAPLAGTCGVLLLSLV

ITLYCKRGRKKLLYIFKQPFMRPVQTTQEEDGCSCRFPEEEEGGCELRVKFSRSADAPAYQQGQNQLYNELNLGRRE

EYDVLDKRRGRDPEMGGKPRRKNPQEGLYNELQKDMAEAYSEIGMKGERRGKGHDGLYQGLSTATKDTYDAL

HMQALPPR

A3 v2
MALPVTALLLPLALLLHAARPEVQLVESGGGLVQPKGSLKLSCAASGFTFNTYAMNWVRQAPGKGLEWVARIRSK

SNNYATYYADSVKDRFTISRDDSQSMLYLQMNNLKTEDTAMYYCVRQWDYDVRAMNYWGQGTSVTVSSGGG

GSGGGGSGGGGSDIVMTQSHIFMSTSVGDRVSITCKASQDVDTAVAWYQQKPGQSPKLLIYWASTRLTGVPDRF

TSGSGTDFTLTISNVQSEDLADYFCQQYSSYPYTFGGGTKLEIKGLAVSTISSFFPPGYQIISFFLALTSTALLFLLFFLTL

RFSVVKRGRKKLLYIFKQPFMRPVQTTQEEDGCSCRFPEEEEGGCELRVKFSRSADAPAYQQGQNQLYNELNLGRR

EEYDVLDKRRGRDPEMGGKPRRKNPQEGLYNELQKDMAEAYSEIGMKGERRRGKGHDGLYQGLSTATKDTYDA

LHMQALPPR

A3 v3
MALPVTALLLPLALLLHAARPEVQLVESGGGLVQPKGSLKLSCAASGFTFNTYAMNWVRQAPGKGLEWVARIRSK

SNNYATYYADSVKDRFTISRDDSQSMLYLQMNNLKTEDTAMYYCVRQWDYDVRAMNYWGQGTSVTVSSGGG

GSGGGGSGGGGSDIVMTQSHIFMSTSVGDRVSITCKASQDVDTAVAWYQQKPGQSPKLLIYWASTRLTGVPDRF

TSGSGTDFTLTISNVQSEDLADYFCQQYSSYPYTFGGGTKLEIKTTTPAPRPPTPAPTIASQPLSLRPEACRPAAGGA

VHTRGLDFACDIYIWAPLAGTCGVLLLSLVITLYCKRGRKKLLYIFKQPFMRPVQTTQEEDGCSCRFPEEEEGGCELRV
```

-continued

KFSRSADAPAYQQGQNQLYNELNLGRREEYDVLDKRRGRDPEMGGKPRRKNPQEGLYNELQKDKMAEAYSEIG

MKGERRRGKGHDGLYQGLSTATKDTYDALHMQALPPR

A3 v4
MALPVTALLLPLALLLHAARPEVQLVESGGGLVQPKGSLKLSCAASGFTFNTYAMNWVRQAPGKGLEWVARIRSK

SNNYATYYADSVKDRFTISRDDSQSMLYLQMNNLKTEDTAMYYCVRQWDYDVRAMNYWGQGTSVTVSSGGG

GSGGGGSGGGGSDIVMTQSHIFMSTSVGDRVSITCKASQDVDTAVAWYQQKPGQSPKLLIYWASTRLTGVPDRF

TGSGSGTDFTLTISNVQSEDLADYFCQQYSSYPYTFGGGTKLEIKTTTPAPRPPTPAPTIASQPLSLRPEACRPAAGGA

VHTRGLDFACDIISFFLALTSTALLFLLFFLTLRFSVVKRGRKKLLYIFKQPFMRPVQTTQEEDGCSCRFPEEEEGGCELR

VKFSRSADAPAYQQGQNQLYNELNLGRREEYDVLDKRRGRDPAMGGKPRRKNPQEGLYNELQKDMAEAYSEIG

MKGERRRGKGHDGLYQGLSTATKDTYDALHMQALPPR

A3 v5
MALPVTALLLPLALLLHAARPEVQLVESGGGLVQPKGSLKLSCAASGFTFNTYAMNWYVRQAPGKGLEWVARIRSK

SNNYATYYADSVKDRFTISRDDSQSMLYLQMNNLKTEDTAMYYCVRQWDYDVRAMNYWGQGTSVTVSSGGG

GSGGGGSGGGGSDIVMTQSHIFMSTSVGDRVSITCKASQDVDTAVAWYQQKPGQSPKLLIYWASTRLTGVPDRF

TGSGSGTDFTLTISNVQSEDLADYFCQQYSSYPYTFGGGTKLEIKEPKSPDKTHTCPPCPAPPVAGPSVFLFPPKPKD

TLMIARTPEVTCVVVDVSHEDPEVKFNWYVDGVEVHNAKTKPREEQYNSTYRVVSVLTVLHQDWLNGKEYKCKVS

NKALPAPIEKTISKAKGQPREPQVYTLPPSRDELTKNQVSLTCLVKFYPSDIAVEWSNGQPENNYKTTPPVLDSDG

SFFLYSKLTVDKSRWQQGNVFSCSVMHEALHNHYTQKSLSLPGKIYIWAPLAGTCGVLLLSLVITLYCKRGRKKLLYI

FKQFMRPVQTTQEEDGCSCRFPEEEEGGCELRVKFSRSADAPAYQQGQNQLYNELNLGRREEYDVLDKRRGRDP

EMGGKPRRKNPQEGLYNELQKDKMAEAYSEIGMKGERRRGKGHDGLYQGLSTATKDTYDALHMQALPPR

A3 v6
MALPVTALLLPLALLLHAARPEVQLVESGGGLVQPKGSLKLSCAASGFTFNTYAMNWVRQAPGKGLEWVARIRSK

SNNYATYYADSVKDRFTISRDDSQSMLYLQMNNLKTEDTAMYYCVRQWDYDVRAMNYWGQGTSVTVSSGGG

GSGGGGSGGGGSDIVMTQSHIFMSTSVGDRVSITCKASQDVDTAVAWYQQKPGQSPKLLIYWASTRLTGVPDRF

TGSGSGTDFTLTISNVQSEDLADYFCQQYSSYPYTFGGGTKLEIKEPKSPDKTHTCPPCPAPPVAGPSVFLFPPKPKD

TLMIARTPEVTCVVVDVSHEDPEVKFNWYVDGVEVHNAKTKPREEQYNSTYRVVSVLTVLHQDWLNGKEYKCKVS

NKALPAPIEKTISKAKGQPREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLPGKIISFFLALTSTALLFLLFFLTLRFSVVKRGRKKLL

YIFKQPFMRPVQTTQEEDGCSCRFPEEEEGGCELVKFSRSADAPAYQQGQNQLYNELNLGRREEYDVLDKRRGR

DPEMGGKPRRKNPQEGLYNELQKDMAEAYSEIGMKGERRRGKGHDGLYQGLSTATKDTYDALHMQALPPR

REFERENCES

Arimondo, P. B., C. J. Thomas, et al. (2006). "Exploring the cellular activity of camptothecin-triple-helix-forming oligonucleotide conjugates." *Mol Cell Biol* 26(1): 324-33.

Atkins, J. F., N. M. Wills, et al. (2007). "A case for "StopGo": reprogramming translation to augment codon meaning of GGN by promoting unconventional termination (Stop) after addition of glycine and then allowing continued translation (Go)." *Rna* 13(6): 803-10.

Bierer, B. E., G. Hollander, et al. (1993). "Cyclosporin A and FK506: molecular mechanisms of immunosuppression and probes for transplantation biology." *Curr Opin Immunol* 5(5): 763-73.

Boch, J., H. Scholze, et al. (2009). "Breaking the code of DNA binding specificity of TAL-type III effectors." *Science* 326(5959): 1509-12.

Byrd, John. (2014). "*Chronic Lymphocytic Leukemia*". ASH Annual Meeting & Exposition Carsberg, C. J., Myers, K. A., Evans, G. S., Allen, T. D., Stern, P. L (1995) "Metastasis-associated 5T4 oncofoetal antigen is concentrated at microvillus projections of the plasma membrane" J. Cell. Sci. 108 (8):2905-16.

Castro, F. V., McGinn, O. J., Krishnan, S., Marinov, G., Rutkowski, A. J., Elkord, E., Burt, D. J., Holland, M., Vaghjiani, R., Gallego, A., Saha, V. and Stern, P. L. (2012). "5T4 oncofetal antigen is expressed in high risk of relapse childhood pre-B acute lymphoblastic leukemia and is associated with a more invasive and chemotactic phenotype." *Leukemia* 26(7):1487-98

Choulika, A., A. Perrin, et al. (1995). "Induction of homologous recombination in mammalian chromosomes by using the I-SceI system of *Saccharomyces cerevisiae.*" *Mol Cell Biol* 15(4): 1968-73.

Christian, M., T. Cermak, et al. (2010). "Targeting DNA double-strand breaks with TAL effector nucleases." *Genetics* 186(2): 757-61.

Cong, L., F. A. Ran, et al. (2013). "Multiplex genome engineering using CRISPR/Cas systems." *Science* 339 (6121): 819-23.

Cros, E. et al. (2004). "Problems related to resistance to cytarabine in acute myeloid leukemia". *Leukemia & Lymphoma.* 45(6):1123-1132.

Deltcheva, E., K. Chylinski, et al. (2011). "CRISPR RNA maturation by trans-encoded small RNA and host factor RNase III." *Nature* 471(7340): 602-7.

Donnelly, M. and G. Elliott (2001). "Nuclear localization and shuttling of herpes simplex virus tegument protein VP13/14." *J Virol* 75(6): 2566-74.

Doronina, V. A., C. Wu, et al. (2008). "Site-specific release of nascent chains from ribosomes at a sense codon." *Mol Cell Biol* 28(13): 4227-39.

Eisenschmidt, K., T. Lanio, et al. (2005). "Developing a programmed restriction endonuclease for highly specific DNA cleavage." *Nucleic Acids Res* 33(22): 7039-47.

Gardin, C. et al. (2007). "Postremission treatment of elderly patients with acute myeloid leukemia in first complete remission after intensive induction chemotherapy:results of the multicenter randomized Acute Leukemia French Association (ALFA) 9803 trial". *Blood.* 109(12):5129-5135.

Garneau, J. E., M. E. Dupuis, et al. (2010). "The CRISPR/Cas bacterial immune system cleaves bacteriophage and plasmid DNA." *Nature* 468(7320): 67-71.

Gasiunas, G., R. Barrangou, et al. (2012). "Cas9-crRNA ribonucleoprotein complex mediates specific DNA cleavage for adaptive immunity in bacteria." *Proc Natl Acad Sci USA* 109(39): E2579-86.

Henderson, D. J., I. Naya, et al. (1991). "Comparison of the effects of FK-506, cyclosporin A and rapamycin on IL-2 production." *Immunology* 73(3): 316-21.

Hole, N., and Stern, P. L., (1988). "A 72 kD trophoblast glycoprotein defined by a monoclonal antibody." *Br. J. Cancer* 54: 239-246. Jena, B., G. Dotti, et al. (2010). "Redirecting T-cell specificity by introducing a tumor-specific chimeric antigen receptor." *Blood* 116(7): 1035-44.

Jinek, M., K. Chylinski, et al. (2012). "A programmable dual-RNA-guided DNA endonuclease in adaptive bacterial immunity." *Science* 337(6096): 816-21.

June, C. H. et al. (2011). "T Cells with Chimeric Antigen Receptors Have Potent Antitumor Effects and Can Establish Memory in Patients with Advanced Leukemia". *Sci. Transl. Med.* 3(95):ra73.

Kalish, J. M. and P. M. Glazer (2005). "Targeted genome modification via triple helix formation." *Ann N Y Acad Sci* 1058: 151-61.

Li, T., S. Huang, et al. (2011). "TAL nucleases (TALNs): hybrid proteins composed of TAL effectors and FokI DNA-cleavage domain." *Nucleic Acids Res* 39(1): 359-72.

Liu, J., M. W. Albers, et al. (1992). "Inhibition of T cell signaling by immunophilin-ligand complexes correlates with loss of calcineurin phosphatase activity." *Biochemistry* 31(16): 3896-901.

Mali, P., L. Yang, et al. (2013). "RNA-guided human genome engineering via Cas9." *Science* 339(6121): 823-6.

Moscou, M. J. and A. J. Bogdanove (2009). "A simple cipher governs DNA recognition by TAL effectors." *Science* 326(5959): 1501.

Paques, F. and P. Duchateau (2007). "Meganucleases and DNA double-strand break-induced recombination: perspectives for gene therapy." *Curr Gene Ther* 7(1): 49-66.

Park, T. S., S. A. Rosenberg, et al. (2011). "Treating cancer with genetically engineered T cells." *Trends Biotechnol* 29(11): 550-7.

Peipp, M., D. Saul, et al. (2004). "Efficient eukaryotic expression of fluorescent scFv fusion proteins directed against CD antigens for FACS applications." *J Immunol Methods* 285(2): 265-80.

Perrin, A., M. Buckle, et al. (1993). "Asymmetrical recognition and activity of the I-SceI endonuclease on its site and on intron-exon junctions." *Embo J* 12(7): 2939-47.

Pingoud, A. and G. H. Silva (2007). "Precision genome surgery." *Nat Biotechnol* 25(7): 743-4.

Porteus, M. H. and D. Carroll (2005). "Gene targeting using zinc finger nucleases." *Nat Biotechnol* 23(8): 967-73.

Rouet, P., F. Smih, et al. (1994). "Introduction of double-strand breaks into the genome of mouse cells by expression of a rare-cutting endonuclease." *Mol Cell Biol* 14(12): 8096-106.

Sorek, R., C. M. Lawrence, et al. (2013). "CRISPR-mediated Adaptive Immune Systems in Bacteria and Archaea." *Annu Rev Biochem.*

Starzynska, T., Wiechowska-Kozlowska, A., Marlicz, K., et al. (1998). "514 oncofetal antigen in gastric carcinoma and its clinical significance". EurJ *Gastroenterol Hepatol* 10 (6): 479-84

Stoddard, B. L. (2005). "Homing endonuclease structure and function." *Q Rev Biophys* 38(1): 49-95. Wrigley, E. McGown A. T., ⍰ Rennison J., Swindell R. Crowther, D. Starzynska T. and (1995). "Stern P. L. 5T4 oncofetal antigen expression in ovarian carcinoma". *International Journal of Gynecological Cancer.* 5 (4):269-274.

The invention claimed is:

1. A 5T4 (NTRKR1) specific chimeric antigen receptor (CAR) comprising:
   (a) an extracellular ligand binding-domain comprising a variable heavy chain comprising CDR regions as set forth in SEQ ID NO:60, SEQ ID NO:61, and SEQ ID NO:62, and a variable light chain comprising CDR regions as set forth in SEQ ID NO:63, SEQ ID NO:64, and SEQ ID NO:65,
   (b) a hinge comprising an amino acid sequence at least 95 percent identical to SEQ ID NO:4,
   (c) a transmembrane domain comprising an amino acid sequence at least 95 percent identical to SEQ ID NO:6, and
   (d) a cytoplasmic domain comprising (i) a signaling domain comprising an amino acid sequence at least 95 percent identical to SEQ ID NO:9 and (ii) a co-stimulatory domain comprising an amino acid sequence at least 95 percent identical to SEQ ID NO:8.

2. The 5T4 specific CAR according to claim 1, wherein said extracellular ligand binding-domain comprises the amino acid sequence set forth in SEQ ID NO:15 and SEQ ID NO:16.

3. The 5T4 specific CAR according to claim 1, wherein said co-stimulatory domain comprises the amino acid sequence set forth in SEQ ID NO:8.

4. The 5T4 specific CAR according to claim 1, wherein said signaling domain comprises the amino acid sequence set forth in SEQ ID NO:9.

5. The 5T4 specific CAR according to claim 1, wherein said hinge comprises the amino acid sequence set forth in SEQ ID NO:4.

6. The 5T4 specific CAR according to claim 1, wherein said transmembrane domain comprises the amino acid sequence set forth in SEQ ID NO:6.

7. The 5T4 specific CAR according to claim 1, wherein the 5T4 specific CAR comprises the amino acid sequence set forth in SEQ ID NO:33.

8. The 5T4 specific CAR according to claim 1, further comprising a signal peptide.

* * * * *

SEQUENCE LISTING

```
<160> NUMBER OF SEQ ID NOS: 71

<210> SEQ ID NO 1
<211> LENGTH: 20
<212> TYPE: PRT
<213> ORGANISM: artificial sequence
<220> FEATURE:
<223> OTHER INFORMATION: signal peptide

<400> SEQUENCE: 1
```

```
Met Glu Thr Asp Thr Leu Leu Leu Trp Val Leu Leu Leu Trp Val Pro
1               5                   10                  15

Gly Ser Thr Gly
            20
```

<210> SEQ ID NO 2
<211> LENGTH: 21
<212> TYPE: PRT
<213> ORGANISM: artificial sequence
<220> FEATURE:
<223> OTHER INFORMATION: signal peptide

<400> SEQUENCE: 2

```
Met Ala Leu Pro Val Thr Ala Leu Leu Leu Pro Leu Ala Leu Leu Leu
1               5                   10                  15

His Ala Ala Arg Pro
            20
```

<210> SEQ ID NO 3
<211> LENGTH: 16
<212> TYPE: PRT
<213> ORGANISM: homo sapiens
<220> FEATURE:
<223> OTHER INFORMATION: FcgRIIIa hinge

<400> SEQUENCE: 3

```
Gly Leu Ala Val Ser Thr Ile Ser Ser Phe Phe Pro Pro Gly Tyr Gln
1               5                   10                  15
```

<210> SEQ ID NO 4
<211> LENGTH: 45
<212> TYPE: PRT
<213> ORGANISM: homo sapiens
<220> FEATURE:
<223> OTHER INFORMATION: CD8alpha hinge

<400> SEQUENCE: 4

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
            35                  40                  45
```

<210> SEQ ID NO 5
<211> LENGTH: 231
<212> TYPE: PRT
<213> ORGANISM: homo sapiens
<220> FEATURE:
<223> OTHER INFORMATION: IgG1 hinge

<400> SEQUENCE: 5

```
Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ala Arg Thr Pro Glu Val Thr Cys Val Val Val
            35                  40                  45

Asp Val Ser His Glu Asp Pro Glu Val Lys Phe Asn Trp Tyr Val Asp
            50                  55                  60

Gly Val Glu Val His Asn Ala Lys Thr Lys Pro Arg Glu Glu Gln Tyr
65                  70                  75                  80
```

-continued

```
Asn Ser Thr Tyr Arg Val Val Ser Val Leu Thr Val Leu His Gln Asp
                 85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 6
<211> LENGTH: 24
<212> TYPE: PRT
<213> ORGANISM: homo sapiens
<220> FEATURE:
<223> OTHER INFORMATION: CD8alpha transmembrane domain

<400> SEQUENCE: 6

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 7
<211> LENGTH: 27
<212> TYPE: PRT
<213> ORGANISM: homo sapiens
<220> FEATURE:
<223> OTHER INFORMATION: 41BB transmembrane domain

<400> SEQUENCE: 7

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 8
<211> LENGTH: 42
<212> TYPE: PRT
<213> ORGANISM: homo sapiens
<220> FEATURE:
<223> OTHER INFORMATION: Fragment of 4-1BB (residues 214-255)

<400> SEQUENCE: 8

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
```

<210> SEQ ID NO 9
<211> LENGTH: 112
<212> TYPE: PRT
<213> ORGANISM: homo sapiens
<220> FEATURE:
<223> OTHER INFORMATION: fragment of T-cell surface glycoprotein CD3
      zeta chain

<400> SEQUENCE: 9

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 10
<211> LENGTH: 15
<212> TYPE: PRT
<213> ORGANISM: artificial sequence
<220> FEATURE:
<223> OTHER INFORMATION: linker sequence

<400> SEQUENCE: 10

Gly Gly Gly Gly Ser Gly Gly Gly Gly Ser Gly Gly Gly Gly Ser
1               5                   10                  15

<210> SEQ ID NO 11
<211> LENGTH: 120
<212> TYPE: PRT
<213> ORGANISM: artificial sequence
<220> FEATURE:
<223> OTHER INFORMATION: H8 heavy chain

<400> SEQUENCE: 11

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser His Gly Lys Ser Leu Glu Trp Ile
        35                  40                  45

Gly Arg Ile Asn Pro Asn Asn Gly Val Thr Leu Tyr Asn Gln Lys Phe
    50                  55                  60

Lys Asp Lys Ala Ile Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Ser Thr Met Ile Thr Asn Tyr Val Met Asp Tyr Trp Gly Gln
            100                 105                 110

Val Thr Ser Val Thr Val Ser Ser

<210> SEQ ID NO 12
<211> LENGTH: 108
<212> TYPE: PRT
<213> ORGANISM: artificial sequence
<220> FEATURE:
<223> OTHER INFORMATION: H8 light chain variable region

<400> SEQUENCE: 12

Ser Ile Val Met Thr Gln Thr Pro Thr Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Thr Leu Leu Ile
        35                  40                  45

Ser Tyr Thr Ser Ser Arg Tyr Ala Gly Val Pro Asp Arg Phe Ile Gly
    50                  55                  60

Ser Gly Tyr Gly Thr Asp Phe Thr Phe Thr Ile Ser Thr Leu Gln Ala
65                  70                  75                  80

Glu Asp Leu Ala Val Tyr Phe Cys Gln Gln Asp Tyr Asn Ser Pro Pro
                85                  90                  95

Thr Phe Gly Gly Gly Thr Lys Leu Glu Ile Lys Arg
            100                 105

<210> SEQ ID NO 13
<211> LENGTH: 119
<212> TYPE: PRT
<213> ORGANISM: artificial sequence
<220> FEATURE:
<223> OTHER INFORMATION: A3 heavy chain

<400> SEQUENCE: 13

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Phe
            20                  25                  30

Gly Met Asn Trp Val Lys Gln Gly Pro Gly Glu Gly Leu Lys Trp Met
        35                  40                  45

Gly Trp Ile Asn Thr Asn Thr Gly Glu Pro Arg Tyr Ala Glu Glu Phe
    50                  55                  60

Lys Gly Arg Phe Ala Phe Ser Leu Glu Thr Thr Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Asp Trp Asp Gly Ala Tyr Phe Phe Asp Tyr Trp Gly Gln Gly
            100                 105                 110

Thr Thr Leu Thr Val Ser Ser
        115

<210> SEQ ID NO 14
<211> LENGTH: 107
<212> TYPE: PRT
<213> ORGANISM: artificial sequence
<220> FEATURE:
<223> OTHER INFORMATION: A3 light chain

<400> SEQUENCE: 14

Ser Ile Val Met Thr Gln Thr Pro Lys Phe Leu Leu Val Ser Ala Gly
1               5                   10                  15

```
Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Asn Phe Ala Thr Asn Arg Tyr Thr Gly Val Pro Asn Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Leu Tyr Phe Cys Gln Gln Asp Tyr Ser Ser Pro Trp
                85                  90                  95

Thr Phe Gly Gly Gly Thr Lys Leu Glu Ile Lys
            100                 105

<210> SEQ ID NO 15
<211> LENGTH: 117
<212> TYPE: PRT
<213> ORGANISM: artificial sequence
<220> FEATURE:
<223> OTHER INFORMATION: A2 heavy chain

<400> SEQUENCE: 15

Gln Val Gln Leu Gln Gln Ser Arg Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Ser Trp Val Lys Gln Arg Thr Gly Gln Gly Leu Glu Trp Ile
        35                  40                  45

Gly Glu Ile Tyr Pro Gly Ser Asn Ser Ile Tyr Tyr Asn Glu Lys Phe
    50                  55                  60

Lys Gly Arg Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Met Gly Gly Asn Tyr Gly Phe Asp Tyr Trp Gly Gln Gly Thr Thr
            100                 105                 110

Leu Thr Val Ser Ser
        115

<210> SEQ ID NO 16
<211> LENGTH: 108
<212> TYPE: PRT
<213> ORGANISM: artificial sequence
<220> FEATURE:
<223> OTHER INFORMATION: A2 light chain

<400> SEQUENCE: 16

Gln Ile Val Leu Thr Gln Ser Pro Ala Ile Met Ser Ala Ser Leu Gly
1               5                   10                  15

Glu Arg Val Thr Leu Thr Cys Thr Ala Ser Ser Ser Val Asn Ser Asn
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
```

Leu Thr Phe Gly Ala Gly Thr Lys Leu Glu Leu Lys
            100                 105

<210> SEQ ID NO 17
<211> LENGTH: 122
<212> TYPE: PRT
<213> ORGANISM: artificial sequence
<220> FEATURE:
<223> OTHER INFORMATION: A3 heavy chain

<400> SEQUENCE: 17

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gln Trp Asp Tyr Asp Val Arg Ala Met Asn Tyr Trp
            100                 105                 110

Gly Gln Gly Thr Ser Val Thr Val Ser Ser
        115                 120

<210> SEQ ID NO 18
<211> LENGTH: 107
<212> TYPE: PRT
<213> ORGANISM: artificial sequence
<220> FEATURE:
<223> OTHER INFORMATION: A3 light chain

<400> SEQUENCE: 18

Asp Ile Val Met Thr Gln Ser His Ile Phe Met Ser Thr Ser Val Gly
1               5                   10                  15

Asp Arg Val Ser Ile Thr Cys Lys Ala Ser Gln Asp Val Asp Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg Leu Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys
            100                 105

<210> SEQ ID NO 19
<211> LENGTH: 458
<212> TYPE: PRT
<213> ORGANISM: artificial sequence
<220> FEATURE:
<223> OTHER INFORMATION: H8-v1 polypeptide CAR sequence

<400> SEQUENCE: 19

-continued

```
Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Asp Leu
            20                  25                  30

Val Lys Pro Gly Ala Ser Val Lys Ile Ser Cys Lys Ala Ser Gly Tyr
        35                  40                  45

Ser Phe Thr Gly Tyr Tyr Met His Trp Val Lys Gln Ser His Gly Lys
    50                  55                  60

Ser Leu Glu Trp Ile Gly Arg Ile Asn Pro Asn Asn Gly Val Thr Leu
65                  70                  75                  80

Tyr Asn Gln Lys Phe Lys Asp Lys Ala Ile Leu Thr Val Asp Lys Ser
                85                  90                  95

Ser Thr Thr Ala Tyr Met Glu Leu Arg Ser Leu Thr Ser Glu Asp Ser
            100                 105                 110

Ala Val Tyr Tyr Cys Ala Arg Ser Thr Met Ile Thr Asn Tyr Val Met
        115                 120                 125

Asp Tyr Trp Gly Gln Val Thr Ser Val Thr Val Ser Ser Gly Gly Gly
    130                 135                 140

Gly Ser Gly Gly Gly Gly Ser Gly Gly Gly Gly Ser Ser Ile Val Met
145                 150                 155                 160

Thr Gln Thr Pro Thr Phe Leu Leu Val Ser Ala Gly Asp Arg Val Thr
                165                 170                 175

Ile Thr Cys Lys Ala Ser Gln Ser Val Ser Asn Asp Val Ala Trp Tyr
            180                 185                 190

Gln Gln Lys Pro Gly Gln Ser Pro Thr Leu Leu Ile Ser Tyr Thr Ser
        195                 200                 205

Ser Arg Tyr Ala Gly Val Pro Asp Arg Phe Ile Gly Ser Gly Tyr Gly
    210                 215                 220

Thr Asp Phe Thr Phe Thr Ile Ser Thr Leu Gln Ala Glu Asp Leu Ala
225                 230                 235                 240

Val Tyr Phe Cys Gln Gln Asp Tyr Asn Ser Pro Pro Thr Phe Gly Gly
                245                 250                 255

Gly Thr Lys Leu Glu Ile Lys Arg Gly Leu Ala Val Ser Thr Ile Ser
            260                 265                 270

Ser Phe Phe Pro Pro Gly Tyr Gln Ile Tyr Ile Trp Ala Pro Leu Ala
        275                 280                 285

Gly Thr Cys Gly Val Leu Leu Leu Ser Leu Val Ile Thr Leu Tyr Cys
    290                 295                 300

Lys Arg Gly Arg Lys Lys Leu Leu Tyr Ile Phe Lys Gln Pro Phe Met
305                 310                 315                 320

Arg Pro Val Gln Thr Thr Gln Glu Glu Asp Gly Cys Ser Cys Arg Phe
                325                 330                 335

Pro Glu Glu Glu Glu Gly Gly Cys Glu Leu Arg Val Lys Phe Ser Arg
            340                 345                 350

Ser Ala Asp Ala Pro Ala Tyr Gln Gln Gly Gln Asn Gln Leu Tyr Asn
        355                 360                 365

Glu Leu Asn Leu Gly Arg Arg Glu Glu Tyr Asp Val Leu Asp Lys Arg
    370                 375                 380

Arg Gly Arg Asp Pro Glu Met Gly Gly Lys Pro Arg Arg Lys Asn Pro
385                 390                 395                 400

Gln Glu Gly Leu Tyr Asn Glu Leu Gln Lys Asp Lys Met Ala Glu Ala
                405                 410                 415
```

Tyr Ser Glu Ile Gly Met Lys Gly Glu Arg Arg Gly Lys Gly His
            420                 425                 430

Asp Gly Leu Tyr Gln Gly Leu Ser Thr Ala Thr Lys Asp Thr Tyr Asp
            435                 440                 445

Ala Leu His Met Gln Ala Leu Pro Pro Arg
450                 455

<210> SEQ ID NO 20
<211> LENGTH: 461
<212> TYPE: PRT
<213> ORGANISM: artificial sequence
<220> FEATURE:
<223> OTHER INFORMATION: H8-v2 polypeptide CAR sequence

<400> SEQUENCE: 20

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Asp Leu
            20                  25                  30

Val Lys Pro Gly Ala Ser Val Lys Ile Ser Cys Lys Ala Ser Gly Tyr
        35                  40                  45

Ser Phe Thr Gly Tyr Tyr Met His Trp Val Lys Gln Ser His Gly Lys
    50                  55                  60

Ser Leu Glu Trp Ile Gly Arg Ile Asn Pro Asn Asn Gly Val Thr Leu
65                  70                  75                  80

Tyr Asn Gln Lys Phe Lys Asp Lys Ala Ile Leu Thr Val Asp Lys Ser
                85                  90                  95

Ser Thr Thr Ala Tyr Met Glu Leu Arg Ser Leu Thr Ser Glu Asp Ser
            100                 105                 110

Ala Val Tyr Tyr Cys Ala Arg Ser Thr Met Ile Thr Asn Tyr Val Met
        115                 120                 125

Asp Tyr Trp Gly Gln Val Thr Ser Val Thr Val Ser Ser Gly Gly Gly
    130                 135                 140

Gly Ser Gly Gly Gly Gly Ser Gly Gly Gly Gly Ser Ser Ile Val Met
145                 150                 155                 160

Thr Gln Thr Pro Thr Phe Leu Leu Val Ser Ala Gly Asp Arg Val Thr
                165                 170                 175

Ile Thr Cys Lys Ala Ser Gln Ser Val Ser Asn Asp Val Ala Trp Tyr
            180                 185                 190

Gln Gln Lys Pro Gly Gln Ser Pro Thr Leu Leu Ile Ser Tyr Thr Ser
        195                 200                 205

Ser Arg Tyr Ala Gly Val Pro Asp Arg Phe Ile Gly Ser Gly Tyr Gly
    210                 215                 220

Thr Asp Phe Thr Phe Thr Ile Ser Thr Leu Gln Ala Glu Asp Leu Ala
225                 230                 235                 240

Val Tyr Phe Cys Gln Gln Asp Tyr Asn Ser Pro Pro Thr Phe Gly Gly
                245                 250                 255

Gly Thr Lys Leu Glu Ile Lys Arg Gly Leu Ala Val Ser Thr Ile Ser
            260                 265                 270

Ser Phe Phe Pro Pro Gly Tyr Gln Ile Ile Ser Phe Leu Ala Leu
        275                 280                 285

Thr Ser Thr Ala Leu Leu Phe Leu Leu Phe Leu Thr Leu Arg Phe
    290                 295                 300

Ser Val Val Lys Arg Gly Arg Lys Lys Leu Leu Tyr Ile Phe Lys Gln
305                 310                 315                 320

```
Pro Phe Met Arg Pro Val Gln Thr Thr Gln Glu Glu Asp Gly Cys Ser
            325                 330                 335

Cys Arg Phe Pro Glu Glu Glu Gly Gly Cys Glu Leu Arg Val Lys
        340                 345                 350

Phe Ser Arg Ser Ala Asp Ala Pro Ala Tyr Gln Gln Gly Gln Asn Gln
            355                 360                 365

Leu Tyr Asn Glu Leu Asn Leu Gly Arg Arg Glu Glu Tyr Asp Val Leu
    370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
            420                 425                 430

Lys Gly His Asp Gly Leu Tyr Gln Gly Leu Ser Thr Ala Thr Lys Asp
        435                 440                 445

Thr Tyr Asp Ala Leu His Met Gln Ala Leu Pro Pro Arg
    450                 455                 460

<210> SEQ ID NO 21
<211> LENGTH: 487
<212> TYPE: PRT
<213> ORGANISM: artificial sequence
<220> FEATURE:
<223> OTHER INFORMATION: H8-v3 polypeptide CAR sequence

<400> SEQUENCE: 21

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Asp Leu
            20                  25                  30

Val Lys Pro Gly Ala Ser Val Lys Ile Ser Cys Lys Ala Ser Gly Tyr
        35                  40                  45

Ser Phe Thr Gly Tyr Tyr Met His Trp Val Lys Gln Ser His Gly Lys
    50                  55                  60

Ser Leu Glu Trp Ile Gly Arg Ile Asn Pro Asn Asn Gly Val Thr Leu
65                  70                  75                  80

Tyr Asn Gln Lys Phe Lys Asp Lys Ala Ile Leu Thr Val Asp Lys Ser
                85                  90                  95

Ser Thr Thr Ala Tyr Met Glu Leu Arg Ser Leu Thr Ser Glu Asp Ser
            100                 105                 110

Ala Val Tyr Tyr Cys Ala Arg Ser Thr Met Ile Thr Asn Tyr Val Met
        115                 120                 125

Asp Tyr Trp Gly Gln Val Thr Ser Val Thr Val Ser Ser Gly Gly Gly
    130                 135                 140

Gly Ser Gly Gly Gly Gly Ser Gly Gly Gly Gly Ser Ser Ile Val Met
145                 150                 155                 160

Thr Gln Thr Pro Thr Phe Leu Leu Val Ser Ala Gly Asp Arg Val Thr
                165                 170                 175

Ile Thr Cys Lys Ala Ser Gln Ser Val Ser Asn Asp Val Ala Trp Tyr
            180                 185                 190

Gln Gln Lys Pro Gly Gln Ser Pro Thr Leu Leu Ile Ser Tyr Thr Ser
        195                 200                 205

Ser Arg Tyr Ala Gly Val Pro Asp Arg Phe Ile Gly Ser Gly Tyr Gly
    210                 215                 220
```

Thr Asp Phe Thr Phe Thr Ile Ser Thr Leu Gln Ala Glu Asp Leu Ala
225                 230                 235                 240

Val Tyr Phe Cys Gln Gln Asp Tyr Asn Ser Pro Pro Thr Phe Gly Gly
            245                 250                 255

Gly Thr Lys Leu Glu Ile Lys Arg Thr Thr Thr Pro Ala Pro Arg Pro
        260                 265                 270

Pro Thr Pro Ala Pro Thr Ile Ala Ser Gln Pro Leu Ser Leu Arg Pro
    275                 280                 285

Glu Ala Cys Arg Pro Ala Ala Gly Gly Ala Val His Thr Arg Gly Leu
290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
            325                 330                 335

Arg Lys Lys Leu Leu Tyr Ile Phe Lys Gln Pro Phe Met Arg Pro Val
        340                 345                 350

Gln Thr Thr Gln Glu Glu Asp Gly Cys Ser Cys Arg Phe Pro Glu Glu
    355                 360                 365

Glu Glu Gly Gly Cys Glu Leu Arg Val Lys Phe Ser Arg Ser Ala Asp
370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
            405                 410                 415

Asp Pro Glu Met Gly Gly Lys Pro Arg Arg Lys Asn Pro Gln Glu Gly
        420                 425                 430

Leu Tyr Asn Glu Leu Gln Lys Asp Lys Met Ala Glu Ala Tyr Ser Glu
    435                 440                 445

Ile Gly Met Lys Gly Glu Arg Arg Arg Gly Lys Gly His Asp Gly Leu
450                 455                 460

Tyr Gln Gly Leu Ser Thr Ala Thr Lys Asp Thr Tyr Asp Ala Leu His
465                 470                 475                 480

Met Gln Ala Leu Pro Pro Arg
            485

<210> SEQ ID NO 22
<211> LENGTH: 490
<212> TYPE: PRT
<213> ORGANISM: artificial sequence
<220> FEATURE:
<223> OTHER INFORMATION: H8-v4 polypeptide CAR sequence

<400> SEQUENCE: 22

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Asp Leu
            20                  25                  30

Val Lys Pro Gly Ala Ser Val Lys Ile Ser Cys Lys Ala Ser Gly Tyr
        35                  40                  45

Ser Phe Thr Gly Tyr Tyr Met His Trp Val Lys Gln Ser His Gly Lys
    50                  55                  60

Ser Leu Glu Trp Ile Gly Arg Ile Asn Pro Asn Asn Gly Val Thr Leu
65              70                  75                  80

Tyr Asn Gln Lys Phe Lys Asp Lys Ala Ile Leu Thr Val Asp Lys Ser
                85                  90                  95

Ser Thr Thr Ala Tyr Met Glu Leu Arg Ser Leu Thr Ser Glu Asp Ser
            100                 105                 110

Ala Val Tyr Tyr Cys Ala Arg Ser Thr Met Ile Thr Asn Tyr Val Met
        115                 120                 125

Asp Tyr Trp Gly Gln Val Thr Ser Val Thr Val Ser Ser Gly Gly Gly
    130                 135                 140

Gly Ser Gly Gly Gly Gly Ser Gly Gly Gly Gly Ser Ser Ile Val Met
145                 150                 155                 160

Thr Gln Thr Pro Thr Phe Leu Leu Val Ser Ala Gly Asp Arg Val Thr
                165                 170                 175

Ile Thr Cys Lys Ala Ser Gln Ser Val Ser Asn Asp Val Ala Trp Tyr
            180                 185                 190

Gln Gln Lys Pro Gly Gln Ser Pro Thr Leu Leu Ile Ser Tyr Thr Ser
        195                 200                 205

Ser Arg Tyr Ala Gly Val Pro Asp Arg Phe Ile Gly Ser Gly Tyr Gly
    210                 215                 220

Thr Asp Phe Thr Phe Thr Ile Ser Thr Leu Gln Ala Glu Asp Leu Ala
225                 230                 235                 240

Val Tyr Phe Cys Gln Gln Asp Tyr Asn Ser Pro Pro Thr Phe Gly Gly
                245                 250                 255

Gly Thr Lys Leu Glu Ile Lys Arg Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300

Asp Phe Ala Cys Asp Ile Ile Ser Phe Phe Leu Ala Leu Thr Ser Thr
305                 310                 315                 320

Ala Leu Leu Phe Leu Leu Phe Phe Leu Thr Leu Arg Phe Ser Val Val
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 23
<211> LENGTH: 490
<212> TYPE: PRT

<213> ORGANISM: artificial sequence
<220> FEATURE:
<223> OTHER INFORMATION: H8-v5 polypeptide CAR sequence

<400> SEQUENCE: 23

```
Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Asp Leu
            20                  25                  30

Val Lys Pro Gly Ala Ser Val Lys Ile Ser Cys Lys Ala Ser Gly Tyr
        35                  40                  45

Ser Phe Thr Gly Tyr Tyr Met His Trp Val Lys Gln Ser His Gly Lys
50                  55                  60

Ser Leu Glu Trp Ile Gly Arg Ile Asn Pro Asn Asn Gly Val Thr Leu
65                  70                  75                  80

Tyr Asn Gln Lys Phe Lys Asp Lys Ala Ile Leu Thr Val Asp Lys Ser
                85                  90                  95

Ser Thr Thr Ala Tyr Met Glu Leu Arg Ser Leu Thr Ser Glu Asp Ser
            100                 105                 110

Ala Val Tyr Tyr Cys Ala Arg Ser Thr Met Ile Thr Asn Tyr Val Met
        115                 120                 125

Asp Tyr Trp Gly Gln Val Thr Ser Val Thr Val Ser Ser Gly Gly Gly
130                 135                 140

Gly Ser Gly Gly Gly Gly Ser Gly Gly Gly Gly Ser Ser Ile Val Met
145                 150                 155                 160

Thr Gln Thr Pro Thr Phe Leu Leu Val Ser Ala Gly Asp Arg Val Thr
                165                 170                 175

Ile Thr Cys Lys Ala Ser Gln Ser Val Ser Asn Asp Val Ala Trp Tyr
            180                 185                 190

Gln Gln Lys Pro Gly Gln Ser Pro Thr Leu Leu Ile Ser Tyr Thr Ser
        195                 200                 205

Ser Arg Tyr Ala Gly Val Pro Asp Arg Phe Ile Gly Ser Gly Tyr Gly
210                 215                 220

Thr Asp Phe Thr Phe Thr Ile Ser Thr Leu Gln Ala Glu Asp Leu Ala
225                 230                 235                 240

Val Tyr Phe Cys Gln Gln Asp Tyr Asn Ser Pro Pro Thr Phe Gly Gly
                245                 250                 255

Gly Thr Lys Leu Glu Ile Lys Arg Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
290                 295                 300

Asp Phe Ala Cys Asp Ile Ile Ser Phe Phe Leu Ala Leu Thr Ser Thr
305                 310                 315                 320

Ala Leu Leu Phe Leu Leu Phe Phe Leu Thr Leu Arg Phe Ser Val Val
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Asp Gly Cys Ser Cys Arg Phe
        355                 360                 365

Pro Glu Glu Glu Glu Gly Gly Cys Glu Leu Arg Val Lys Phe Ser Arg
370                 375                 380

Ser Ala Asp Ala Pro Ala Tyr Gln Gln Gly Gln Asn Gln Leu Tyr Asn
```

```
            385                 390                 395                 400
        Glu Leu Asn Leu Gly Arg Arg Glu Tyr Asp Val Leu Asp Lys Arg
                        405                 410                 415

Arg Gly Arg Asp Pro Glu Met Gly Gly Lys Pro Arg Arg Lys Asn Pro
                        420                 425                 430

Gln Glu Gly Leu Tyr Asn Glu Leu Gln Lys Asp Lys Met Ala Glu Ala
                        435                 440                 445

Tyr Ser Glu Ile Gly Met Lys Gly Glu Arg Arg Arg Gly Lys Gly His
                        450                 455                 460

Asp Gly Leu Tyr Gln Gly Leu Ser Thr Ala Thr Lys Asp Thr Tyr Asp
        465                 470                 475                 480

Ala Leu His Met Gln Ala Leu Pro Pro Arg
                        485                 490

<210> SEQ ID NO 24
<211> LENGTH: 676
<212> TYPE: PRT
<213> ORGANISM: artificial sequence
<220> FEATURE:
<223> OTHER INFORMATION: H8-v6 polypeptide CAR sequence

<400> SEQUENCE: 24

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Asp Leu
                20                  25                  30

Val Lys Pro Gly Ala Ser Val Lys Ile Ser Cys Lys Ala Ser Gly Tyr
            35                  40                  45

Ser Phe Thr Gly Tyr Tyr Met His Trp Val Lys Gln Ser His Gly Lys
        50                  55                  60

Ser Leu Glu Trp Ile Gly Arg Ile Asn Pro Asn Asn Gly Val Thr Leu
65                  70                  75                  80

Tyr Asn Gln Lys Phe Lys Asp Lys Ala Ile Leu Thr Val Asp Lys Ser
                85                  90                  95

Ser Thr Thr Ala Tyr Met Glu Leu Arg Ser Leu Thr Ser Glu Asp Ser
            100                 105                 110

Ala Val Tyr Tyr Cys Ala Arg Ser Thr Met Ile Thr Asn Tyr Val Met
        115                 120                 125

Asp Tyr Trp Gly Gln Val Thr Ser Val Thr Val Ser Ser Gly Gly Gly
    130                 135                 140

Gly Ser Gly Gly Gly Gly Ser Gly Gly Gly Gly Ser Ser Ile Val Met
145                 150                 155                 160

Thr Gln Thr Pro Thr Phe Leu Leu Val Ser Ala Gly Asp Arg Val Thr
                165                 170                 175

Ile Thr Cys Lys Ala Ser Gln Ser Val Ser Asn Asp Val Ala Trp Tyr
            180                 185                 190

Gln Gln Lys Pro Gly Gln Ser Pro Thr Leu Leu Ile Ser Tyr Thr Ser
        195                 200                 205

Ser Arg Tyr Ala Gly Val Pro Asp Arg Phe Ile Gly Ser Gly Tyr Gly
    210                 215                 220

Thr Asp Phe Thr Phe Thr Ile Ser Thr Leu Gln Ala Glu Asp Leu Ala
225                 230                 235                 240

Val Tyr Phe Cys Gln Gln Asp Tyr Asn Ser Pro Pro Thr Phe Gly Gly
                245                 250                 255

Gly Thr Lys Leu Glu Ile Lys Arg Glu Pro Lys Ser Pro Asp Lys Thr
```

```
                260             265             270
His Thr Cys Pro Pro Cys Pro Ala Pro Pro Val Ala Gly Pro Ser Val
            275             280             285

Phe Leu Phe Pro Pro Lys Pro Lys Asp Thr Leu Met Ile Ala Arg Thr
            290             295             300

Pro Glu Val Thr Cys Val Val Val Asp Val Ser His Glu Asp Pro Glu
305             310             315             320

Val Lys Phe Asn Trp Tyr Val Asp Gly Val Glu Val His Asn Ala Lys
                325             330             335

Thr Lys Pro Arg Glu Glu Gln Tyr Asn Ser Thr Tyr Arg Val Val Ser
            340             345             350

Val Leu Thr Val Leu His Gln Asp Trp Leu Asn Gly Lys Glu Tyr Lys
            355             360             365

Cys Lys Val Ser Asn Lys Ala Leu Pro Ala Pro Ile Glu Lys Thr Ile
            370             375             380

Ser Lys Ala Lys Gly Gln Pro Arg Glu Pro Gln Val Tyr Thr Leu Pro
385             390             395             400

Pro Ser Arg Asp Glu Leu Thr Lys Asn Gln Val Ser Leu Thr Cys Leu
                405             410             415

Val Lys Gly Phe Tyr Pro Ser Asp Ile Ala Val Glu Trp Glu Ser Asn
            420             425             430

Gly Gln Pro Glu Asn Asn Tyr Lys Thr Thr Pro Pro Val Leu Asp Ser
            435             440             445

Asp Gly Ser Phe Phe Leu Tyr Ser Lys Leu Thr Val Asp Lys Ser Arg
            450             455             460

Trp Gln Gln Gly Asn Val Phe Ser Cys Ser Val Met His Glu Ala Leu
465             470             475             480

His Asn His Tyr Thr Gln Lys Ser Leu Ser Leu Ser Pro Gly Lys Ile
                485             490             495

Ile Ser Phe Phe Leu Ala Leu Thr Ser Thr Ala Leu Leu Phe Leu Leu
            500             505             510

Phe Phe Leu Thr Leu Arg Phe Ser Val Val Lys Arg Gly Arg Lys Lys
            515             520             525

Leu Leu Tyr Ile Phe Lys Gln Pro Phe Met Arg Pro Val Gln Thr Thr
            530             535             540

Gln Glu Glu Asp Gly Cys Ser Cys Arg Phe Pro Glu Glu Glu Glu Gly
545             550             555             560

Gly Cys Glu Leu Arg Val Lys Phe Ser Arg Ser Ala Asp Ala Pro Ala
                565             570             575

Tyr Gln Gln Gly Gln Asn Gln Leu Tyr Asn Glu Leu Asn Leu Gly Arg
            580             585             590

Arg Glu Glu Tyr Asp Val Leu Asp Lys Arg Arg Gly Arg Asp Pro Glu
            595             600             605

Met Gly Gly Lys Pro Arg Arg Lys Asn Pro Gln Glu Gly Leu Tyr Asn
            610             615             620

Glu Leu Gln Lys Asp Lys Met Ala Glu Ala Tyr Ser Glu Ile Gly Met
625             630             635             640

Lys Gly Glu Arg Arg Arg Gly Lys Gly His Asp Gly Leu Tyr Gln Gly
                645             650             655

Leu Ser Thr Ala Thr Lys Asp Thr Tyr Asp Ala Leu His Met Gln Ala
            660             665             670

Leu Pro Pro Arg
            675
```

<210> SEQ ID NO 25
<211> LENGTH: 455
<212> TYPE: PRT
<213> ORGANISM: artificial sequence
<220> FEATURE:
<223> OTHER INFORMATION: A1-v1 polypeptide CAR sequence

<400> SEQUENCE: 25

```
Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Pro Glu Leu
            20                  25                  30

Lys Lys Pro Gly Glu Thr Val Lys Ile Ser Cys Lys Ala Ser Gly Tyr
        35                  40                  45

Thr Phe Thr Asn Phe Gly Met Asn Trp Val Lys Gln Gly Pro Gly Glu
    50                  55                  60

Gly Leu Lys Trp Met Gly Trp Ile Asn Thr Asn Thr Gly Glu Pro Arg
65                  70                  75                  80

Tyr Ala Glu Glu Phe Lys Gly Arg Phe Ala Phe Ser Leu Glu Thr Thr
                85                  90                  95

Ala Ser Thr Ala Tyr Leu Gln Ile Asn Asn Leu Lys Asn Glu Asp Thr
            100                 105                 110

Ala Thr Tyr Phe Cys Ala Arg Asp Trp Asp Gly Ala Tyr Phe Phe Asp
        115                 120                 125

Tyr Trp Gly Gln Gly Thr Thr Leu Thr Val Ser Ser Gly Gly Gly Ser
    130                 135                 140

Gly Gly Gly Gly Ser Gly Gly Gly Ser Ser Ile Val Met Thr Gln
145                 150                 155                 160

Thr Pro Lys Phe Leu Leu Val Ser Ala Gly Asp Arg Val Thr Ile Thr
                165                 170                 175

Cys Lys Ala Ser Gln Ser Val Ser Asn Asp Val Ala Trp Tyr Gln Gln
            180                 185                 190

Lys Pro Gly Gln Ser Pro Lys Leu Leu Ile Asn Phe Ala Thr Asn Arg
        195                 200                 205

Tyr Thr Gly Val Pro Asn Arg Phe Thr Gly Ser Gly Tyr Gly Thr Asp
    210                 215                 220

Phe Thr Phe Thr Ile Ser Thr Val Gln Ala Glu Asp Leu Ala Leu Tyr
225                 230                 235                 240

Phe Cys Gln Gln Asp Tyr Ser Ser Pro Trp Thr Phe Gly Gly Gly Thr
                245                 250                 255

Lys Leu Glu Ile Lys Gly Leu Ala Val Ser Thr Ile Ser Ser Phe Phe
            260                 265                 270

Pro Pro Gly Tyr Gln Ile Tyr Ile Trp Ala Pro Leu Ala Gly Thr Cys
        275                 280                 285

Gly Val Leu Leu Leu Ser Leu Val Ile Thr Leu Tyr Cys Lys Arg Gly
    290                 295                 300

Arg Lys Lys Leu Leu Tyr Ile Phe Lys Gln Pro Phe Met Arg Pro Val
305                 310                 315                 320

Gln Thr Thr Gln Glu Glu Asp Gly Cys Ser Cys Arg Phe Pro Glu Glu
                325                 330                 335

Glu Glu Gly Gly Cys Glu Leu Arg Val Lys Phe Ser Arg Ser Ala Asp
            340                 345                 350

Ala Pro Ala Tyr Gln Gln Gly Gln Asn Gln Leu Tyr Asn Glu Leu Asn
        355                 360                 365
```

-continued

Leu Gly Arg Arg Glu Glu Tyr Asp Val Leu Asp Lys Arg Gly Arg
        370                 375                 380

Asp Pro Glu Met Gly Gly Lys Pro Arg Arg Lys Asn Pro Gln Glu Gly
385                 390                 395                 400

Leu Tyr Asn Glu Leu Gln Lys Asp Lys Met Ala Glu Ala Tyr Ser Glu
                405                 410                 415

Ile Gly Met Lys Gly Glu Arg Arg Arg Gly Lys Gly His Asp Gly Leu
            420                 425                 430

Tyr Gln Gly Leu Ser Thr Ala Thr Lys Asp Thr Tyr Asp Ala Leu His
        435                 440                 445

Met Gln Ala Leu Pro Pro Arg
    450                 455

<210> SEQ ID NO 26
<211> LENGTH: 458
<212> TYPE: PRT
<213> ORGANISM: artificial sequence
<220> FEATURE:
<223> OTHER INFORMATION: A1-v2 polypeptide CAR sequence

<400> SEQUENCE: 26

Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Pro Glu Leu
            20                  25                  30

Lys Lys Pro Gly Glu Thr Val Lys Ile Ser Cys Lys Ala Ser Gly Tyr
        35                  40                  45

Thr Phe Thr Asn Phe Gly Met Asn Trp Val Lys Gln Gly Pro Gly Glu
    50                  55                  60

Gly Leu Lys Trp Met Gly Trp Ile Asn Thr Asn Thr Gly Glu Pro Arg
65                  70                  75                  80

Tyr Ala Glu Glu Phe Lys Gly Arg Phe Ala Phe Ser Leu Glu Thr Thr
                85                  90                  95

Ala Ser Thr Ala Tyr Leu Gln Ile Asn Asn Leu Lys Asn Glu Asp Thr
            100                 105                 110

Ala Thr Tyr Phe Cys Ala Arg Asp Trp Asp Gly Ala Tyr Phe Phe Asp
        115                 120                 125

Tyr Trp Gly Gln Gly Thr Thr Leu Thr Val Ser Ser Gly Gly Gly Ser
    130                 135                 140

Gly Gly Gly Gly Ser Gly Gly Gly Ser Ser Ile Val Met Thr Gln
145                 150                 155                 160

Thr Pro Lys Phe Leu Leu Val Ser Ala Gly Asp Arg Val Thr Ile Thr
                165                 170                 175

Cys Lys Ala Ser Gln Ser Val Ser Asn Asp Val Ala Trp Tyr Gln Gln
            180                 185                 190

Lys Pro Gly Gln Ser Pro Lys Leu Leu Ile Asn Phe Ala Thr Asn Arg
        195                 200                 205

Tyr Thr Gly Val Pro Asn Arg Phe Thr Gly Ser Gly Tyr Gly Thr Asp
    210                 215                 220

Phe Thr Phe Thr Ile Ser Thr Val Gln Ala Glu Asp Leu Ala Leu Tyr
225                 230                 235                 240

Phe Cys Gln Gln Asp Tyr Ser Ser Pro Trp Thr Phe Gly Gly Gly Thr
                245                 250                 255

Lys Leu Glu Ile Lys Gly Leu Ala Val Ser Thr Ile Ser Ser Phe Phe
            260                 265                 270

```
Pro Pro Gly Tyr Gln Ile Ile Ser Phe Phe Leu Ala Leu Thr Ser Thr
            275                 280                 285

Ala Leu Leu Phe Leu Leu Phe Phe Leu Thr Leu Arg Phe Ser Val Val
        290                 295                 300

Lys Arg Gly Arg Lys Lys Leu Leu Tyr Ile Phe Lys Gln Pro Phe Met
305                 310                 315                 320

Arg Pro Val Gln Thr Thr Gln Glu Glu Asp Gly Cys Ser Cys Arg Phe
                325                 330                 335

Pro Glu Glu Glu Glu Gly Gly Cys Glu Leu Arg Val Lys Phe Ser Arg
            340                 345                 350

Ser Ala Asp Ala Pro Ala Tyr Gln Gln Gly Gln Asn Gln Leu Tyr Asn
        355                 360                 365

Glu Leu Asn Leu Gly Arg Arg Glu Glu Tyr Asp Val Leu Asp Lys Arg
    370                 375                 380

Arg Gly Arg Asp Pro Glu Met Gly Gly Lys Pro Arg Arg Lys Asn Pro
385                 390                 395                 400

Gln Glu Gly Leu Tyr Asn Glu Leu Gln Lys Asp Lys Met Ala Glu Ala
                405                 410                 415

Tyr Ser Glu Ile Gly Met Lys Gly Glu Arg Arg Arg Gly Lys Gly His
            420                 425                 430

Asp Gly Leu Tyr Gln Gly Leu Ser Thr Ala Thr Lys Asp Thr Tyr Asp
        435                 440                 445

Ala Leu His Met Gln Ala Leu Pro Pro Arg
    450                 455

<210> SEQ ID NO 27
<211> LENGTH: 484
<212> TYPE: PRT
<213> ORGANISM: artificial sequence
<220> FEATURE:
<223> OTHER INFORMATION: A1-v3 polypeptide CAR sequence

<400> SEQUENCE: 27

Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Pro Glu Leu
            20                  25                  30

Lys Lys Pro Gly Glu Thr Val Lys Ile Ser Cys Lys Ala Ser Gly Tyr
        35                  40                  45

Thr Phe Thr Asn Phe Gly Met Asn Trp Val Lys Gln Gly Pro Gly Glu
    50                  55                  60

Gly Leu Lys Trp Met Gly Trp Ile Asn Thr Asn Thr Gly Glu Pro Arg
65                  70                  75                  80

Tyr Ala Glu Glu Phe Lys Gly Arg Phe Ala Phe Ser Leu Glu Thr Thr
                85                  90                  95

Ala Ser Thr Ala Tyr Leu Gln Ile Asn Asn Leu Lys Asn Glu Asp Thr
            100                 105                 110

Ala Thr Tyr Phe Cys Ala Arg Asp Trp Asp Gly Ala Tyr Phe Phe Asp
        115                 120                 125

Tyr Trp Gly Gln Gly Thr Thr Leu Thr Val Ser Ser Gly Gly Gly Ser
    130                 135                 140

Gly Gly Gly Gly Ser Gly Gly Gly Ser Ser Ile Val Met Thr Gln
145                 150                 155                 160

Thr Pro Lys Phe Leu Leu Val Ser Ala Gly Asp Arg Val Thr Ile Thr
                165                 170                 175
```

Cys Lys Ala Ser Gln Ser Val Ser Asn Asp Val Ala Trp Tyr Gln Gln
             180                 185                 190

Lys Pro Gly Gln Ser Pro Lys Leu Leu Ile Asn Phe Ala Thr Asn Arg
             195                 200                 205

Tyr Thr Gly Val Pro Asn Arg Phe Thr Gly Ser Gly Tyr Gly Thr Asp
             210                 215                 220

Phe Thr Phe Thr Ile Ser Thr Val Gln Ala Glu Asp Leu Ala Leu Tyr
225                 230                 235                 240

Phe Cys Gln Gln Asp Tyr Ser Ser Pro Trp Thr Phe Gly Gly Gly Thr
                 245                 250                 255

Lys Leu Glu Ile Lys Thr Thr Thr Pro Ala Pro Arg Pro Pro Thr Pro
             260                 265                 270

Ala Pro Thr Ile Ala Ser Gln Pro Leu Ser Leu Arg Pro Glu Ala Cys
             275                 280                 285

Arg Pro Ala Ala Gly Gly Ala Val His Thr Arg Gly Leu Asp Phe Ala
             290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
                 325                 330                 335

Leu Leu Tyr Ile Phe Lys Gln Pro Phe Met Arg Pro Val Gln Thr Thr
             340                 345                 350

Gln Glu Glu Asp Gly Cys Ser Cys Arg Phe Pro Glu Glu Glu Glu Gly
             355                 360                 365

Gly Cys Glu Leu Arg Val Lys Phe Ser Arg Ser Ala Asp Ala Pro Ala
             370                 375                 380

Tyr Gln Gln Gly Gln Asn Gln Leu Tyr Asn Glu Leu Asn Leu Gly Arg
385                 390                 395                 400

Arg Glu Glu Tyr Asp Val Leu Asp Lys Arg Arg Gly Arg Asp Pro Glu
                 405                 410                 415

Met Gly Gly Lys Pro Arg Arg Lys Asn Pro Gln Glu Gly Leu Tyr Asn
             420                 425                 430

Glu Leu Gln Lys Asp Lys Met Ala Glu Ala Tyr Ser Glu Ile Gly Met
             435                 440                 445

Lys Gly Glu Arg Arg Arg Gly Lys Gly His Asp Gly Leu Tyr Gln Gly
             450                 455                 460

Leu Ser Thr Ala Thr Lys Asp Thr Tyr Asp Ala Leu His Met Gln Ala
465                 470                 475                 480

Leu Pro Pro Arg

<210> SEQ ID NO 28
<211> LENGTH: 487
<212> TYPE: PRT
<213> ORGANISM: artificial sequence
<220> FEATURE:
<223> OTHER INFORMATION: A1-v4 polypeptide CAR sequence

<400> SEQUENCE: 28

Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Pro Glu Leu
             20                  25                  30

Lys Lys Pro Gly Glu Thr Val Lys Ile Ser Cys Lys Ala Ser Gly Tyr
             35                  40                  45

-continued

```
Thr Phe Thr Asn Phe Gly Met Asn Trp Val Lys Gln Gly Pro Gly Glu
 50                  55                  60
Gly Leu Lys Trp Met Gly Trp Ile Asn Thr Asn Thr Gly Glu Pro Arg
 65                  70                  75                  80
Tyr Ala Glu Glu Phe Lys Gly Arg Phe Ala Phe Ser Leu Glu Thr Thr
                 85                  90                  95
Ala Ser Thr Ala Tyr Leu Gln Ile Asn Asn Leu Lys Asn Glu Asp Thr
                100                 105                 110
Ala Thr Tyr Phe Cys Ala Arg Asp Trp Asp Gly Ala Tyr Phe Phe Asp
                115                 120                 125
Tyr Trp Gly Gln Gly Thr Thr Leu Thr Val Ser Ser Gly Gly Gly Ser
130                 135                 140
Gly Gly Gly Gly Ser Gly Gly Gly Ser Ser Ile Val Met Thr Gln
145                 150                 155                 160
Thr Pro Lys Phe Leu Leu Val Ser Ala Gly Asp Arg Val Thr Ile Thr
                165                 170                 175
Cys Lys Ala Ser Gln Ser Val Ser Asn Asp Val Ala Trp Tyr Gln Gln
                180                 185                 190
Lys Pro Gly Gln Ser Pro Lys Leu Leu Ile Asn Phe Ala Thr Asn Arg
                195                 200                 205
Tyr Thr Gly Val Pro Asn Arg Phe Thr Gly Ser Gly Tyr Gly Thr Asp
210                 215                 220
Phe Thr Phe Thr Ile Ser Thr Val Gln Ala Glu Asp Leu Ala Leu Tyr
225                 230                 235                 240
Phe Cys Gln Gln Asp Tyr Ser Ser Pro Trp Thr Phe Gly Gly Gly Thr
                245                 250                 255
Lys Leu Glu Ile Lys Thr Thr Thr Pro Ala Pro Arg Pro Pro Thr Pro
                260                 265                 270
Ala Pro Thr Ile Ala Ser Gln Pro Leu Ser Leu Arg Pro Glu Ala Cys
                275                 280                 285
Arg Pro Ala Ala Gly Gly Ala Val His Thr Arg Gly Leu Asp Phe Ala
290                 295                 300
Cys Asp Ile Ile Ser Phe Phe Leu Ala Leu Thr Ser Thr Ala Leu Leu
305                 310                 315                 320
Phe Leu Leu Phe Phe Leu Thr Leu Arg Phe Ser Val Val Lys Arg Gly
                325                 330                 335
Arg Lys Lys Leu Leu Tyr Ile Phe Lys Gln Pro Phe Met Arg Pro Val
                340                 345                 350
Gln Thr Thr Gln Glu Glu Asp Gly Cys Ser Cys Arg Phe Pro Glu Glu
                355                 360                 365
Glu Glu Gly Gly Cys Glu Leu Arg Val Lys Phe Ser Arg Ser Ala Asp
370                 375                 380
Ala Pro Ala Tyr Gln Gln Gly Gln Asn Gln Leu Tyr Asn Glu Leu Asn
385                 390                 395                 400
Leu Gly Arg Arg Glu Glu Tyr Asp Val Leu Asp Lys Arg Arg Gly Arg
                405                 410                 415
Asp Pro Glu Met Gly Gly Lys Pro Arg Arg Lys Asn Pro Gln Glu Gly
                420                 425                 430
Leu Tyr Asn Glu Leu Gln Lys Asp Lys Met Ala Glu Ala Tyr Ser Glu
                435                 440                 445
Ile Gly Met Lys Gly Glu Arg Arg Arg Gly Lys Gly His Asp Gly Leu
                450                 455                 460
Tyr Gln Gly Leu Ser Thr Ala Thr Lys Asp Thr Tyr Asp Ala Leu His
```

Met Gln Ala Leu Pro Pro Arg
            485

<210> SEQ ID NO 29
<211> LENGTH: 670
<212> TYPE: PRT
<213> ORGANISM: artificial sequence
<220> FEATURE:
<223> OTHER INFORMATION: A1-v5 polypeptide CAR sequence

<400> SEQUENCE: 29

Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Pro Glu Leu
            20                  25                  30

Lys Lys Pro Gly Glu Thr Val Lys Ile Ser Cys Lys Ala Ser Gly Tyr
        35                  40                  45

Thr Phe Thr Asn Phe Gly Met Asn Trp Val Lys Gln Gly Pro Gly Glu
    50                  55                  60

Gly Leu Lys Trp Met Gly Trp Ile Asn Thr Asn Thr Gly Glu Pro Arg
65                  70                  75                  80

Tyr Ala Glu Glu Phe Lys Gly Arg Phe Ala Phe Ser Leu Glu Thr Thr
                85                  90                  95

Ala Ser Thr Ala Tyr Leu Gln Ile Asn Asn Leu Lys Asn Glu Asp Thr
            100                 105                 110

Ala Thr Tyr Phe Cys Ala Arg Asp Trp Asp Gly Ala Tyr Phe Phe Asp
        115                 120                 125

Tyr Trp Gly Gln Gly Thr Thr Leu Thr Val Ser Ser Gly Gly Gly Ser
    130                 135                 140

Gly Gly Gly Gly Ser Gly Gly Gly Ser Ser Ile Val Met Thr Gln
145                 150                 155                 160

Thr Pro Lys Phe Leu Leu Val Ser Ala Gly Asp Arg Val Thr Ile Thr
                165                 170                 175

Cys Lys Ala Ser Gln Ser Val Ser Asn Asp Val Ala Trp Tyr Gln Gln
            180                 185                 190

Lys Pro Gly Gln Ser Pro Lys Leu Leu Ile Asn Phe Ala Thr Asn Arg
        195                 200                 205

Tyr Thr Gly Val Pro Asn Arg Phe Thr Gly Ser Gly Tyr Gly Thr Asp
    210                 215                 220

Phe Thr Phe Thr Ile Ser Thr Val Gln Ala Glu Asp Leu Ala Leu Tyr
225                 230                 235                 240

Phe Cys Gln Gln Asp Tyr Ser Ser Pro Trp Thr Phe Gly Gly Gly Thr
                245                 250                 255

Lys Leu Glu Ile Lys Glu Pro Lys Ser Pro Asp Lys Thr His Thr Cys
            260                 265                 270

Pro Pro Cys Pro Ala Pro Pro Val Ala Gly Pro Ser Val Phe Leu Phe
        275                 280                 285

Pro Pro Lys Pro Lys Asp Thr Leu Met Ile Ala Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr

```
                    340                 345                 350
Val Leu His Gln Asp Trp Leu Asn Gly Lys Glu Tyr Lys Cys Lys Val
                355                 360                 365

Ser Asn Lys Ala Leu Pro Ala Pro Ile Glu Lys Thr Ile Ser Lys Ala
            370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
                435                 440                 445

Phe Phe Leu Tyr Ser Lys Leu Thr Val Asp Lys Ser Arg Trp Gln Gln
            450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys Ile Tyr Ile Trp
                485                 490                 495

Ala Pro Leu Ala Gly Thr Cys Gly Val Leu Leu Leu Ser Leu Val Ile
            500                 505                 510

Thr Leu Tyr Cys Lys Arg Gly Arg Lys Lys Leu Leu Tyr Ile Phe Lys
            515                 520                 525

Gln Pro Phe Met Arg Pro Val Gln Thr Thr Gln Glu Glu Asp Gly Cys
        530                 535                 540

Ser Cys Arg Phe Pro Glu Glu Glu Glu Gly Gly Cys Glu Leu Arg Val
545                 550                 555                 560

Lys Phe Ser Arg Ser Ala Asp Ala Pro Ala Tyr Gln Gln Gly Gln Asn
                565                 570                 575

Gln Leu Tyr Asn Glu Leu Asn Leu Gly Arg Arg Glu Glu Tyr Asp Val
            580                 585                 590

Leu Asp Lys Arg Arg Gly Arg Asp Pro Glu Met Gly Gly Lys Pro Arg
        595                 600                 605

Arg Lys Asn Pro Gln Glu Gly Leu Tyr Asn Glu Leu Gln Lys Asp Lys
    610                 615                 620

Met Ala Glu Ala Tyr Ser Glu Ile Gly Met Lys Gly Glu Arg Arg Arg
625                 630                 635                 640

Gly Lys Gly His Asp Gly Leu Tyr Gln Gly Leu Ser Thr Ala Thr Lys
                645                 650                 655

Asp Thr Tyr Asp Ala Leu His Met Gln Ala Leu Pro Pro Arg
            660                 665                 670

<210> SEQ ID NO 30
<211> LENGTH: 673
<212> TYPE: PRT
<213> ORGANISM: artificial sequence
<220> FEATURE:
<223> OTHER INFORMATION: A1-v6 polypeptide CAR sequence

<400> SEQUENCE: 30

Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Pro Glu Leu
            20                  25                  30

Lys Lys Pro Gly Glu Thr Val Lys Ile Ser Cys Lys Ala Ser Gly Tyr
```

```
                35                  40                  45
Thr Phe Thr Asn Phe Gly Met Asn Trp Val Lys Gln Gly Pro Gly Glu
 50                  55                  60

Gly Leu Lys Trp Met Gly Trp Ile Asn Thr Asn Thr Gly Glu Pro Arg
 65                  70                  75                  80

Tyr Ala Glu Glu Phe Lys Gly Arg Phe Ala Phe Ser Leu Glu Thr Thr
                 85                  90                  95

Ala Ser Thr Ala Tyr Leu Gln Ile Asn Asn Leu Lys Asn Glu Asp Thr
                100                 105                 110

Ala Thr Tyr Phe Cys Ala Arg Asp Trp Asp Gly Ala Tyr Phe Phe Asp
                115                 120                 125

Tyr Trp Gly Gln Gly Thr Thr Leu Thr Val Ser Ser Gly Gly Gly Ser
                130                 135                 140

Gly Gly Gly Gly Ser Gly Gly Gly Ser Ser Ile Val Met Thr Gln
145                 150                 155                 160

Thr Pro Lys Phe Leu Leu Val Ser Ala Gly Asp Arg Val Thr Ile Thr
                165                 170                 175

Cys Lys Ala Ser Gln Ser Val Ser Asn Asp Val Ala Trp Tyr Gln Gln
                180                 185                 190

Lys Pro Gly Gln Ser Pro Lys Leu Leu Ile Asn Phe Ala Thr Asn Arg
                195                 200                 205

Tyr Thr Gly Val Pro Asn Arg Phe Thr Gly Ser Gly Tyr Gly Thr Asp
                210                 215                 220

Phe Thr Phe Thr Ile Ser Thr Val Gln Ala Glu Asp Leu Ala Leu Tyr
225                 230                 235                 240

Phe Cys Gln Gln Asp Tyr Ser Ser Pro Trp Thr Phe Gly Gly Gly Thr
                245                 250                 255

Lys Leu Glu Ile Lys Glu Pro Lys Ser Pro Asp Lys Thr His Thr Cys
                260                 265                 270

Pro Pro Cys Pro Ala Pro Pro Val Ala Gly Pro Ser Val Phe Leu Phe
                275                 280                 285

Pro Pro Lys Pro Lys Asp Thr Leu Met Ile Ala Arg Thr Pro Glu Val
290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
                340                 345                 350

Val Leu His Gln Asp Trp Leu Asn Gly Lys Glu Tyr Lys Cys Lys Val
                355                 360                 365

Ser Asn Lys Ala Leu Pro Ala Pro Ile Glu Lys Thr Ile Ser Lys Ala
                370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
                420                 425                 430

Glu Asn Asn Tyr Lys Thr Thr Pro Pro Val Leu Asp Ser Asp Gly Ser
                435                 440                 445

Phe Phe Leu Tyr Ser Lys Leu Thr Val Asp Lys Ser Arg Trp Gln Gln
450                 455                 460
```

```
Gly Asn Val Phe Ser Cys Ser Val Met His Glu Ala Leu His Asn His
465                 470                 475                 480

Tyr Thr Gln Lys Ser Leu Ser Leu Ser Pro Gly Lys Ile Ile Ser Phe
                485                 490                 495

Phe Leu Ala Leu Thr Ser Thr Ala Leu Leu Phe Leu Leu Phe Phe Leu
            500                 505                 510

Thr Leu Arg Phe Ser Val Val Lys Arg Gly Arg Lys Lys Leu Leu Tyr
        515                 520                 525

Ile Phe Lys Gln Pro Phe Met Arg Pro Val Gln Thr Thr Gln Glu Glu
    530                 535                 540

Asp Gly Cys Ser Cys Arg Phe Pro Glu Glu Glu Glu Gly Gly Cys Glu
545                 550                 555                 560

Leu Arg Val Lys Phe Ser Arg Ser Ala Asp Ala Pro Ala Tyr Gln Gln
                565                 570                 575

Gly Gln Asn Gln Leu Tyr Asn Glu Leu Asn Leu Gly Arg Arg Glu Glu
            580                 585                 590

Tyr Asp Val Leu Asp Lys Arg Arg Gly Arg Asp Pro Glu Met Gly Gly
        595                 600                 605

Lys Pro Arg Arg Lys Asn Pro Gln Glu Gly Leu Tyr Asn Glu Leu Gln
610                 615                 620

Lys Asp Lys Met Ala Glu Ala Tyr Ser Glu Ile Gly Met Lys Gly Glu
625                 630                 635                 640

Arg Arg Arg Gly Lys Gly His Asp Gly Leu Tyr Gln Gly Leu Ser Thr
                645                 650                 655

Ala Thr Lys Asp Thr Tyr Asp Ala Leu His Met Gln Ala Leu Pro Pro
            660                 665                 670

Arg

<210> SEQ ID NO 31
<211> LENGTH: 455
<212> TYPE: PRT
<213> ORGANISM: artificial sequence
<220> FEATURE:
<223> OTHER INFORMATION: A2-v1 polypeptide CAR sequence

<400> SEQUENCE: 31

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Arg Pro Glu Leu
            20                  25                  30

Val Lys Pro Gly Ala Ser Val Lys Met Ser Cys Lys Ala Ser Gly Tyr
        35                  40                  45

Thr Phe Thr Asp Tyr Val Ile Ser Trp Val Lys Gln Arg Thr Gly Gln
    50                  55                  60

Gly Leu Glu Trp Ile Gly Glu Ile Tyr Pro Gly Ser Asn Ser Ile Tyr
65                  70                  75                  80

Tyr Asn Glu Lys Phe Lys Gly Arg Ala Thr Leu Thr Ala Asp Lys Ser
                85                  90                  95

Ser Ser Thr Ala Tyr Met Gln Leu Ser Ser Leu Thr Ser Glu Asp Ser
            100                 105                 110

Ala Val Tyr Phe Cys Ala Met Gly Gly Asn Tyr Gly Phe Asp Tyr Trp
        115                 120                 125

Gly Gln Gly Thr Thr Leu Thr Val Ser Ser Gly Gly Gly Gly Ser Gly
    130                 135                 140
```

Gly Gly Gly Ser Gly Gly Gly Ser Gln Ile Val Leu Thr Gln Ser
145                 150                 155                 160

Pro Ala Ile Met Ser Ala Ser Leu Gly Glu Arg Val Thr Leu Thr Cys
            165                 170                 175

Thr Ala Ser Ser Ser Val Asn Ser Asn Tyr Leu His Trp Tyr Gln Gln
            180                 185                 190

Lys Pro Gly Ser Ser Pro Lys Leu Trp Ile Tyr Ser Thr Ser Asn Leu
        195                 200                 205

Ala Ser Gly Val Pro Ala Arg Phe Ser Gly Ser Gly Ser Gly Thr Ser
210                 215                 220

Tyr Ser Leu Thr Ile Ser Ser Met Glu Ala Glu Asp Ala Ala Thr Tyr
225                 230                 235                 240

Tyr Cys His Gln Tyr His Arg Ser Pro Leu Thr Phe Gly Ala Gly Thr
                245                 250                 255

Lys Leu Glu Leu Lys Gly Leu Ala Val Ser Thr Ile Ser Ser Phe Phe
        260                 265                 270

Pro Pro Gly Tyr Gln Ile Tyr Ile Trp Ala Pro Leu Ala Gly Thr Cys
        275                 280                 285

Gly Val Leu Leu Leu Ser Leu Val Ile Thr Leu Tyr Cys Lys Arg Gly
290                 295                 300

Arg Lys Lys Leu Leu Tyr Ile Phe Lys Gln Pro Phe Met Arg Pro Val
305                 310                 315                 320

Gln Thr Thr Gln Glu Glu Asp Gly Cys Ser Cys Arg Phe Pro Glu Glu
                325                 330                 335

Glu Glu Gly Gly Cys Glu Leu Arg Val Lys Phe Ser Arg Ser Ala Asp
            340                 345                 350

Ala Pro Ala Tyr Gln Gln Gly Gln Asn Gln Leu Tyr Asn Glu Leu Asn
        355                 360                 365

Leu Gly Arg Arg Glu Glu Tyr Asp Val Leu Asp Lys Arg Arg Gly Arg
        370                 375                 380

Asp Pro Glu Met Gly Gly Lys Pro Arg Arg Lys Asn Pro Gln Glu Gly
385                 390                 395                 400

Leu Tyr Asn Glu Leu Gln Lys Asp Lys Met Ala Glu Ala Tyr Ser Glu
            405                 410                 415

Ile Gly Met Lys Gly Glu Arg Arg Arg Gly Lys Gly His Asp Gly Leu
            420                 425                 430

Tyr Gln Gly Leu Ser Thr Ala Thr Lys Asp Thr Tyr Asp Ala Leu His
        435                 440                 445

Met Gln Ala Leu Pro Pro Arg
    450                 455

<210> SEQ ID NO 32
<211> LENGTH: 458
<212> TYPE: PRT
<213> ORGANISM: artificial sequence
<220> FEATURE:
<223> OTHER INFORMATION: A2-v2 polypeptide CAR sequence

<400> SEQUENCE: 32

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Arg Pro Glu Leu
            20                  25                  30

Val Lys Pro Gly Ala Ser Val Lys Met Ser Cys Lys Ala Ser Gly Tyr
        35                  40                  45

```
Thr Phe Thr Asp Tyr Val Ile Ser Trp Val Lys Gln Arg Thr Gly Gln
 50                  55                  60

Gly Leu Glu Trp Ile Gly Glu Ile Tyr Pro Gly Ser Asn Ser Ile Tyr
 65                  70                  75                  80

Tyr Asn Glu Lys Phe Lys Gly Arg Ala Thr Leu Thr Ala Asp Lys Ser
                 85                  90                  95

Ser Ser Thr Ala Tyr Met Gln Leu Ser Ser Leu Thr Ser Glu Asp Ser
            100                 105                 110

Ala Val Tyr Phe Cys Ala Met Gly Gly Asn Tyr Gly Phe Asp Tyr Trp
            115                 120                 125

Gly Gln Gly Thr Thr Leu Thr Val Ser Ser Gly Gly Gly Gly Ser Gly
130                 135                 140

Gly Gly Gly Ser Gly Gly Gly Ser Gln Ile Val Leu Thr Gln Ser
145                 150                 155                 160

Pro Ala Ile Met Ser Ala Ser Leu Gly Glu Arg Val Thr Leu Thr Cys
                165                 170                 175

Thr Ala Ser Ser Ser Val Asn Ser Asn Tyr Leu His Trp Tyr Gln Gln
            180                 185                 190

Lys Pro Gly Ser Ser Pro Lys Leu Trp Ile Tyr Ser Thr Ser Asn Leu
                195                 200                 205

Ala Ser Gly Val Pro Ala Arg Phe Ser Gly Ser Gly Ser Gly Thr Ser
210                 215                 220

Tyr Ser Leu Thr Ile Ser Ser Met Glu Ala Glu Asp Ala Ala Thr Tyr
225                 230                 235                 240

Tyr Cys His Gln Tyr His Arg Ser Pro Leu Thr Phe Gly Ala Gly Thr
                245                 250                 255

Lys Leu Glu Leu Lys Gly Leu Ala Val Ser Thr Ile Ser Ser Phe Phe
            260                 265                 270

Pro Pro Gly Tyr Gln Ile Ile Ser Phe Phe Leu Ala Leu Thr Ser Thr
                275                 280                 285

Ala Leu Leu Phe Leu Leu Phe Phe Leu Thr Leu Arg Phe Ser Val Val
            290                 295                 300

Lys Arg Gly Arg Lys Lys Leu Leu Tyr Ile Phe Lys Gln Pro Phe Met
305                 310                 315                 320

Arg Pro Val Gln Thr Thr Gln Glu Glu Asp Gly Cys Ser Cys Arg Phe
                325                 330                 335

Pro Glu Glu Glu Glu Gly Gly Cys Glu Leu Arg Val Lys Phe Ser Arg
                340                 345                 350

Ser Ala Asp Ala Pro Ala Tyr Gln Gln Gly Gln Asn Gln Leu Tyr Asn
            355                 360                 365

Glu Leu Asn Leu Gly Arg Arg Glu Glu Tyr Asp Val Leu Asp Lys Arg
370                 375                 380

Arg Gly Arg Asp Pro Glu Met Gly Gly Lys Pro Arg Arg Lys Asn Pro
385                 390                 395                 400

Gln Glu Gly Leu Tyr Asn Glu Leu Gln Lys Asp Lys Met Ala Glu Ala
                405                 410                 415

Tyr Ser Glu Ile Gly Met Lys Gly Glu Arg Arg Arg Gly Lys Gly His
            420                 425                 430

Asp Gly Leu Tyr Gln Gly Leu Ser Thr Ala Thr Lys Asp Thr Tyr Asp
            435                 440                 445

Ala Leu His Met Gln Ala Leu Pro Pro Arg
450                 455
```

<210> SEQ ID NO 33
<211> LENGTH: 484
<212> TYPE: PRT
<213> ORGANISM: artificial sequence
<220> FEATURE:
<223> OTHER INFORMATION: A2-v3 polypeptide CAR sequence

<400> SEQUENCE: 33

```
Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Arg Pro Glu Leu
                20                  25                  30

Val Lys Pro Gly Ala Ser Val Lys Met Ser Cys Lys Ala Ser Gly Tyr
            35                  40                  45

Thr Phe Thr Asp Tyr Val Ile Ser Trp Val Lys Gln Arg Thr Gly Gln
        50                  55                  60

Gly Leu Glu Trp Ile Gly Glu Ile Tyr Pro Gly Ser Asn Ser Ile Tyr
65                  70                  75                  80

Tyr Asn Glu Lys Phe Lys Gly Arg Ala Thr Leu Thr Ala Asp Lys Ser
                85                  90                  95

Ser Ser Thr Ala Tyr Met Gln Leu Ser Ser Leu Thr Ser Glu Asp Ser
            100                 105                 110

Ala Val Tyr Phe Cys Ala Met Gly Gly Asn Tyr Gly Phe Asp Tyr Trp
        115                 120                 125

Gly Gln Gly Thr Thr Leu Thr Val Ser Ser Gly Gly Gly Gly Ser Gly
130                 135                 140

Gly Gly Gly Ser Gly Gly Gly Ser Gln Ile Val Leu Thr Gln Ser
145                 150                 155                 160

Pro Ala Ile Met Ser Ala Ser Leu Gly Glu Arg Val Thr Leu Thr Cys
                165                 170                 175

Thr Ala Ser Ser Ser Val Asn Ser Asn Tyr Leu His Trp Tyr Gln Gln
            180                 185                 190

Lys Pro Gly Ser Ser Pro Lys Leu Trp Ile Tyr Ser Thr Ser Asn Leu
        195                 200                 205

Ala Ser Gly Val Pro Ala Arg Phe Ser Gly Ser Gly Ser Gly Thr Ser
    210                 215                 220

Tyr Ser Leu Thr Ile Ser Ser Met Glu Ala Glu Asp Ala Ala Thr Tyr
225                 230                 235                 240

Tyr Cys His Gln Tyr His Arg Ser Pro Leu Thr Phe Gly Ala Gly Thr
                245                 250                 255

Lys Leu Glu Leu Lys Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
        275                 280                 285

Arg Pro Ala Ala Gly Gly Ala Val His Thr Arg Gly Leu Asp Phe Ala
    290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
                325                 330                 335

Leu Leu Tyr Ile Phe Lys Gln Pro Phe Met Arg Pro Val Gln Thr Thr
            340                 345                 350

Gln Glu Glu Asp Gly Cys Ser Cys Arg Phe Pro Glu Glu Glu Glu Gly
        355                 360                 365

Gly Cys Glu Leu Arg Val Lys Phe Ser Arg Ser Ala Asp Ala Pro Ala
```

```
                370                 375                 380
Tyr Gln Gln Gly Gln Asn Gln Leu Tyr Asn Glu Leu Asn Leu Gly Arg
385                 390                 395                 400

Arg Glu Glu Tyr Asp Val Leu Asp Lys Arg Arg Gly Arg Asp Pro Glu
                405                 410                 415

Met Gly Gly Lys Pro Arg Arg Lys Asn Pro Gln Glu Gly Leu Tyr Asn
                420                 425                 430

Glu Leu Gln Lys Asp Lys Met Ala Glu Ala Tyr Ser Glu Ile Gly Met
            435                 440                 445

Lys Gly Glu Arg Arg Arg Gly Lys Gly His Asp Gly Leu Tyr Gln Gly
        450                 455                 460

Leu Ser Thr Ala Thr Lys Asp Thr Tyr Asp Ala Leu His Met Gln Ala
465                 470                 475                 480

Leu Pro Pro Arg

<210> SEQ ID NO 34
<211> LENGTH: 487
<212> TYPE: PRT
<213> ORGANISM: artificial sequence
<220> FEATURE:
<223> OTHER INFORMATION: A2-v4 polypeptide CAR sequence

<400> SEQUENCE: 34

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Arg Pro Glu Leu
                20                  25                  30

Val Lys Pro Gly Ala Ser Val Lys Met Ser Cys Lys Ala Ser Gly Tyr
            35                  40                  45

Thr Phe Thr Asp Tyr Val Ile Ser Trp Val Lys Gln Arg Thr Gly Gln
        50                  55                  60

Gly Leu Glu Trp Ile Gly Glu Ile Tyr Pro Gly Ser Asn Ser Ile Tyr
65                  70                  75                  80

Tyr Asn Glu Lys Phe Lys Gly Arg Ala Thr Leu Thr Ala Asp Lys Ser
                85                  90                  95

Ser Ser Thr Ala Tyr Met Gln Leu Ser Ser Leu Thr Ser Glu Asp Ser
                100                 105                 110

Ala Val Tyr Phe Cys Ala Met Gly Gly Asn Tyr Gly Phe Asp Tyr Trp
            115                 120                 125

Gly Gln Gly Thr Thr Leu Thr Val Ser Ser Gly Gly Gly Gly Ser Gly
        130                 135                 140

Gly Gly Gly Ser Gly Gly Gly Ser Gln Ile Val Leu Thr Gln Ser
145                 150                 155                 160

Pro Ala Ile Met Ser Ala Ser Leu Gly Glu Arg Val Thr Leu Thr Cys
                165                 170                 175

Thr Ala Ser Ser Ser Val Asn Ser Asn Tyr Leu His Trp Tyr Gln Gln
                180                 185                 190

Lys Pro Gly Ser Ser Pro Lys Leu Trp Ile Tyr Ser Thr Ser Asn Leu
            195                 200                 205

Ala Ser Gly Val Pro Ala Arg Phe Ser Gly Ser Gly Ser Gly Thr Ser
        210                 215                 220

Tyr Ser Leu Thr Ile Ser Ser Met Glu Ala Glu Asp Ala Ala Thr Tyr
225                 230                 235                 240

Tyr Cys His Gln Tyr His Arg Ser Pro Leu Thr Phe Gly Ala Gly Thr
                245                 250                 255
```

```
Lys Leu Glu Leu Lys Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
            275                 280                 285

Arg Pro Ala Ala Gly Gly Ala Val His Thr Arg Gly Leu Asp Phe Ala
290                 295                 300

Cys Asp Ile Ile Ser Phe Phe Leu Ala Leu Thr Ser Thr Ala Leu Leu
305                 310                 315                 320

Phe Leu Leu Phe Phe Leu Thr Leu Arg Phe Ser Val Val Lys Arg Gly
                325                 330                 335

Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
            355                 360                 365

Glu Glu Gly Gly Cys Glu Leu Arg Val Lys Phe Ser Arg Ser Ala Asp
370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
            435                 440                 445

Ile Gly Met Lys Gly Glu Arg Arg Gly Lys Gly His Asp Gly Leu
            450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 35
<211> LENGTH: 670
<212> TYPE: PRT
<213> ORGANISM: artificial sequence
<220> FEATURE:
<223> OTHER INFORMATION: A2-v5 polypeptide CAR sequence

<400> SEQUENCE: 35

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Arg Pro Glu Leu
            20                  25                  30

Val Lys Pro Gly Ala Ser Val Lys Met Ser Cys Lys Ala Ser Gly Tyr
        35                  40                  45

Thr Phe Thr Asp Tyr Val Ile Ser Trp Val Lys Gln Arg Thr Gly Gln
    50                  55                  60

Gly Leu Glu Trp Ile Gly Glu Ile Tyr Pro Gly Ser Asn Ser Ile Tyr
65                  70                  75                  80

Tyr Asn Glu Lys Phe Lys Gly Arg Ala Thr Leu Thr Ala Asp Lys Ser
                85                  90                  95

Ser Ser Thr Ala Tyr Met Gln Leu Ser Ser Leu Thr Ser Glu Asp Ser
            100                 105                 110

Ala Val Tyr Phe Cys Ala Met Gly Gly Asn Tyr Gly Phe Asp Tyr Trp
        115                 120                 125
```

```
Gly Gln Gly Thr Thr Leu Thr Val Ser Ser Gly Gly Gly Ser Gly
    130                 135                 140
Gly Gly Gly Ser Gly Gly Gly Ser Gln Ile Val Leu Thr Gln Ser
145                 150                 155                 160
Pro Ala Ile Met Ser Ala Ser Leu Gly Glu Arg Val Thr Leu Thr Cys
                165                 170                 175
Thr Ala Ser Ser Ser Val Asn Ser Asn Tyr Leu His Trp Tyr Gln Gln
            180                 185                 190
Lys Pro Gly Ser Ser Pro Lys Leu Trp Ile Tyr Ser Thr Ser Asn Leu
        195                 200                 205
Ala Ser Gly Val Pro Ala Arg Phe Ser Gly Ser Gly Ser Gly Thr Ser
    210                 215                 220
Tyr Ser Leu Thr Ile Ser Ser Met Glu Ala Glu Asp Ala Ala Thr Tyr
225                 230                 235                 240
Tyr Cys His Gln Tyr His Arg Ser Pro Leu Thr Phe Gly Ala Gly Thr
                245                 250                 255
Lys Leu Glu Leu Lys Glu Pro Lys Ser Pro Asp Lys Thr His Thr Cys
            260                 265                 270
Pro Pro Cys Pro Ala Pro Pro Val Ala Gly Pro Ser Val Phe Leu Phe
        275                 280                 285
Pro Pro Lys Pro Lys Asp Thr Leu Met Ile Ala Arg Thr Pro Glu Val
    290                 295                 300
Thr Cys Val Val Val Asp Val Ser His Glu Asp Pro Glu Val Lys Phe
305                 310                 315                 320
Asn Trp Tyr Val Asp Gly Val Glu Val His Asn Ala Lys Thr Lys Pro
                325                 330                 335
Arg Glu Glu Gln Tyr Asn Ser Thr Tyr Arg Val Val Ser Val Leu Thr
            340                 345                 350
Val Leu His Gln Asp Trp Leu Asn Gly Lys Glu Tyr Lys Cys Lys Val
        355                 360                 365
Ser Asn Lys Ala Leu Pro Ala Pro Ile Glu Lys Thr Ile Ser Lys Ala
    370                 375                 380
Lys Gly Gln Pro Arg Glu Pro Gln Val Tyr Thr Leu Pro Pro Ser Arg
385                 390                 395                 400
Asp Glu Leu Thr Lys Asn Gln Val Ser Leu Thr Cys Leu Val Lys Gly
                405                 410                 415
Phe Tyr Pro Ser Asp Ile Ala Val Glu Trp Glu Ser Asn Gly Gln Pro
            420                 425                 430
Glu Asn Asn Tyr Lys Thr Thr Pro Pro Val Leu Asp Ser Asp Gly Ser
        435                 440                 445
Phe Phe Leu Tyr Ser Lys Leu Thr Val Asp Lys Ser Arg Trp Gln Gln
    450                 455                 460
Gly Asn Val Phe Ser Cys Ser Val Met His Glu Ala Leu His Asn His
465                 470                 475                 480
Tyr Thr Gln Lys Ser Leu Ser Leu Ser Pro Gly Lys Ile Tyr Ile Trp
                485                 490                 495
Ala Pro Leu Ala Gly Thr Cys Gly Val Leu Leu Leu Ser Leu Val Ile
            500                 505                 510
Thr Leu Tyr Cys Lys Arg Gly Arg Lys Lys Leu Leu Tyr Ile Phe Lys
        515                 520                 525
Gln Pro Phe Met Arg Pro Val Gln Thr Thr Gln Glu Glu Asp Gly Cys
    530                 535                 540
```

Ser Cys Arg Phe Pro Glu Glu Glu Gly Gly Cys Glu Leu Arg Val
545                 550                 555                 560

Lys Phe Ser Arg Ser Ala Asp Ala Pro Ala Tyr Gln Gln Gly Gln Asn
                565                 570                 575

Gln Leu Tyr Asn Glu Leu Asn Leu Gly Arg Arg Glu Glu Tyr Asp Val
                580                 585                 590

Leu Asp Lys Arg Arg Gly Arg Asp Pro Glu Met Gly Gly Lys Pro Arg
            595                 600                 605

Arg Lys Asn Pro Gln Glu Gly Leu Tyr Asn Glu Leu Gln Lys Asp Lys
        610                 615                 620

Met Ala Glu Ala Tyr Ser Glu Ile Gly Met Lys Gly Glu Arg Arg Arg
625                 630                 635                 640

Gly Lys Gly His Asp Gly Leu Tyr Gln Gly Leu Ser Thr Ala Thr Lys
                645                 650                 655

Asp Thr Tyr Asp Ala Leu His Met Gln Ala Leu Pro Pro Arg
                660                 665                 670

<210> SEQ ID NO 36
<211> LENGTH: 673
<212> TYPE: PRT
<213> ORGANISM: artificial sequence
<220> FEATURE:
<223> OTHER INFORMATION: A2-v6 polypeptide CAR sequence

<400> SEQUENCE: 36

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Arg Pro Glu Leu
                20                  25                  30

Val Lys Pro Gly Ala Ser Val Lys Met Ser Cys Lys Ala Ser Gly Tyr
            35                  40                  45

Thr Phe Thr Asp Tyr Val Ile Ser Trp Val Lys Gln Arg Thr Gly Gln
        50                  55                  60

Gly Leu Glu Trp Ile Gly Glu Ile Tyr Pro Gly Ser Asn Ser Ile Tyr
65                  70                  75                  80

Tyr Asn Glu Lys Phe Lys Gly Arg Ala Thr Leu Thr Ala Asp Lys Ser
                85                  90                  95

Ser Ser Thr Ala Tyr Met Gln Leu Ser Ser Leu Thr Ser Glu Asp Ser
            100                 105                 110

Ala Val Tyr Phe Cys Ala Met Gly Gly Asn Tyr Gly Phe Asp Tyr Trp
        115                 120                 125

Gly Gln Gly Thr Thr Leu Thr Val Ser Ser Gly Gly Gly Gly Ser Gly
    130                 135                 140

Gly Gly Gly Ser Gly Gly Gly Ser Gln Ile Val Leu Thr Gln Ser
145                 150                 155                 160

Pro Ala Ile Met Ser Ala Ser Leu Gly Glu Arg Val Thr Leu Thr Cys
                165                 170                 175

Thr Ala Ser Ser Ser Val Asn Ser Asn Tyr Leu His Trp Tyr Gln Gln
            180                 185                 190

Lys Pro Gly Ser Ser Pro Lys Leu Trp Ile Tyr Ser Thr Ser Asn Leu
        195                 200                 205

Ala Ser Gly Val Pro Ala Arg Phe Ser Gly Ser Gly Ser Gly Thr Ser
    210                 215                 220

Tyr Ser Leu Thr Ile Ser Ser Met Glu Ala Glu Asp Ala Ala Thr Tyr
225                 230                 235                 240

```
Tyr Cys His Gln Tyr His Arg Ser Pro Leu Thr Phe Gly Ala Gly Thr
            245                 250                 255
Lys Leu Glu Leu Lys Glu Pro Lys Ser Pro Asp Lys Thr His Thr Cys
        260                 265                 270
Pro Pro Cys Pro Ala Pro Val Ala Gly Pro Ser Val Phe Leu Phe
            275                 280                 285
Pro Pro Lys Pro Lys Asp Thr Leu Met Ile Ala Arg Thr Pro Glu Val
        290                 295                 300
Thr Cys Val Val Val Asp Val Ser His Glu Asp Pro Glu Val Lys Phe
305                 310                 315                 320
Asn Trp Tyr Val Asp Gly Val Glu Val His Asn Ala Lys Thr Lys Pro
            325                 330                 335
Arg Glu Glu Gln Tyr Asn Ser Thr Tyr Arg Val Val Ser Val Leu Thr
            340                 345                 350
Val Leu His Gln Asp Trp Leu Asn Gly Lys Glu Tyr Lys Cys Lys Val
            355                 360                 365
Ser Asn Lys Ala Leu Pro Ala Pro Ile Glu Lys Thr Ile Ser Lys Ala
        370                 375                 380
Lys Gly Gln Pro Arg Glu Pro Gln Val Tyr Thr Leu Pro Pro Ser Arg
385                 390                 395                 400
Asp Glu Leu Thr Lys Asn Gln Val Ser Leu Thr Cys Leu Val Lys Gly
            405                 410                 415
Phe Tyr Pro Ser Asp Ile Ala Val Glu Trp Glu Ser Asn Gly Gln Pro
            420                 425                 430
Glu Asn Asn Tyr Lys Thr Thr Pro Pro Val Leu Asp Ser Asp Gly Ser
        435                 440                 445
Phe Phe Leu Tyr Ser Lys Leu Thr Val Asp Lys Ser Arg Trp Gln Gln
    450                 455                 460
Gly Asn Val Phe Ser Cys Ser Val Met His Glu Ala Leu His Asn His
465                 470                 475                 480
Tyr Thr Gln Lys Ser Leu Ser Leu Ser Pro Gly Lys Ile Ile Ser Phe
            485                 490                 495
Phe Leu Ala Leu Thr Ser Thr Ala Leu Leu Phe Leu Leu Phe Phe Leu
        500                 505                 510
Thr Leu Arg Phe Ser Val Val Lys Arg Gly Arg Lys Lys Leu Leu Tyr
        515                 520                 525
Ile Phe Lys Gln Pro Phe Met Arg Pro Val Gln Thr Thr Gln Glu Glu
        530                 535                 540
Asp Gly Cys Ser Cys Arg Phe Pro Glu Glu Glu Glu Gly Gly Cys Glu
545                 550                 555                 560
Leu Arg Val Lys Phe Ser Arg Ser Ala Asp Ala Pro Ala Tyr Gln Gln
            565                 570                 575
Gly Gln Asn Gln Leu Tyr Asn Glu Leu Asn Leu Gly Arg Arg Glu Glu
        580                 585                 590
Tyr Asp Val Leu Asp Lys Arg Gly Arg Asp Pro Glu Met Gly Gly
            595                 600                 605
Lys Pro Arg Arg Lys Asn Pro Gln Glu Gly Leu Tyr Asn Glu Leu Gln
        610                 615                 620
Lys Asp Lys Met Ala Glu Ala Tyr Ser Glu Ile Gly Met Lys Gly Glu
625                 630                 635                 640
Arg Arg Arg Gly Lys Gly His Asp Gly Leu Tyr Gln Gly Leu Ser Thr
            645                 650                 655
Ala Thr Lys Asp Thr Tyr Asp Ala Leu His Met Gln Ala Leu Pro Pro
```

Arg

<210> SEQ ID NO 37
<211> LENGTH: 459
<212> TYPE: PRT
<213> ORGANISM: artificial sequence
<220> FEATURE:
<223> OTHER INFORMATION: A3-v1 polypeptide CAR sequence

<400> SEQUENCE: 37

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Lys Gly Ser Leu Lys Leu Ser Cys Ala Ala Ser Gly Phe
        35                  40                  45

Thr Phe Asn Thr Tyr Ala Met Asn Trp Val Arg Gln Ala Pro Gly Lys
    50                  55                  60

Gly Leu Glu Trp Val Ala Arg Ile Arg Ser Lys Ser Asn Asn Tyr Ala
65                  70                  75                  80

Thr Tyr Tyr Ala Asp Ser Val Lys Asp Arg Phe Thr Ile Ser Arg Asp
                85                  90                  95

Asp Ser Gln Ser Met Leu Tyr Leu Gln Met Asn Asn Leu Lys Thr Glu
            100                 105                 110

Asp Thr Ala Met Tyr Tyr Cys Val Arg Gln Trp Asp Tyr Asp Val Arg
        115                 120                 125

Ala Met Asn Tyr Trp Gly Gln Gly Thr Ser Val Thr Val Ser Ser Gly
    130                 135                 140

Gly Gly Gly Ser Gly Gly Gly Ser Gly Gly Gly Ser Asp Ile
145                 150                 155                 160

Val Met Thr Gln Ser His Ile Phe Met Ser Thr Ser Val Gly Asp Arg
                165                 170                 175

Val Ser Ile Thr Cys Lys Ala Ser Gln Asp Val Asp Thr Ala Val Ala
            180                 185                 190

Trp Tyr Gln Gln Lys Pro Gly Gln Ser Pro Lys Leu Leu Ile Tyr Trp
        195                 200                 205

Ala Ser Thr Arg Leu Thr Gly Val Pro Asp Arg Phe Thr Gly Ser Gly
    210                 215                 220

Ser Gly Thr Asp Phe Thr Leu Thr Ile Ser Asn Val Gln Ser Glu Asp
225                 230                 235                 240

Leu Ala Asp Tyr Phe Cys Gln Gln Tyr Ser Ser Tyr Pro Tyr Thr Phe
                245                 250                 255

Gly Gly Gly Thr Lys Leu Glu Ile Lys Gly Leu Ala Val Ser Thr Ile
            260                 265                 270

Ser Ser Phe Phe Pro Pro Gly Tyr Gln Ile Tyr Ile Trp Ala Pro Leu
        275                 280                 285

Ala Gly Thr Cys Gly Val Leu Leu Leu Ser Leu Val Ile Thr Leu Tyr
    290                 295                 300

Cys Lys Arg Gly Arg Lys Lys Leu Leu Tyr Ile Phe Lys Gln Pro Phe
305                 310                 315                 320

Met Arg Pro Val Gln Thr Thr Gln Glu Glu Asp Gly Cys Ser Cys Arg
                325                 330                 335

Phe Pro Glu Glu Glu Glu Gly Gly Cys Glu Leu Arg Val Lys Phe Ser
            340                 345                 350
```

-continued

```
Arg Ser Ala Asp Ala Pro Ala Tyr Gln Gln Gly Gln Asn Gln Leu Tyr
            355                 360                 365

Asn Glu Leu Asn Leu Gly Arg Arg Glu Glu Tyr Asp Val Leu Asp Lys
        370                 375                 380

Arg Arg Gly Arg Asp Pro Glu Met Gly Gly Lys Pro Arg Arg Lys Asn
385                 390                 395                 400

Pro Gln Glu Gly Leu Tyr Asn Glu Leu Gln Lys Asp Lys Met Ala Glu
                405                 410                 415

Ala Tyr Ser Glu Ile Gly Met Lys Gly Glu Arg Arg Arg Gly Lys Gly
            420                 425                 430

His Asp Gly Leu Tyr Gln Gly Leu Ser Thr Ala Thr Lys Asp Thr Tyr
        435                 440                 445

Asp Ala Leu His Met Gln Ala Leu Pro Pro Arg
    450                 455
```

<210> SEQ ID NO 38
<211> LENGTH: 462
<212> TYPE: PRT
<213> ORGANISM: artificial sequence
<220> FEATURE:
<223> OTHER INFORMATION: A3-v2 polypeptide CAR sequence

<400> SEQUENCE: 38

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Lys Gly Ser Leu Lys Leu Ser Cys Ala Ala Ser Gly Phe
        35                  40                  45

Thr Phe Asn Thr Tyr Ala Met Asn Trp Val Arg Gln Ala Pro Gly Lys
    50                  55                  60

Gly Leu Glu Trp Val Ala Arg Ile Arg Ser Lys Ser Asn Asn Tyr Ala
65                  70                  75                  80

Thr Tyr Tyr Ala Asp Ser Val Lys Asp Arg Phe Thr Ile Ser Arg Asp
                85                  90                  95

Asp Ser Gln Ser Met Leu Tyr Leu Gln Met Asn Asn Leu Lys Thr Glu
            100                 105                 110

Asp Thr Ala Met Tyr Tyr Cys Val Arg Gln Trp Asp Tyr Asp Val Arg
        115                 120                 125

Ala Met Asn Tyr Trp Gly Gln Gly Thr Ser Val Thr Val Ser Ser Gly
    130                 135                 140

Gly Gly Gly Ser Gly Gly Gly Ser Gly Gly Gly Ser Asp Ile
145                 150                 155                 160

Val Met Thr Gln Ser His Ile Phe Met Ser Thr Ser Val Gly Asp Arg
                165                 170                 175

Val Ser Ile Thr Cys Lys Ala Ser Gln Asp Val Asp Thr Ala Val Ala
            180                 185                 190

Trp Tyr Gln Gln Lys Pro Gly Gln Ser Pro Lys Leu Leu Ile Tyr Trp
        195                 200                 205

Ala Ser Thr Arg Leu Thr Gly Val Pro Asp Arg Phe Thr Gly Ser Gly
    210                 215                 220

Ser Gly Thr Asp Phe Thr Leu Thr Ile Ser Asn Val Gln Ser Glu Asp
225                 230                 235                 240

Leu Ala Asp Tyr Phe Cys Gln Gln Tyr Ser Ser Tyr Pro Tyr Thr Phe
                245                 250                 255
```

```
Gly Gly Gly Thr Lys Leu Glu Ile Lys Gly Leu Ala Val Ser Thr Ile
            260                 265                 270

Ser Ser Phe Phe Pro Pro Gly Tyr Gln Ile Ile Ser Phe Leu Ala
        275                 280                 285

Leu Thr Ser Thr Ala Leu Leu Phe Leu Leu Phe Phe Leu Thr Leu Arg
    290                 295                 300

Phe Ser Val Val Lys Arg Gly Arg Lys Leu Leu Tyr Ile Phe Lys
305                 310                 315                 320

Gln Pro Phe Met Arg Pro Val Gln Thr Thr Gln Glu Glu Asp Gly Cys
                325                 330                 335

Ser Cys Arg Phe Pro Glu Glu Glu Gly Gly Cys Glu Leu Arg Val
            340                 345                 350

Lys Phe Ser Arg Ser Ala Asp Ala Pro Ala Tyr Gln Gln Gly Gln Asn
            355                 360                 365

Gln Leu Tyr Asn Glu Leu Asn Leu Gly Arg Arg Glu Glu Tyr Asp Val
    370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
            420                 425                 430

Gly Lys Gly His Asp Gly Leu Tyr Gln Gly Leu Ser Thr Ala Thr Lys
        435                 440                 445

Asp Thr Tyr Asp Ala Leu His Met Gln Ala Leu Pro Pro Arg
    450                 455                 460

<210> SEQ ID NO 39
<211> LENGTH: 488
<212> TYPE: PRT
<213> ORGANISM: artificial sequence
<220> FEATURE:
<223> OTHER INFORMATION: A3-v3 polypeptide CAR sequence

<400> SEQUENCE: 39

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Lys Gly Ser Leu Lys Leu Ser Cys Ala Ala Ser Gly Phe
        35                  40                  45

Thr Phe Asn Thr Tyr Ala Met Asn Trp Val Arg Gln Ala Pro Gly Lys
    50                  55                  60

Gly Leu Glu Trp Val Ala Arg Ile Arg Ser Lys Ser Asn Asn Tyr Ala
65                  70                  75                  80

Thr Tyr Tyr Ala Asp Ser Val Lys Asp Arg Phe Thr Ile Ser Arg Asp
            85                  90                  95

Asp Ser Gln Ser Met Leu Tyr Leu Gln Met Asn Asn Leu Lys Thr Glu
            100                 105                 110

Asp Thr Ala Met Tyr Tyr Cys Val Arg Gln Trp Asp Tyr Asp Val Arg
        115                 120                 125

Ala Met Asn Tyr Trp Gly Gln Gly Thr Ser Val Thr Val Ser Ser Gly
    130                 135                 140

Gly Gly Gly Ser Gly Gly Gly Gly Ser Gly Gly Gly Gly Ser Asp Ile
145                 150                 155                 160
```

Val Met Thr Gln Ser His Ile Phe Met Ser Thr Ser Val Gly Asp Arg
            165                 170                 175

Val Ser Ile Thr Cys Lys Ala Ser Gln Asp Val Asp Thr Ala Val Ala
            180                 185                 190

Trp Tyr Gln Gln Lys Pro Gly Gln Ser Pro Lys Leu Leu Ile Tyr Trp
            195                 200                 205

Ala Ser Thr Arg Leu Thr Gly Val Pro Asp Arg Phe Thr Gly Ser Gly
            210                 215                 220

Ser Gly Thr Asp Phe Thr Leu Thr Ile Ser Asn Val Gln Ser Glu Asp
225                 230                 235                 240

Leu Ala Asp Tyr Phe Cys Gln Gln Tyr Ser Ser Tyr Pro Tyr Thr Phe
            245                 250                 255

Gly Gly Gly Thr Lys Leu Glu Ile Lys Thr Thr Thr Pro Ala Pro Arg
            260                 265                 270

Pro Pro Thr Pro Ala Pro Thr Ile Ala Ser Gln Pro Leu Ser Leu Arg
            275                 280                 285

Pro Glu Ala Cys Arg Pro Ala Ala Gly Gly Ala Val His Thr Arg Gly
            290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
            325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
            355                 360                 365

Glu Glu Glu Gly Gly Cys Glu Leu Arg Val Lys Phe Ser Arg Ser Ala
            370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
            405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
            435                 440                 445

Glu Ile Gly Met Lys Gly Glu Arg Arg Arg Gly Lys Gly His Asp Gly
            450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
            485

<210> SEQ ID NO 40
<211> LENGTH: 491
<212> TYPE: PRT
<213> ORGANISM: artificial sequence
<220> FEATURE:
<223> OTHER INFORMATION: A3-v4 polypeptide CAR sequence

<400> SEQUENCE: 40

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

-continued

Val Gln Pro Lys Gly Ser Leu Lys Leu Ser Cys Ala Ala Ser Gly Phe
         35                  40                  45

Thr Phe Asn Thr Tyr Ala Met Asn Trp Val Arg Gln Ala Pro Gly Lys
     50                  55                  60

Gly Leu Glu Trp Val Ala Arg Ile Arg Ser Lys Ser Asn Asn Tyr Ala
 65                  70                  75                  80

Thr Tyr Tyr Ala Asp Ser Val Lys Asp Arg Phe Thr Ile Ser Arg Asp
                 85                  90                  95

Asp Ser Gln Ser Met Leu Tyr Leu Gln Met Asn Asn Leu Lys Thr Glu
                100                 105                 110

Asp Thr Ala Met Tyr Tyr Cys Val Arg Gln Trp Asp Tyr Asp Val Arg
            115                 120                 125

Ala Met Asn Tyr Trp Gly Gln Gly Thr Ser Val Thr Val Ser Ser Gly
        130                 135                 140

Gly Gly Gly Ser Gly Gly Gly Ser Gly Gly Gly Ser Asp Ile
145                 150                 155                 160

Val Met Thr Gln Ser His Ile Phe Met Ser Thr Ser Val Gly Asp Arg
                165                 170                 175

Val Ser Ile Thr Cys Lys Ala Ser Gln Asp Val Asp Thr Ala Val Ala
            180                 185                 190

Trp Tyr Gln Gln Lys Pro Gly Gln Ser Pro Lys Leu Leu Ile Tyr Trp
        195                 200                 205

Ala Ser Thr Arg Leu Thr Gly Val Pro Asp Arg Phe Thr Gly Ser Gly
    210                 215                 220

Ser Gly Thr Asp Phe Thr Leu Thr Ile Ser Asn Val Gln Ser Glu Asp
225                 230                 235                 240

Leu Ala Asp Tyr Phe Cys Gln Gln Tyr Ser Ser Tyr Pro Tyr Thr Phe
                245                 250                 255

Gly Gly Gly Thr Lys Leu Glu Ile Lys Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Ile Ser Phe Phe Leu Ala Leu Thr Ser
305                 310                 315                 320

Thr Ala Leu Leu Phe Leu Leu Phe Phe Leu Thr Leu Arg Phe Ser Val
                325                 330                 335

Val Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

```
Ala Tyr Ser Glu Ile Gly Met Lys Gly Glu Arg Arg Gly Lys Gly
    450             455             460

His Asp Gly Leu Tyr Gln Gly Leu Ser Thr Ala Thr Lys Asp Thr Tyr
465             470             475             480

Asp Ala Leu His Met Gln Ala Leu Pro Pro Arg
                485             490

<210> SEQ ID NO 41
<211> LENGTH: 674
<212> TYPE: PRT
<213> ORGANISM: artificial sequence
<220> FEATURE:
<223> OTHER INFORMATION: A3-v5 polypeptide CAR sequence

<400> SEQUENCE: 41

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
                20                  25                  30

Val Gln Pro Lys Gly Ser Leu Lys Leu Ser Cys Ala Ala Ser Gly Phe
            35                  40                  45

Thr Phe Asn Thr Tyr Ala Met Asn Trp Val Arg Gln Ala Pro Gly Lys
    50                  55                  60

Gly Leu Glu Trp Val Ala Arg Ile Arg Ser Lys Ser Asn Asn Tyr Ala
65                  70                  75                  80

Thr Tyr Tyr Ala Asp Ser Val Lys Asp Arg Phe Thr Ile Ser Arg Asp
                85                  90                  95

Asp Ser Gln Ser Met Leu Tyr Leu Gln Met Asn Asn Leu Lys Thr Glu
                100                 105                 110

Asp Thr Ala Met Tyr Tyr Cys Val Arg Gln Trp Asp Tyr Asp Val Arg
            115                 120                 125

Ala Met Asn Tyr Trp Gly Gln Gly Thr Ser Val Thr Val Ser Ser Gly
    130                 135                 140

Gly Gly Gly Ser Gly Gly Gly Gly Ser Gly Gly Gly Ser Asp Ile
145                 150                 155                 160

Val Met Thr Gln Ser His Ile Phe Met Ser Thr Ser Val Gly Asp Arg
                165                 170                 175

Val Ser Ile Thr Cys Lys Ala Ser Gln Asp Val Asp Thr Ala Val Ala
            180                 185                 190

Trp Tyr Gln Gln Lys Pro Gly Gln Ser Pro Lys Leu Leu Ile Tyr Trp
    195                 200                 205

Ala Ser Thr Arg Leu Thr Gly Val Pro Asp Arg Phe Thr Gly Ser Gly
    210                 215                 220

Ser Gly Thr Asp Phe Thr Leu Thr Ile Ser Asn Val Gln Ser Glu Asp
225                 230                 235                 240

Leu Ala Asp Tyr Phe Cys Gln Gln Tyr Ser Ser Tyr Pro Tyr Thr Phe
                245                 250                 255

Gly Gly Gly Thr Lys Leu Glu Ile Lys Glu Pro Lys Ser Pro Asp Lys
            260                 265                 270

Thr His Thr Cys Pro Pro Cys Pro Ala Pro Pro Val Ala Gly Pro Ser
    275                 280                 285

Val Phe Leu Phe Pro Pro Lys Pro Lys Asp Thr Leu Met Ile Ala Arg
    290                 295                 300

Thr Pro Glu Val Thr Cys Val Val Asp Val Ser His Glu Asp Pro
305                 310                 315                 320
```

```
Glu Val Lys Phe Asn Trp Tyr Val Asp Gly Val Glu Val His Asn Ala
            325                 330                 335

Lys Thr Lys Pro Arg Glu Glu Gln Tyr Asn Ser Thr Tyr Arg Val Val
        340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr
        370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
            405                 410                 415

Leu Val Lys Gly Phe Tyr Pro Ser Asp Ile Ala Val Glu Trp Glu Ser
        420                 425                 430

Asn Gly Gln Pro Glu Asn Asn Tyr Lys Thr Thr Pro Pro Val Leu Asp
        435                 440                 445

Ser Asp Gly Ser Phe Phe Leu Tyr Ser Lys Leu Thr Val Asp Lys Ser
        450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
            485                 490                 495

Ile Tyr Ile Trp Ala Pro Leu Ala Gly Thr Cys Gly Val Leu Leu Leu
        500                 505                 510

Ser Leu Val Ile Thr Leu Tyr Cys Lys Arg Gly Arg Lys Lys Leu Leu
        515                 520                 525

Tyr Ile Phe Lys Gln Pro Phe Met Arg Pro Val Gln Thr Thr Gln Glu
        530                 535                 540

Glu Asp Gly Cys Ser Cys Arg Phe Pro Glu Glu Glu Glu Gly Gly Cys
545                 550                 555                 560

Glu Leu Arg Val Lys Phe Ser Arg Ser Ala Asp Ala Pro Ala Tyr Gln
            565                 570                 575

Gln Gly Gln Asn Gln Leu Tyr Asn Glu Leu Asn Leu Gly Arg Arg Glu
        580                 585                 590

Glu Tyr Asp Val Leu Asp Lys Arg Arg Gly Arg Asp Pro Glu Met Gly
        595                 600                 605

Gly Lys Pro Arg Arg Lys Asn Pro Gln Glu Gly Leu Tyr Asn Glu Leu
        610                 615                 620

Gln Lys Asp Lys Met Ala Glu Ala Tyr Ser Glu Ile Gly Met Lys Gly
625                 630                 635                 640

Glu Arg Arg Arg Gly Lys Gly His Asp Gly Leu Tyr Gln Gly Leu Ser
            645                 650                 655

Thr Ala Thr Lys Asp Thr Tyr Asp Ala Leu His Met Gln Ala Leu Pro
        660                 665                 670

Pro Arg

<210> SEQ ID NO 42
<211> LENGTH: 677
<212> TYPE: PRT
<213> ORGANISM: artificial sequence
<220> FEATURE:
<223> OTHER INFORMATION: A3-v6 polypeptide CAR sequence

<400> SEQUENCE: 42

Met Ala Leu Pro Val Thr Ala Leu Leu Leu Pro Leu Ala Leu Leu Leu
```

```
1               5                   10                  15
His Ala Ala Arg Pro Glu Val Gln Leu Val Glu Ser Gly Gly Leu
                20                  25                  30

Val Gln Pro Lys Gly Ser Leu Lys Leu Ser Cys Ala Ala Ser Gly Phe
                35                  40                  45

Thr Phe Asn Thr Tyr Ala Met Asn Trp Val Arg Gln Ala Pro Gly Lys
        50                  55                  60

Gly Leu Glu Trp Val Ala Arg Ile Arg Ser Lys Ser Asn Asn Tyr Ala
65                  70                  75                  80

Thr Tyr Tyr Ala Asp Ser Val Lys Asp Arg Phe Thr Ile Ser Arg Asp
                85                  90                  95

Asp Ser Gln Ser Met Leu Tyr Leu Gln Met Asn Asn Leu Lys Thr Glu
                100                 105                 110

Asp Thr Ala Met Tyr Tyr Cys Val Arg Gln Trp Asp Tyr Asp Val Arg
                115                 120                 125

Ala Met Asn Tyr Trp Gly Gln Gly Thr Ser Val Thr Val Ser Ser Gly
                130                 135                 140

Gly Gly Gly Ser Gly Gly Gly Gly Ser Gly Gly Gly Gly Ser Asp Ile
145                 150                 155                 160

Val Met Thr Gln Ser His Ile Phe Met Ser Thr Ser Val Gly Asp Arg
                165                 170                 175

Val Ser Ile Thr Cys Lys Ala Ser Gln Asp Val Asp Thr Ala Val Ala
                180                 185                 190

Trp Tyr Gln Gln Lys Pro Gly Gln Ser Pro Lys Leu Leu Ile Tyr Trp
                195                 200                 205

Ala Ser Thr Arg Leu Thr Gly Val Pro Asp Arg Phe Thr Gly Ser Gly
                210                 215                 220

Ser Gly Thr Asp Phe Thr Leu Thr Ile Ser Asn Val Gln Ser Glu Asp
225                 230                 235                 240

Leu Ala Asp Tyr Phe Cys Gln Gln Tyr Ser Ser Tyr Pro Tyr Thr Phe
                245                 250                 255

Gly Gly Gly Thr Lys Leu Glu Ile Lys Glu Pro Lys Ser Pro Asp Lys
                260                 265                 270

Thr His Thr Cys Pro Pro Cys Pro Ala Pro Val Ala Gly Pro Ser
                275                 280                 285

Val Phe Leu Phe Pro Pro Lys Pro Lys Asp Thr Leu Met Ile Ala Arg
                290                 295                 300

Thr Pro Glu Val Thr Cys Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
                340                 345                 350

Ser Val Leu Thr Val Leu His Gln Asp Trp Leu Asn Gly Lys Glu Tyr
                355                 360                 365

Lys Cys Lys Val Ser Asn Lys Ala Leu Pro Ala Pro Ile Glu Lys Thr
                370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
                405                 410                 415

Leu Val Lys Gly Phe Tyr Pro Ser Asp Ile Ala Val Glu Trp Glu Ser
                420                 425                 430
```

```
Asn Gly Gln Pro Glu Asn Asn Tyr Lys Thr Thr Pro Pro Val Leu Asp
        435                 440                 445
Ser Asp Gly Ser Phe Phe Leu Tyr Ser Lys Leu Thr Val Asp Lys Ser
    450                 455                 460
Arg Trp Gln Gln Gly Asn Val Phe Ser Cys Ser Val Met His Glu Ala
465                 470                 475                 480
Leu His Asn His Tyr Thr Gln Lys Ser Leu Ser Leu Ser Pro Gly Lys
                485                 490                 495
Ile Ile Ser Phe Phe Leu Ala Leu Thr Ser Thr Ala Leu Leu Phe Leu
            500                 505                 510
Leu Phe Phe Leu Thr Leu Arg Phe Ser Val Val Lys Arg Gly Arg Lys
    515                 520                 525
Lys Leu Leu Tyr Ile Phe Lys Gln Pro Phe Met Arg Pro Val Gln Thr
        530                 535                 540
Thr Gln Glu Glu Asp Gly Cys Ser Cys Arg Phe Pro Glu Glu Glu Glu
545                 550                 555                 560
Gly Gly Cys Glu Leu Arg Val Lys Phe Ser Arg Ser Ala Asp Ala Pro
                565                 570                 575
Ala Tyr Gln Gln Gly Gln Asn Gln Leu Tyr Asn Glu Leu Asn Leu Gly
            580                 585                 590
Arg Arg Glu Glu Tyr Asp Val Leu Asp Lys Arg Arg Gly Arg Asp Pro
    595                 600                 605
Glu Met Gly Gly Lys Pro Arg Arg Lys Asn Pro Gln Glu Gly Leu Tyr
        610                 615                 620
Asn Glu Leu Gln Lys Asp Lys Met Ala Glu Ala Tyr Ser Glu Ile Gly
625                 630                 635                 640
Met Lys Gly Glu Arg Arg Arg Gly Lys Gly His Asp Gly Leu Tyr Gln
                645                 650                 655
Gly Leu Ser Thr Ala Thr Lys Asp Thr Tyr Asp Ala Leu His Met Gln
            660                 665                 670
Ala Leu Pro Pro Arg
        675

<210> SEQ ID NO 43
<211> LENGTH: 530
<212> TYPE: PRT
<213> ORGANISM: artificial sequence
<220> FEATURE:
<223> OTHER INFORMATION: TAL binding domain  TRAC_T01-L

<400> SEQUENCE: 43

Leu Thr Pro Gln Gln Val Val Ala Ile Ala Ser Asn Gly Gly Gly Lys
1               5                   10                  15
Gln Ala Leu Glu Thr Val Gln Arg Leu Leu Pro Val Leu Cys Gln Ala
            20                  25                  30
His Gly Leu Thr Pro Gln Gln Val Val Ala Ile Ala Ser Asn Asn Gly
        35                  40                  45
Gly Lys Gln Ala Leu Glu Thr Val Gln Arg Leu Leu Pro Val Leu Cys
    50                  55                  60
Gln Ala His Gly Leu Thr Pro Gln Gln Val Val Ala Ile Ala Ser Asn
65                  70                  75                  80
Gly Gly Gly Lys Gln Ala Leu Glu Thr Val Gln Arg Leu Leu Pro Val
                85                  90                  95
Leu Cys Gln Ala His Gly Leu Thr Pro Glu Gln Val Val Ala Ile Ala
            100                 105                 110
```

```
Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Ala Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Ala Leu Leu Pro Val Leu Cys Gln Ala
    290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365

Leu Cys Gln Ala His Gly Leu Thr Pro Gln Gln Val Val Ala Ile Ala
    370                 375                 380

Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
            420                 425                 430

Leu Leu Pro Val Leu Cys Gln Ala His Gly Leu Thr Pro Gln Gln Val
        435                 440                 445

Val Ala Ile Ala Ser Asn Gly Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525
```

Leu Glu
530

<210> SEQ ID NO 44
<211> LENGTH: 2814
<212> TYPE: DNA
<213> ORGANISM: artificial sequence
<220> FEATURE:
<223> OTHER INFORMATION: polynucleotide encoding TRAC_T01-L TALEN

<400> SEQUENCE: 44

| | |
|---|---|
| atgggcgatc ctaaaaagaa acgtaaggtc atcgattacc catacgatgt tccagattac | 60 |
| gctatcgata tcgccgatct acgcacgctc ggctacagcc agcagcaaca ggagaagatc | 120 |
| aaaccgaagg ttcgttcgac agtggcgcag caccacgagg cactggtcgg ccacgggttt | 180 |
| acacacgcgc acatcgttgc gttaagccaa caccccggcag cgttagggac cgtcgctgtc | 240 |
| aagtatcagg acatgatcgc agcgttgcca gaggcgacac acgaagcgat cgttggcgtc | 300 |
| ggcaaacagt ggtccggcgc acgcgctctg gaggccttgc tcacggtggc gggagagttg | 360 |
| agaggtccac cgttacagtt ggacacaggc caacttctca agattgcaaa acgtggcggc | 420 |
| gtgaccgcag tggaggcagt gcatgcatgg cgcaatgcac tgacgggtgc cccgctcaac | 480 |
| ttgacccccc agcaggtggt ggccatcgcc agcaatggcg gtggcaagca ggcgctggag | 540 |
| acggtccagc ggctgttgcc ggtgctgtgc caggcccacg gcttgacccc ccagcaggtg | 600 |
| gtggccatcg ccagcaataa tggtggcaag caggcgctgg agacggtcca gcggctgttg | 660 |
| ccggtgctgt gccaggccca cggcttgacc cccagcagg tggtggccat cgccagcaat | 720 |
| ggcggtggca agcaggcgct ggagacggtc agcggctgt tgccggtgct gtgccaggcc | 780 |
| cacggcttga ccccggagca ggtggtggcc atcgccagcc acgatggcgg caagcaggcg | 840 |
| ctggagacgg tccagcggct gttgccggtg ctgtgccagg cccacggctt gaccccggag | 900 |
| caggtggtgg ccatcgccag ccacgatggc ggcaagcagg cgctggagac ggtccagcgg | 960 |
| ctgttgccgg tgctgtgcca ggcccacggc ttgaccccgg agcaggtggt ggccatcgcc | 1020 |
| agccacgatg cggcaagca ggcgctggag acggtccagc ggctgttgcc ggtgctgtgc | 1080 |
| caggcccacg gcttgacccc ggagcaggtg gtggccatcg ccagcaatat tggtggcaag | 1140 |
| caggcgctgg agacggtgca ggcgctgttg ccggtgctgt gccaggccca cggcttgacc | 1200 |
| ccggagcagg tggtggccat cgccagccac gatggcggca agcaggcgct ggagacggtc | 1260 |
| cagcggctgt tgccggtgct gtgccaggcc cacggcttga ccccggagca ggtggtggcc | 1320 |
| atcgccagca atattggtgg caagcaggcg ctggagacgg tgcaggcgct gttgccggtg | 1380 |
| ctgtgccagg cccacggctt gaccccccag caggtggtgg ccatcgccag caataatggt | 1440 |
| ggcaagcagg cgctggagac ggtccagcgg ctgttgccgg tgctgtgcca ggcccacggc | 1500 |
| ttgaccccgg agcaggtggt ggccatcgcc agcaatattg tggcaagca ggcgctggag | 1560 |
| acggtgcagg cgctgttgcc ggtgctgtgc caggcccacg gcttgacccc ccagcaggtg | 1620 |
| gtggccatcg ccagcaatgg cggtggcaag caggcgctgg agacggtcca gcggctgttg | 1680 |
| ccggtgctgt gccaggccca cggcttgacc ccggagcagg tggtggccat cgccagcaat | 1740 |
| attggtggca agcaggcgct ggagacggtg caggcgctgt tgccggtgct gtgccaggcc | 1800 |
| cacggcttga ccccccagca ggtggtggcc atcgccagca atggcggtgg caagcaggcg | 1860 |
| ctggagacgg tccagcggct gttgccggtg ctgtgccagg cccacggctt gaccccggag | 1920 |
| caggtggtgg ccatcgccag ccacgatggc ggcaagcagg cgctggagac ggtccagcgg | 1980 |

| | |
|---|---:|
| ctgttgccgg tgctgtgcca ggcccacggc ttgacccctc agcaggtggt ggccatcgcc | 2040 |
| agcaatggcg gcggcaggcc ggcgctggag agcattgttg cccagttatc tcgccctgat | 2100 |
| ccggcgttgg ccgcgttgac caacgaccac ctcgtcgcct tggcctgcct cggcgggcgt | 2160 |
| cctgcgctga tgcagtgaaa aagggattgg gggatccta tcagccgttc ccagctggtg | 2220 |
| aagtccgagc tggaggagaa gaaatccgag ttgaggcaca agctgaagta cgtgccccac | 2280 |
| gagtacatcg agctgatcga gatcgcccgg aacagcaccc aggaccgtat cctggagatg | 2340 |
| aaggtgatgg agttcttcat gaaggtgtac ggctacaggg gcaagcacct gggcggctcc | 2400 |
| aggaagcccg acggcgccat ctacaccgtg ggctccccca tcgactacgg cgtgatcgtg | 2460 |
| gacaccaagg cctactccgg cggctacaac ctgcccatcg ccaggccga cgaaatgcag | 2520 |
| aggtacgtgg aggagaacca gaccaggaac aagcacatca accccaacga gtggtggaag | 2580 |
| gtgtaccccct ccagcgtgac cgagttcaag ttcctgttcg tgtccggcca cttcaagggc | 2640 |
| aactacaagg cccagctgac caggctgaac cacatcacca actgcaacgg cgccgtgctg | 2700 |
| tccgtggagg agctcctgat cggcggcgag atgatcaagg ccggcaccct gacccctgag | 2760 |
| gaggtgagga ggaagttcaa caacggcgag atcaacttcg cggccgactg ataa | 2814 |

<210> SEQ ID NO 45
<211> LENGTH: 2832
<212> TYPE: DNA
<213> ORGANISM: artificial sequence
<220> FEATURE:
<223> OTHER INFORMATION: polynucleotide encoding TRAC_T01-R TALEN

<400> SEQUENCE: 45

| | |
|---|---:|
| atgggcgatc ctaaaaagaa acgtaaggtc atcgataagg agaccgccgc tgccaagttc | 60 |
| gagagacagc acatggacag catcgatatc gccgatctac gcacgctcgg ctacagccag | 120 |
| cagcaacagg agaagatcaa accgaaggtt cgttcgacag tggcgcagca ccacgaggca | 180 |
| ctggtcggcc acgggtttac acacgcgcac atcgttgcgt taagccaaca cccggcagcg | 240 |
| ttagggaccg tcgctgtcaa gtatcaggac atgatcgcag cgttgccaga ggcgacacac | 300 |
| gaagcgatct tggcgtcgg caaacagtgg tccggcgcac gcgctctgga ggccttgctc | 360 |
| acggtggcgg gagagttgag aggtccaccg ttacagttgg acacaggcca acttctcaag | 420 |
| attgcaaaac gtggcggcgt gaccgcagtg gaggcagtgc atgcatggcg caatgcactg | 480 |
| acgggtgccc cgctcaactt gacccccgag caggtggtgg ccatcgccag ccacgatggc | 540 |
| ggcaagcagg cgctggagac ggtccagcgg ctgttgccgg tgctgtgcca ggcccacggc | 600 |
| ttgacccccc agcaggtggt ggccatcgcc agcaatggcg gtggcaagca ggcgctggag | 660 |
| acggtccagc ggctgttgcc ggtgctgtgc caggcccacg gcttgacccc ggagcaggtg | 720 |
| gtggccatcg ccagccacga tggcggcaag caggcgctgg agacggtcca gcggctgttg | 780 |
| ccggtgctgt gccaggccca cggcttgacc ccggagcagg tggtggccat cgccagcaat | 840 |
| attggtggca gcaggcgct ggagacggtg caggcgctgt gccggtgct gtgccaggcc | 900 |
| cacggcttga ccccccagca ggtggtggcc atcgccagca ataatggtgg caagcaggcg | 960 |
| ctggagacgt ccagcggct gttgccggtg ctgtgccagg cccacggctt gaccccggag | 1020 |
| caggtggtgg ccatcgccag ccacgatggc ggcaagcagg cgctggagac ggtccagcgg | 1080 |
| ctgttgccgg tgctgtgcca ggcccacggc ttgacccccc agcaggtggt ggccatcgcc | 1140 |
| agcaatggcg gtggcaagca ggcgctggag acggtccagc ggctgttgcc ggtgctgtgc | 1200 |
| caggcccacg gcttgacccc ccagcaggtg gtggccatcg ccagcaataa tggtggcaag | 1260 |

```
caggcgctgg agacggtcca gcggctgttg ccggtgctgt gccaggccca cggcttgacc    1320
ccccagcagg tggtggccat cgccagcaat aatggtggca agcaggcgct ggagacggtc    1380
cagcggctgt tgccggtgct gtgccaggcc cacggcttga ccccccagca ggtggtggcc    1440
atcgccagca atggcggtgg caagcaggcg ctggagacgg tccagcggct gttgccggtg    1500
ctgtgccagg cccacggctt gaccccggag caggtggtgg ccatcgccag caatattggt    1560
ggcaagcagg cgctggagac ggtgcaggcg ctgttgccgg tgctgtgcca ggcccacggc    1620
ttgaccccgg agcaggtggt ggccatcgcc agccacgatg gcggcaagca ggcgctggag    1680
acggtccagc ggctgttgcc ggtgctgtgc caggcccacg gcttgacccc ggagcaggtg    1740
gtggccatcg ccagcaatat tggtggcaag caggcgctgg agacggtgca ggcgctgttg    1800
ccggtgctgt gccaggccca cggcttgacc ccggagcagg tggtggccat cgccagccac    1860
gatggcggca agcaggcgct ggagacggtc agcggctgt tgccggtgct gtgccaggcc    1920
cacggcttga ccccccagca ggtggtggcc atcgccagca ataatggtgg caagcaggcg    1980
ctggagacgg tccagcggct gttgccggtg ctgtgccagg cccacggctt gacccctcag    2040
caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg gaggagaaga atccgagtt gaggcacaag    2280 ctgaagtacg tgccccacga gtacatcgag ctgatcgaga tcgcccggaa cagcacccag    2340
gaccgtatcc tggagatgaa ggtgatggag ttcttcatga aggtgtacgg ctacaggggc    2400
aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
cccaacgagt ggtggaaggt gtaccctcc agcgtgaccg agttcaagtt cctgttcgtg    2640
tccggccact tcaagggcaa ctacaaggcc agctgacca ggctgaacca catcaccaac    2700
tgcaacggcg ccgtgctgtc cgtggaggag ctcctgatcg gcggcgagat gatcaaggcc    2760
ggcaccctga ccctggagga ggtgaggagg aagttcaaca acggcgagat caacttcgcg    2820
gccgactgat aa                                                       2832
```

<210> SEQ ID NO 46
<211> LENGTH: 530
<212> TYPE: PRT
<213> ORGANISM: artificial sequence
<220> FEATURE:
<223> OTHER INFORMATION: TAL binding domain  TRAC_T01-L

<400> SEQUENCE: 46

Leu Thr Pro Gln Gln Val Val Ala Ile Ala Ser Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

```
Gly Gly Gly Lys Gln Ala Leu Glu Thr Val Gln Arg Leu Leu Pro Val
            85                  90                  95
Leu Cys Gln Ala His Gly Leu Thr Pro Glu Gln Val Val Ala Ile Ala
            100                 105                 110
Ser His Asp Gly Gly Lys Gln Ala Leu Glu Thr Val Gln Arg Leu Leu
            115                 120                 125
Pro Val Leu Cys Gln Ala His Gly Leu Thr Pro Glu Gln Val Val Ala
130                 135                 140
Ile Ala Ser His Asp Gly Gly Lys Gln Ala Leu Glu Thr Val Gln Arg
145                 150                 155                 160
Leu Leu Pro Val Leu Cys Gln Ala His Gly Leu Thr Pro Glu Gln Val
                165                 170                 175
Val Ala Ile Ala Ser His Asp Gly Gly Lys Gln Ala Leu Glu Thr Val
                180                 185                 190
Gln Arg Leu Leu Pro Val Leu Cys Gln Ala His Gly Leu Thr Pro Glu
            195                 200                 205
Gln Val Val Ala Ile Ala Ser Asn Ile Gly Gly Lys Gln Ala Leu Glu
            210                 215                 220
Thr Val Gln Ala Leu Leu Pro Val Leu Cys Gln Ala His Gly Leu Thr
225                 230                 235                 240
Pro Glu Gln Val Val Ala Ile Ala Ser His Asp Gly Gly Lys Gln Ala
                245                 250                 255
Leu Glu Thr Val Gln Arg Leu Leu Pro Val Leu Cys Gln Ala His Gly
                260                 265                 270
Leu Thr Pro Glu Gln Val Val Ala Ile Ala Ser Asn Ile Gly Gly Lys
            275                 280                 285
Gln Ala Leu Glu Thr Val Gln Ala Leu Leu Pro Val Leu Cys Gln Ala
            290                 295                 300
His Gly Leu Thr Pro Gln Gln Val Val Ala Ile Ala Ser Asn Asn Gly
305                 310                 315                 320
Gly Lys Gln Ala Leu Glu Thr Val Gln Arg Leu Leu Pro Val Leu Cys
                325                 330                 335
Gln Ala His Gly Leu Thr Pro Glu Gln Val Val Ala Ile Ala Ser Asn
                340                 345                 350
Ile Gly Gly Lys Gln Ala Leu Glu Thr Val Gln Ala Leu Leu Pro Val
            355                 360                 365
Leu Cys Gln Ala His Gly Leu Thr Pro Gln Gln Val Val Ala Ile Ala
            370                 375                 380
Ser Asn Gly Gly Gly Lys Gln Ala Leu Glu Thr Val Gln Arg Leu Leu
385                 390                 395                 400
Pro Val Leu Cys Gln Ala His Gly Leu Thr Pro Glu Gln Val Val Ala
                405                 410                 415
Ile Ala Ser Asn Ile Gly Gly Lys Gln Ala Leu Glu Thr Val Gln Ala
                420                 425                 430
Leu Leu Pro Val Leu Cys Gln Ala His Gly Leu Thr Pro Gln Gln Val
            435                 440                 445
Val Ala Ile Ala Ser Asn Gly Gly Gly Lys Gln Ala Leu Glu Thr Val
            450                 455                 460
Gln Arg Leu Leu Pro Val Leu Cys Gln Ala His Gly Leu Thr Pro Glu
465                 470                 475                 480
Gln Val Val Ala Ile Ala Ser His Asp Gly Gly Lys Gln Ala Leu Glu
                485                 490                 495
```

```
Thr Val Gln Arg Leu Leu Pro Val Leu Cys Gln Ala His Gly Leu Thr
            500                 505                 510
Pro Gln Gln Val Val Ala Ile Ala Ser Asn Gly Gly Arg Pro Ala
        515                 520                 525
Leu Glu
    530

<210> SEQ ID NO 47
<211> LENGTH: 530
<212> TYPE: PRT
<213> ORGANISM: artificial sequence
<220> FEATURE:
<223> OTHER INFORMATION: TAL binding domain TRAC_T01-R

<400> SEQUENCE: 47

Leu Thr Pro Glu Gln Val Val Ala Ile Ala Ser His Asp Gly Gly Lys
1               5                   10                  15
Gln Ala Leu Glu Thr Val Gln Arg Leu Leu Pro Val Leu Cys Gln Ala
            20                  25                  30
His Gly Leu Thr Pro Gln Gln Val Val Ala Ile Ala Ser Asn Gly Gly
        35                  40                  45
Gly Lys Gln Ala Leu Glu Thr Val Gln Arg Leu Leu Pro Val Leu Cys
    50                  55                  60
Gln Ala His Gly Leu Thr Pro Glu Gln Val Val Ala Ile Ala Ser His
65                  70                  75                  80
Asp Gly Gly Lys Gln Ala Leu Glu Thr Val Gln Arg Leu Leu Pro Val
                85                  90                  95
Leu Cys Gln Ala His Gly Leu Thr Pro Glu Gln Val Val Ala Ile Ala
            100                 105                 110
Ser Asn Ile Gly Gly Lys Gln Ala Leu Glu Thr Val Gln Ala Leu Leu
        115                 120                 125
Pro Val Leu Cys Gln Ala His Gly Leu Thr Pro Gln Gln Val Val Ala
    130                 135                 140
Ile Ala Ser Asn Asn Gly Gly Lys Gln Ala Leu Glu Thr Val Gln Arg
145                 150                 155                 160
Leu Leu Pro Val Leu Cys Gln Ala His Gly Leu Thr Pro Glu Gln Val
                165                 170                 175
Val Ala Ile Ala Ser His Asp Gly Gly Lys Gln Ala Leu Glu Thr Val
            180                 185                 190
Gln Arg Leu Leu Pro Val Leu Cys Gln Ala His Gly Leu Thr Pro Gln
        195                 200                 205
Gln Val Val Ala Ile Ala Ser Asn Gly Gly Lys Gln Ala Leu Glu
    210                 215                 220
Thr Val Gln Arg Leu Leu Pro Val Leu Cys Gln Ala His Gly Leu Thr
225                 230                 235                 240
Pro Gln Gln Val Val Ala Ile Ala Ser Asn Asn Gly Gly Lys Gln Ala
                245                 250                 255
Leu Glu Thr Val Gln Arg Leu Leu Pro Val Leu Cys Gln Ala His Gly
            260                 265                 270
Leu Thr Pro Gln Gln Val Val Ala Ile Ala Ser Asn Asn Gly Gly Lys
        275                 280                 285
Gln Ala Leu Glu Thr Val Gln Arg Leu Leu Pro Val Leu Cys Gln Ala
    290                 295                 300
His Gly Leu Thr Pro Gln Gln Val Val Ala Ile Ala Ser Asn Gly Gly
305                 310                 315                 320
```

-continued

```
Gly Lys Gln Ala Leu Glu Thr Val Gln Arg Leu Leu Pro Val Leu Cys
            325                 330                 335
Gln Ala His Gly Leu Thr Pro Glu Gln Val Val Ala Ile Ala Ser Asn
        340                 345                 350
Ile Gly Gly Lys Gln Ala Leu Glu Thr Val Gln Ala Leu Leu Pro Val
    355                 360                 365
Leu Cys Gln Ala His Gly Leu Thr Pro Glu Gln Val Val Ala Ile Ala
370                 375                 380
Ser His Asp Gly Gly Lys Gln Ala Leu Glu Thr Val Gln Arg Leu Leu
385                 390                 395                 400
Pro Val Leu Cys Gln Ala His Gly Leu Thr Pro Glu Gln Val Val Ala
                405                 410                 415
Ile Ala Ser Asn Ile Gly Gly Lys Gln Ala Leu Glu Thr Val Gln Ala
            420                 425                 430
Leu Leu Pro Val Leu Cys Gln Ala His Gly Leu Thr Pro Glu Gln Val
        435                 440                 445
Val Ala Ile Ala Ser His Asp Gly Gly Lys Gln Ala Leu Glu Thr Val
    450                 455                 460
Gln Arg Leu Leu Pro Val Leu Cys Gln Ala His Gly Leu Thr Pro Gln
465                 470                 475                 480
Gln Val Val Ala Ile Ala Ser Asn Gly Gly Lys Gln Ala Leu Glu
                485                 490                 495
Thr Val Gln Arg Leu Leu Pro Val Leu Cys Gln Ala His Gly Leu Thr
                500                 505                 510
Pro Gln Gln Val Val Ala Ile Ala Ser Asn Gly Gly Gly Arg Pro Ala
            515                 520                 525
Leu Glu
    530

<210> SEQ ID NO 48
<211> LENGTH: 8
<212> TYPE: PRT
<213> ORGANISM: artificial sequence
<220> FEATURE:
<223> OTHER INFORMATION: CDR1 of H8 VH chain

<400> SEQUENCE: 48

Gly Tyr Ser Phe Thr Gly Tyr Tyr
1               5

<210> SEQ ID NO 49
<211> LENGTH: 8
<212> TYPE: PRT
<213> ORGANISM: artificial sequence
<220> FEATURE:
<223> OTHER INFORMATION: CDR2 of H8 VH chain

<400> SEQUENCE: 49

Ile Asn Pro Asn Asn Gly Val Thr
1               5

<210> SEQ ID NO 50
<211> LENGTH: 13
<212> TYPE: PRT
<213> ORGANISM: artificial sequence
<220> FEATURE:
<223> OTHER INFORMATION: CDR3 of H8 VH chain

<400> SEQUENCE: 50

Ala Arg Ser Thr Met Ile Thr Asn Tyr Val Met Asp Tyr
```

```
1               5                    10

<210> SEQ ID NO 51
<211> LENGTH: 6
<212> TYPE: PRT
<213> ORGANISM: artificial sequence
<220> FEATURE:
<223> OTHER INFORMATION: CDR1 of H8 VL chain

<400> SEQUENCE: 51

Gln Ser Val Ser Asn Asp
1               5

<210> SEQ ID NO 52
<211> LENGTH: 3
<212> TYPE: PRT
<213> ORGANISM: artificial sequence
<220> FEATURE:
<223> OTHER INFORMATION: CDR2 of H8 VL chain

<400> SEQUENCE: 52

Tyr Thr Ser
1

<210> SEQ ID NO 53
<211> LENGTH: 9
<212> TYPE: PRT
<213> ORGANISM: artificial sequence
<220> FEATURE:
<223> OTHER INFORMATION: CDR3 of H8 VL chain

<400> SEQUENCE: 53

Gln Gln Asp Tyr Asn Ser Pro Pro Thr
1               5

<210> SEQ ID NO 54
<211> LENGTH: 8
<212> TYPE: PRT
<213> ORGANISM: artificial sequence
<220> FEATURE:
<223> OTHER INFORMATION: CDR1 of A1 VH chain

<400> SEQUENCE: 54

Gly Tyr Thr Phe Thr Asn Phe Gly
1               5

<210> SEQ ID NO 55
<211> LENGTH: 8
<212> TYPE: PRT
<213> ORGANISM: artificial sequence
<220> FEATURE:
<223> OTHER INFORMATION: CDR2 of A1 VH chain

<400> SEQUENCE: 55

Ile Asn Thr Asn Thr Gly Glu Pro
1               5

<210> SEQ ID NO 56
<211> LENGTH: 12
<212> TYPE: PRT
<213> ORGANISM: artificial sequence
<220> FEATURE:
<223> OTHER INFORMATION: CDR3 of A1 VH chain

<400> SEQUENCE: 56

Ala Arg Asp Trp Asp Gly Ala Tyr Phe Phe Asp Tyr
1               5                    10
```

<210> SEQ ID NO 57
<211> LENGTH: 6
<212> TYPE: PRT
<213> ORGANISM: artificial sequence
<220> FEATURE:
<223> OTHER INFORMATION: CDR1 of A1 VL chain

<400> SEQUENCE: 57

Gln Ser Val Ser Asn Asp
1               5

<210> SEQ ID NO 58
<211> LENGTH: 3
<212> TYPE: PRT
<213> ORGANISM: artificial sequence
<220> FEATURE:
<223> OTHER INFORMATION: CDR2 of A1 VL chain

<400> SEQUENCE: 58

Phe Ala Thr
1

<210> SEQ ID NO 59
<211> LENGTH: 9
<212> TYPE: PRT
<213> ORGANISM: artificial sequence
<220> FEATURE:
<223> OTHER INFORMATION: CDR3 of A1 VL chain

<400> SEQUENCE: 59

Gln Gln Asp Tyr Ser Ser Pro Trp Thr
1               5

<210> SEQ ID NO 60
<211> LENGTH: 8
<212> TYPE: PRT
<213> ORGANISM: artificial sequence
<220> FEATURE:
<223> OTHER INFORMATION: CDR1 of A2 VH chain

<400> SEQUENCE: 60

Gly Tyr Thr Phe Thr Asp Tyr Val
1               5

<210> SEQ ID NO 61
<211> LENGTH: 8
<212> TYPE: PRT
<213> ORGANISM: artificial sequence
<220> FEATURE:
<223> OTHER INFORMATION: CDR2 of A2 VH chain

<400> SEQUENCE: 61

Ile Tyr Pro Gly Ser Asn Ser Ile
1               5

<210> SEQ ID NO 62
<211> LENGTH: 10
<212> TYPE: PRT
<213> ORGANISM: artificial sequence
<220> FEATURE:
<223> OTHER INFORMATION: CDR3 of A2 VH chain

<400> SEQUENCE: 62

Ala Met Gly Gly Asn Tyr Gly Phe Asp Tyr
1               5                   10

```
<210> SEQ ID NO 63
<211> LENGTH: 7
<212> TYPE: PRT
<213> ORGANISM: artificial sequence
<220> FEATURE:
<223> OTHER INFORMATION: CDR1 of A2 VL chain

<400> SEQUENCE: 63

Ser Ser Val Asn Ser Asn Tyr
1               5

<210> SEQ ID NO 64
<211> LENGTH: 3
<212> TYPE: PRT
<213> ORGANISM: artificial sequence
<220> FEATURE:
<223> OTHER INFORMATION: CDR2 of A2 VL chain

<400> SEQUENCE: 64

Ser Thr Ser
1

<210> SEQ ID NO 65
<211> LENGTH: 9
<212> TYPE: PRT
<213> ORGANISM: artificial sequence
<220> FEATURE:
<223> OTHER INFORMATION: CDR3 of A2 VL chain

<400> SEQUENCE: 65

His Gln Tyr His Arg Ser Pro Leu Thr
1               5

<210> SEQ ID NO 66
<211> LENGTH: 8
<212> TYPE: PRT
<213> ORGANISM: artificial sequence
<220> FEATURE:
<223> OTHER INFORMATION: CDR1 of A3 VH chain

<400> SEQUENCE: 66

Gly Phe Thr Phe Asn Thr Tyr Ala
1               5

<210> SEQ ID NO 67
<211> LENGTH: 10
<212> TYPE: PRT
<213> ORGANISM: artificial sequence
<220> FEATURE:
<223> OTHER INFORMATION: CDR2 of A3 VH chain

<400> SEQUENCE: 67

Ile Arg Ser Lys Ser Asn Asn Tyr Ala Thr
1               5                   10

<210> SEQ ID NO 68
<211> LENGTH: 13
<212> TYPE: PRT
<213> ORGANISM: artificial sequence
<220> FEATURE:
<223> OTHER INFORMATION: CDR3 of A3 VH chain

<400> SEQUENCE: 68

Val Arg Gln Trp Asp Tyr Asp Val Arg Ala Met Asn Tyr
1               5                   10
```

```
<210> SEQ ID NO 69
<211> LENGTH: 6
<212> TYPE: PRT
<213> ORGANISM: artificial sequence
<220> FEATURE:
<223> OTHER INFORMATION: CDR1 of A3 VL chain

<400> SEQUENCE: 69

Gln Asp Val Asp Thr Ala
1               5

<210> SEQ ID NO 70
<211> LENGTH: 3
<212> TYPE: PRT
<213> ORGANISM: artificial sequence
<220> FEATURE:
<223> OTHER INFORMATION: CDR2 of A3 VL chain

<400> SEQUENCE: 70

Trp Ala Ser
1

<210> SEQ ID NO 71
<211> LENGTH: 9
<212> TYPE: PRT
<213> ORGANISM: artificial sequence
<220> FEATURE:
<223> OTHER INFORMATION: CDR3 of A3 VL chain

<400> SEQUENCE: 71

Gln Gln Tyr Ser Ser Tyr Pro Tyr Thr
1               5
```